(12) United States Patent
Rice et al.

(10) Patent No.: US 11,007,213 B2
(45) Date of Patent: May 18, 2021

(54) METABOLICALLY STABILIZED DOUBLE STRANDED MRNA

(71) Applicant: University of Iowa Research Foundation, Iowa City, IA (US)

(72) Inventors: Kevin G. Rice, Iowa City, IA (US); Samuel T. Crowley, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 16/090,468

(22) PCT Filed: Mar. 31, 2017

(86) PCT No.: PCT/US2017/025527
§ 371 (c)(1),
(2) Date: Oct. 1, 2018

(87) PCT Pub. No.: WO2017/173354
PCT Pub. Date: Oct. 5, 2017

(65) Prior Publication Data
US 2019/0111070 A1 Apr. 18, 2019

Related U.S. Application Data

(60) Provisional application No. 62/317,142, filed on Apr. 1, 2016, provisional application No. 62/335,186, filed on May 12, 2016.

(51) Int. Cl.
| | | |
|---|---|---|
| *C07H 21/02* | (2006.01) | |
| *A61K 31/713* | (2006.01) | |
| *A61K 39/00* | (2006.01) | |
| *A61K 39/12* | (2006.01) | |
| *C12N 15/67* | (2006.01) | |

(52) U.S. Cl.
CPC .... *A61K 31/713* (2013.01); *A61K 39/001191* (2018.08); *A61K 39/12* (2013.01); *C07H 21/02* (2013.01); *C12N 15/67* (2013.01); *A61K 2039/53* (2013.01)

(58) Field of Classification Search
CPC .............................. A61K 31/713; C07H 21/02
USPC ...................................... 536/23.1, 23.5, 24.2
See application file for complete search history.

(56) References Cited

U.S. PATENT DOCUMENTS

2014/0328825 A1  11/2014  Meis et al.

FOREIGN PATENT DOCUMENTS

| WO | WO-2007024708 A2 | 3/2007 |
| WO | WO-2013185067 A1 | 12/2013 |
| WO | WO-2017173354 A2 | 10/2017 |
| WO | WO-2017173354 A3 | 10/2017 |

OTHER PUBLICATIONS

Afeyan et al., 2014, US 20140371302 A1.*
"International Application Serial No. PCT/US2017/025527, International Search Report dated Jan. 11, 2018", 7 pgs.
"International Application Serial No. PCT/US2017/025527, Written Opinion dated Jan. 11, 2018", 7 pgs.
Anneke, Brummer, et al., "MicroRNA binding sites in the coding region of mRNAs Extending the repertoire of post-transcriptional gene regulation Problems & Paradigm", Bioessays, vol. 36 No. 6, (Jun. 1, 2014), 617-626.
Bin, Li, et al., "Effects of Chemically Modified Messenger RNA on Protein Expression", Bioconjugate Chemistry, vol. 27 No. 3, (Mar. 16, 2016), 849-853.
Crowley, Samuel T., et al., "Efficient Expression of mRNA PEG-Peptide Polyplexes in Mouse Liver", (2015), 2 pgs.
Ginn, S. L., et al., "Gene therapy clinical trials worldwide to 2012—an update.", J Gene Med, 15(2), (2013), 65-77.
Kahn, Jeffrey S., et al., "Recombinant vesicular stomatitis virus expressing respiratory syncytial virus (RSV) glycoproteins: RSV fusion protein can mediate infection and cell fusion", Virology 254.1, (1999), 81-91.
Karpala, A J, et al., "Imune responses to dsRNA Implications for gene silencing technology", Immunology and Cell Bio, Carlton AU, vol. 83 No. 3, (Jun. 1, 2005), 211-216.
Liu, et al., "Structural Basis of Toll-Like Receptor 3 Signaling with Double-Stranded RNA", Science, vol. 320, (Apr. 18, 2008), 379-381.
M, Caskey, et al., "Synthetic double-stranded RNA induces innate ininune responses similar to a live viral vaccine in humans", The Journal of Immunology, vol. 181 No. 1, (Nov. 7, 2011), 276-2366.
Sahin, Ugur, et al., "mRNA-based therapeutics—developing a new class of drugs", Nature reviews Drug discovery 13.10, (2014), 759-780.
Takahashi, Kazutoshi, et al., "Induction of pluripotent stem cells from mouse embryonic and adult fibroblast cultures by defined factors", cell 126.4, (2006), 633-676.
Tatyana, O Kabilova, et al., "Imunotherapy of hepatocellular carcinoma with small double-stranded RNA", BMC Cancer Biomed Central London GB, vol. 14 No. 1, (May 18, 2014), 338.
Weide, Benjamin, et al., "Direct injection of protamine-protected mRNA: results of a phase 1/2 vaccination trial in metastatic melanoma patients", Journal of Immunotherapy 32.5, (2009), 498-507.
Zhou, Hongyan, et al., "Generation of induced pluripotent stem cells using recombinant proteins", Cell stem cell 4.5, (2009), 381.
"International Application Serial No. PCT/US2017/025527, International Preliminary Report on Patentability dated Oct. 11, 2018", 9 pgs.
Poliskey, Jacob, et al., "Development of Stabilized mRNA Nanoparticles for In Vivo Gene Delivery (Poster)", University of Iowa Center for Biocatalysisand Biotechnology., (2015), 1 pg.

* cited by examiner

*Primary Examiner* — Shin Lin Chen
(74) *Attorney, Agent, or Firm* — Schwegman Lundberg & Woessner, P.A.

(57) ABSTRACT

Double stranded mRNA (ds mRNA), e.g., produced in vitro, where one strand encodes a protein of interest and the other strand is hydrogen bonded to at least a portion of the coding region for the protein, as well as methods of making and using the ds mRNA, are provided.

14 Claims, 10 Drawing Sheets

Specification includes a Sequence Listing.

METABOLICALLY STABILIZED DOUBLE STRANDED MRNA

CROSS-REFERENCE TO RELATED APPLICATIONS

This application is a U.S. National Stage Filing under 35 U.S.C. 371 from International Application No. PCT/US2017/025527, filed on Mar. 31, 2017, and published as WO 2017/173354 on Oct. 5, 2017, which application claims the benefit of the filing date of U.S. application Ser. No. 62/317,142, filed on Apr. 1, 2016, and U.S. application Ser. No. 62/335,186, filed on May 12, 2016, the disclosures of which are incorporated by reference herein.

STATEMENT OF GOVERNMENT RIGHTS

This invention was made with government support under contract GM097093, GM117785 and GM008365 awarded by the National Institutes of Health. The government has certain rights in the invention.

BACKGROUND

The development of a non-viral gene delivery system that efficiently expresses proteins in the liver has been a long-sought goal for over twenty-five years (Wu et al., 1988). Preclinical studies have demonstrated that protein expression in hepatocytes could lead to curative treatments for liver metabolic diseases as well as diseases in other organs (Wooddell et al., 2013; Chuah et al., 2013; Richard et al., 2009). Much of the effort in developing a non-viral gene delivery system for the liver has focused on packaging and targeting plasmid DNA (Pun et al., 2002; Lenter et al., 2004; Read et al., 2005). Despite much effort, systemic delivery of DNA formulations resulted in either negligible or very low gene transfer efficiency in liver hepatocytes (Hu et al., 2013). In contrast, hydrodynamic delivery of naked plasmid DNA to liver achieves expression efficiency equivalent to adenovirus or adeno-associated virus (AAV) (Liu et al., 1999). While hydrodynamic delivery is highly efficient because it overcomes the rate limiting step of delivery of DNA to the nucleus, it is also an invasive delivery method requiring both high volume and pressure (Al Dosari et al., 2005; Zhang et al., 2004; Andrianaivo at al., 2004; Hodges et al., 2003). Alternatively, the delivery of mRNA to the cytosol leading to translation, circumvents the need for delivery to the nucleus. Despite this major advantage, the rapid metabolism of mRNA by ubiquitous RNase remains a significant hurdle to achieving efficient expression of systemically delivered mRNA gene delivery systems (Sahin et al., 2014).

Since the earliest report demonstrating in vivo expression following intramuscularly (i.m.) dosed naked mRNA (Wolff et al., 1990), numerous studies have attempted to increase the stability and expression efficiency of mRNA formulations using cationic lipids (Deering et al., 2014; Phua et al., 2013; Schlake et al., 2012; Kariko et al, 2012; Malone et al., 1989). Intratracheal high pressure spraying of an mRNA Megafectin™ lipoplex resulted in transfection of the lung (Kormann et al., 2011), whereas regeneration following myocardial infarction was achieved by intracardial injection of RNAiMAX™ mRNA (Zangi et al., 2013). Stemfect™ mRNA delivered nasally resulted in tumor vaccination (Phua et al., 2014). Alternatively, systemically delivered Stemfect™ mRNA produced low level expression in the spleen (Phua et al., 2013). While these studies demonstrate that mRNA lipoplexes possess improved in vivo gene transfer over naked mRNA, their efficiency in vivo is still very low due to relatively weak ionic binding of cationic lipids to mRNA. A mannosylated histidinylated lipoplex dosed systemically resulted in expression in spleen macrophages which primed a tumor vaccine response (Perche et al., 2011).

In an attempt to further improve mRNA stability, nanoparticle delivery systems have been developed and tested in vitro (Avci-Adali et al., 2014; Cheng et al., 2012; Debus et al., 2010) and in vivo (Perche et al., 2011; Wang et al., 2013; Uchida et al., 2013). Systemic delivery of targeted stealth mRNA lipoplexes in vivo led to transfection efficiency similar to DNA formulations in solid tumor (Wang et al., 2013). Intrathecally dosed mRNA polyplex nanomicelles produced measurable expression in the cerebrospinal fluid (Uchida et al., 2013). Notably, none of the mRNA cationic lipid or nanoparticle formulations reported to date were able to transfect liver.

There have been only two reports of successful liver transfection with mRNA (McCaffrey et al., 2002; Wilber et al., 2006). The expression of mRNA in the liver was first achieved by McCaffrey et al. (2002) who measured luciferase expression by bioluminescence imaging (BLI) in mice following hydrodynamic (HD)-dosing of 50 µg of naked mRNA to detect low level expression ($10^6$ photons/sec/$cm^2$/steradian). The transient expression in the liver was only detectable at 3 hours and required the co-administration of 30 µg of decoy RNA and 400 units of RNase inhibitor. In an attempt to improve transfection efficiency, Wilber et al. (2006) refined the mRNA by inserting 5' and 3' *Xenopus laevis* β-globin untranslated regions (UTRs) flanking luciferase to increase mRNA cellular half-life (Malone et al., 1989). HD-dosing of 50 µg of UTR mRNA resulted in a 15-fold increase in the expression efficiency at 3 hours relative to mRNA lacking UTRs (Wilber et al., 2006) but failed to significantly extend the expression. Co-administration of decoy mRNA and RNase inhibitors significantly improved efficiency but failed to extend peak expression past 12 hours. While these reports demonstrate the feasibility of expressing proteins in the liver when HD-dosing mRNA, the efficiencies reported are far below that achievable with plasmid DNA due to mRNA's susceptibility to metabolism during delivery.

SUMMARY

As shown herein, double stranded (ds) mRNA is much more metabolically stable than single-stranded (ss) mRNA and so ds mRNA formulations as described herein, can be dosed intravenously and circulate in the blood. ds mRNA is also as efficiently translated into protein as single-stranded mRNA. Thus, ds mRNA that includes single-stranded mRNA may be employed in targeted gene delivery system, e.g., systemic delivery, to express therapeutic proteins in animals, e.g., humans. Persistent expression is achieved by self-amplifying mRNA constructs designed to replicate mRNA in the cytosol and extend its expression.

In particular, as described below, the expression efficiency in liver following hydrodynamic delivery of in vitro transcribed ds mRNA was improved using an exemplary codon-optimized mRNA luciferase construct with flanking 3' and 5' human β-globin untranslated regions (UTR mRNA) over an un-optimized mRNA without β-globin UTRs.

In one embodiment, the disclosure provides isolated double stranded (ds) mRNA encoding a protein of interest, which ds mRNA is highly stable to degradation, e.g., after treatment with RNase or incubation in serum. At least one strand of the ds mRNA has a 5' cap, a start codon, and a polyA sequence, and this strand encodes a protein. The two strands of the ds mRNA are hydrogen bonded (Watson Crick) over at least 10 nucleotides and up to the full length of the shortest strand, if the strands are of different lengths. For example, the two strands of the ds mRNA are hydrogen bonded over at least 25, 50, 100, 200, 500, 1000, 2000 or more, e.g., 10,000 nucleotides (or any integer between 25 and 10,000), or over at least 50%, 60%, 70%, 80%, 85%, 90%, 95%, 98% or more of the length of at least one strand. In one embodiment, at least one strand may include one or more non-natural nucleotides, e.g., a nucleotide that has a non-natural sugar, a non-natural nucleotide base, a non-phosphodiester bond between nucleotides, or any combination thereof. In one embodiment, at least one of the strands may be formed using one or more of 2'-fluoro-2'deoxycytidine-5'-triphosphate, 5-iodocytidine-5'-triphosphate, 5-methylcytidine-5'-triphosphate, 2'-O-methylcytidine-5'-triphosphate, 2'-amino-2'-deoxycytidine-5'-triphosphate, 2'-amino-2'-deoxycytidine-5'-triphosphate, 2'-azido-2'-deoxycytidine-5'-triphosphate, aracytidine-5'-triphosphate, 2-thiocytidine-5'-triphosphate, 6-azacytidine-5'-triphosphate, 5-bromocytidine-5'-triphosphate, 3'-O-methylcytidine-5'-triphosphate, 5-aminoallylcytidine-5'-triphosphate, pseudoisocytidine-5'-triphosphate, $N^4$-methylcytidine-5'-triphosphate, 5-carboxycytidine-5'-triphosphate, 5-formylcytidine-5'-triphosphate, 5-hydroxymethylcytidine-5'-triphosphate, 5-hydroxycytidine-5'-triphosphate, 5-methoxycytidine-5'-triphosphate, thienocytidine-5'-triphosphate, cytidine-5'-triphosphate, 3'-deoxycytidine-5'-triphosphate, biotin-16-aminoallylcytidine-5'-triphosphate, cyanine 3-aminoallylcytidine-5'-triphosphate, cyanine 5-aminoallylcytidine-5'-triphosphate or cytidine-5'-O-(1-thiotriphosphate). In one embodiment, at least one of the strands is formed using one or more of 2'-fluoro-2'-deoxyuridine-5'-triphosphate, 5-iodouridine-5'-triphosphate, 2'-O-methyluridine-5'-triphosphate, pseudouridine-5'-triphosphate, 5-methyluridine-5'-triphosphate, 4-thiouridine-5'-triphosphate, 2'-amino-2'-deoxyuridine-5'-triphosphate, 2'-azido-2'-deoxyuridine-5'-triphosphate, 2-thiouridine-5'-triphosphate, arauridine-5'-triphosphate, 5,6-dihydrouridine-5'-triphosphate, 6-azauridine-5'-triphosphate, 2'-O-methylpseudouridine-5'-triphosphate, 2'-O-methyl-5-methyluridine-5'-triphosphate, 5-bromouridine-5'-triphosphate, 3'-O-methyluridine-5'-triphosphate, 5-aminoallyluridine-5'-triphosphate. $N^1$-methylpseudouridine-5'-triphosphate, 5,6-dihydro-5-methyluridine-5'-triphosphate, 5-hydroxymethyluridine-5'-triphosphate, 5-formyluridine-5'-triphosphate, 5-carboxyuridine-5'-triphosphate, 5-hydroxyuridine-5'-triphosphate, 5-methoxyuridine-5'-triphosphate, thienouridine-5'-triphosphate, 5-carboxymethylesteruridine-5'-triphosphate, uridine-5'-triphosphate, 3'-deoxy-5-methyluridine-5'-triphosphate, 3'-deoxyundine-5'-triphosphate, biotin-16-aminoallyluridine-5'-triphosphate, desthiobiotin-16-aminoallyl-uridine-5'-triphosphate, cyanine 3-aminoallyluridine-5'-triphosphate, cyanine 7-aminoallyluridine-5'-triphosphate or uridine-5'-O-(1-thiotriphosphate). In one embodiment, at least one of the strands is formed using one or more of 5-aminoallyl-CTP, 2-amino-ATP, 5-Br-UTP, 5-carboxy-CTP, 5-carboxy-UTP, 5-carboxymethyest-UTP, 7-deaza-ATP, 5-formyl-CTP, 5-formyl-UTP, 5-hydroxy-CTP, 5-hydroxy-UTP, 5-hydroxymethyl-CTP, 5-hydroxymethyl-UTP, 5-iodo-UTP, 5-methoxy-CTP, 5-methoxy-UTP, N6-methyl-amino-ATP, N6-methyl-ATP, 5-methyl-CTP, pseudo-UTP, thieno-CTP, thieno-GTP, 1-thio-ATP or 2-thio-UTP. In one embodiment, one of the strands includes 5-formyl cytidine or pseudouridine. In one embodiment, at least 5%, 10%, 20%, 30%, 40%, 50% 60%, 70%, 80%, 90% or more of the nucleotides are non-natural nucleotides, and in one embodiment, the strands are hydrogen bonded over at least 5%, 10%, 20%, 30%, 40%, 50%, 60%, 70%, 80%, 90%, or more of the length of the strands.

Further provided is a method to prevent, inhibit or treat a disorder in a mammal associated with an absence or deficiency in a protein or in a mammal in need of increased amounts of a protein. The method includes systemically administering to the mammal an effective amount of a composition comprising one or more distinct ds mRNA as described above. In one embodiment, the composition is employed to express human factor VIII (HFVIII) in liver hepatocytes for treating hemophilia A. In one embodiment, the composition may be employed to systemically deliver CRISPR Cas9 or other gene editing systems.

Also provided are methods of making a ds mRNA encoding a protein of interest. In one embodiment, a strand of mRNA having a 5' cap, a start codon, a polyA sequence and an open reading frame for the protein and a strand of RNA that has sequence complementarity with the mRNA over at least 10 nucleotides are provided. The mRNA and the RNA with sequence complementarity are allowed to hydrogen bond, thereby providing the ds mRNA. In one embodiment, the strands are provided by transcription of one or more vectors, e.g. a plasmid vector. In one embodiment, the strands are provided by transcription of a single vector that includes an open reading frame for the protein that is flanked by a first promoter positioned to express the strand of mRNA and a second promoter positioned to express the strand of RNA with sequence complementarity. In one embodiment, at least one of the strands includes one or more non-natural nucleotides or nucleotide modifications. In one embodiment, the one or more nucleotide modifications are introduced post-synthesis of at least one of the strands. In one embodiment, the one or more non-natural nucleotides are incorporated during synthesis of at least one of the strands. In one embodiment, the strands are hydrogen bonded over at least 90% of the length of the strands. In one embodiment, the strands are hydrogen bonded over the entire length of the strands. In one embodiment, wherein the strands are not the same length. For example, when hybridized, the 3' end of the RNA with sequence complementarity overhands the 5' end of the strand of mRNA, or the the 3' end of the RNA with sequence complementarity is recessed relative to the 5' end of the strand of mRNA. In one embodiment, the strands are the same length. In one embodiment, at least one of the strands is synthesized in an in vitro transcription reaction. In one embodiment, at least one of the strands is synthesized in a cell.

Further provided is a method of using the ds mRNA, e.g., to express a protein of interest. In one embodiment, a composition comprising a ds mRNA encoding the protein of interest, wherein at least one strand of the ds mRNA has a 5' cap, a start codon, a polyA sequence and encodes the protein, wherein the two strands of the ds mRNA are hydrogen bonded over at least 10 nucleotides is provided and the composition is introduced to cells in an amount effective to express the protein. In one embodiment, the cells are in a mammal for example, the composition is systemically administered to the mammal. In one embodiment, the composition is locally administered to the mammal. In one embodiment, the protein is a therapeutic protein. In one embodiment, the protein is for cancer immunotherapy. In one embodiment, the protein is a cancer antigen. In one embodiment, the protein is a nuclease. In one embodiment, the protein is a microbial protein, for instance, one useful for immunization. In one embodiment, the composition further comprises a carrier protein. In one embodiment, the composition further comprises a synthetic polymer optionally in combination with a carrier protein. In one embodiment, the composition further comprises a liposome. In one embodiment, the ds mRNA forms a nanoparticle, e.g., optionally in combination with a carrier protein, lipid, such as a lipid bilayer surrounding the ds mRNA, or synthetic polymer. In one embodiment, the nanoparticle has a diameter of about 1 nm to about 500 nm, about 50 nm to about 250 nm, or about 100 nm to about 200 nm. In one embodiment, the ds mRNA forms a microparticle, e.g., optionally in combination with a carrier protein, lipid, such as a lipid bilayer surrounding the ds mRNA, or synthetic polymer. In one embodiment, the microparticle has a diameter of about 0.5 μm to about 500 μm, about 10 μm to about 30 μm, or about 20 μm to about 40 μm.

DETAILED DESCRIPTION

Figure 1:
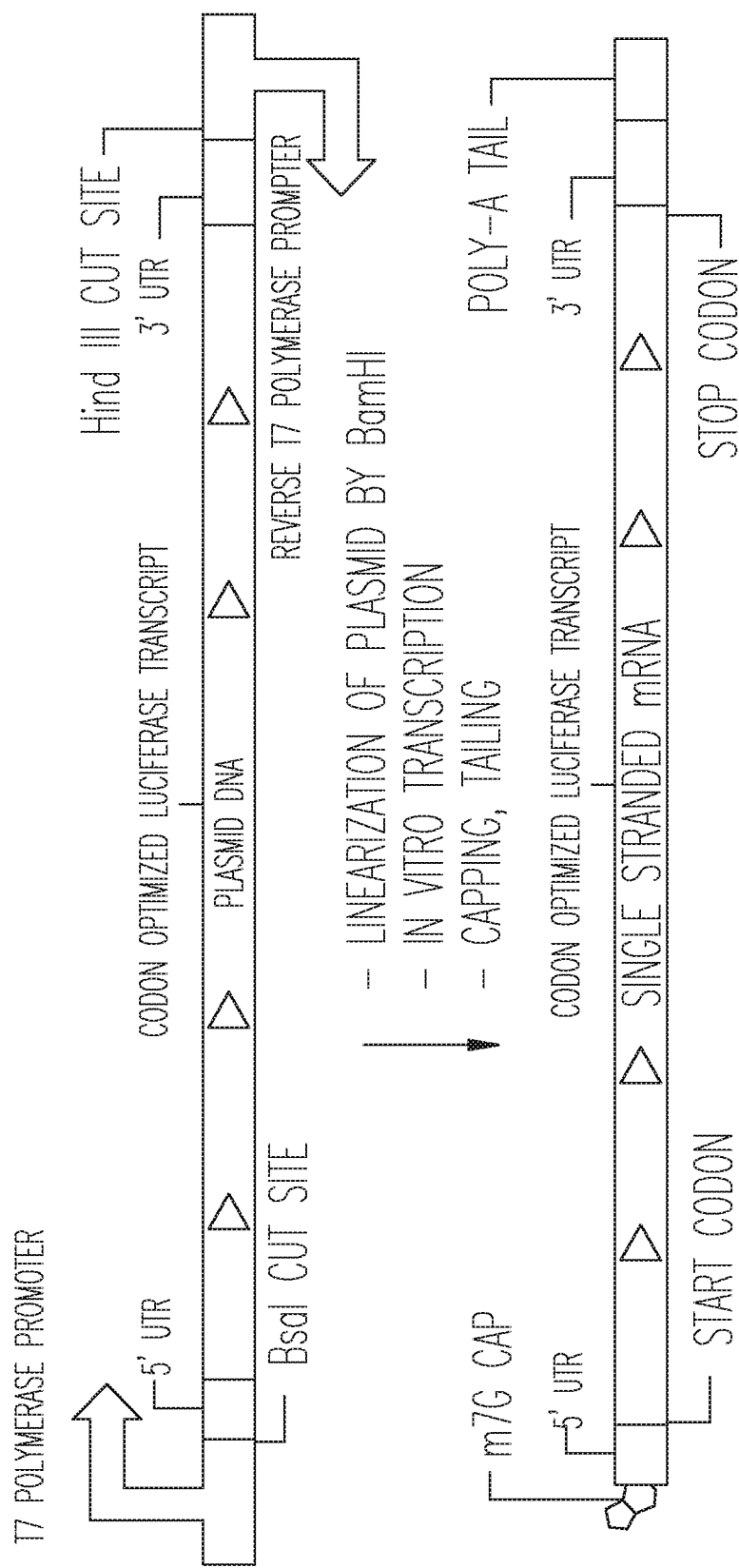
FIG. 1. Schematic of exemplary vector for single-stranded mRNA expression.

Various non-viral vectors can be used to deliver DNA, mRNA and short double-stranded RNA, including small interfering RNA (siRNA) and microRNA (miRNA) mimics. However, delivery of double stranded RNA (not mRNA, siRNA or miRNA) is highly toxic to cells due to triggering of apoptosis. Moreover, in order to be useful for gene therapy, the vectors need to avoid degradation by serum endonucleases and evade immune detection. They also need to avoid renal clearance from the blood and prevent non-specific interactions.

A stabilized ds mRNA containing composition is disclosed herein that is useful for prophylactic or therapeutic gene delivery. The compositions may be employed in methods to prevent, inhibit or treat a disorder or disease in a mammal, such as a canine, feline, bovine, porcine, equine, caprine, ovine, or human, which disorder or disease is amenable to treatment with one or more exogenously delivered genes. For example, the disorder or disease may be associated with a decreased amount of a gene product, the absence of a gene product, or the presence of an aberrant gene product, e.g., one having no activity, aberrant activity, reduced activity or increased activity relative to a mammal without the disorder or disease.

Exemplary Disorders or Diseases for Use with the Compositions

The compositions may be employed to prevent, inhibit or treat a variety of disorders or diseases associated with a deficiency in (or absence of) a protein or an aberrant protein (e.g., with low or no activity or excessive or unregulated activity) (see Table 1 for a list of monogenic disorders). Genes that may be employed include but are not limited to those that prevent, inhibit or treat hemophilia, anemia or other blood disorders, cancer, cardiovascular disease, lysosomal storage diseases, musculoskeletal diseases, neurodegenerative diseases, respiratory disease, and the like. Exemplary genes are shown in Table 2.

TABLE 1

| Monogenic disorders | Cancer |
| --- | --- |
| Adrenoleukodystrophy | Gynaecological - breast, ovary, cervix, vulva |
| α-1 antitrypsin deficiency | Nervous system - glioblastoma, leptomeningeal carcinomatosis, glioma, astrocytoma, neuroblastoma, retinoblastoma |
| Becker muscular dystrophy | Gastrointestinal - colon, colorectal, liver metastases, post-hepatitis liver cancer, pancreas, gall bladder |
| β-thalassaemia | Genitourinary - prostate, renal, bladder, anogenital neoplasia |
| Canavan disease | Skin - melanoma (malignant/metastatic) |
| Chronic granulomatous disease | Head and neck - nasopharyngeal carcinoma, squamous cell carcinoma, oesophaegeal cancer |
| Cystic fibrosis | Lung - adenocarcinoma, small cell/nonsmall cell, mesothelioma |
| Duchenne muscular dystrophy | Haematological - leukaemia, lymphoma, multiple myeloma |
| Fabry disease | Sarcoma |
| Familial adenomatous polyposis | Germ cell |
| Familial hypercholesterolaemia | Li-Fraumeni syndrome |
| Fanconi anaemia | Thyroid |
| Galactosialidosis | Neurological diseases |
| Gaucher's disease | Alzheimer's disease |
| Gyrate atrophy | Amyotrophic lateral sclerosis |
| Haemophilia A and B | Carpal tunnel syndrome |
| Hurler syndrome | Cubital tunnel syndrome |

TABLE 1-continued

| | |
|---|---|
| Hunter syndrome | Diabetic neuropathy |
| Huntington's chorea | Epilepsy |
| Junctional epidermolysis bullosa | Multiple sclerosis |
| Late infantile neuronal ceroid lipofuscinosis | Myasthenia gravis |
| Leukocyte adherence defiency | Parkinson's disease |
| Limb girdle muscular dystrophy | Peripheral neuropathy |
| Lipoprotein lipase deficiency | Pain |
| Mucopolysaccharidosis type VII | Ocular diseases |
| Ornithine transcarbamylase deficiency | Age-related macular degeneration |
| Pompe disease | Diabetic macular edema |
| Purine nucleoside phosphorylase deficiency | Glaucoma |
| Recessive dystrophic epidermolysis bullosa | Retinitis pigmentosa |
| Sickle cell disease | Superficial corneal opacity |
| Severe combined immunodeficiency | Choroideraemia |
| Tay Sachs disease | Leber congenital amaurosis |
| Wiskott-Aldrich syndrome | Inflammatory diseases |
| Cardiovascular disease | Arthritis (rheumatoid, inflammatory, degenerative) |
| Anaemia of end stage renal disease | Degenerative joint disease |
| Angina pectoris (stable, unstable, refractory) | Degenerative joint disease |
| Coronary artery stenosis | Ulcerative colitis |
| Critical limb ischaemia | Severe inflammatory disease of the rectum |
| Heart failure | Other diseases |
| Intermittent claudication | Chronic renal disease |
| Myocardial ischaemia | Erectile dysfunction |
| Peripheral vascular disease | Detrusor overactivity |
| Pulmonary hypertension | Parotid salivary hypofunction |
| Venous ulcers | Oral mucositis |
| Infectious disease | Fractures |
| Adenovirus infection | Type I diabetes |
| Cytomegalovirus infection | Diabetic ulcer/foot ulcer |
| Epstein-Barr virus | Graft versus host disease/transplant patients |
| Hepatitis B and C | |
| HIV/AIDS | |
| Influenza | |
| Japanese encephalitis | |
| Malaria | |
| Paediatric respiratory disease | |
| Respiratory syncytial virus | |
| Tetanus | |
| Tuberculosis | |

TABLE 2

| Gene Symbol | Protein name | Related Diseases |
|---|---|---|
| BCL2L11 | BCL2-like 11 (apoptosis facilitator) | Cancer, e.g. human T-cell acute lymphoblastic leukemia and lymphoma |
| BRCA1 | breast cancer 1, early onset | Cancer, e.g. breast cancer, pancreatic cancer |
| F8 | coagulation factor VIII, procoagulant component | Hemophilia |
| FLI1 | Friend leukemia virus integration 1 | cancer, e.g. Ewing's sarcoma, and myelodysplasia |
| FMR1 | fragile X mental retardation 1 | Fragile X syndrome and premature ovarian failure |
| FNDC5 | fibronectin type III domain containing 5 | Obesity, Type 2 Diabetes |
| GCK | glucokinase (hexokinase 4) | Obesity, Type 2 Diabetes, and Hyperinsulinemic hypoglycemia |
| GLP1R | glucagon-like peptide 1 receptor | Type 2 Diabetes |
| GRN | granulin | autoimmune, inflammatory, dementia/CNS disease, cancer, e.g. hepatic cancer |
| HAMP | hepcidin antimicrobial peptide | hemochromatosis, thalassemia |
| HPRT1 | hypoxanthine phosphoribosyltransferase 1 | Lesch-Nyhan disease and HPRT-related gout |
| IDO1 | indoleamine 2,3-dioxygenase 1 | autoimmune and inflammatory diseases |
| IGF1 | insulin-like growth factor 1 (somatomedin C) | metabolic disease, delayed growth, cancer |
| IL10 | interleukin 10 | Autoimmune and inflammatory diseases, e.g. graft vs. host disease and rheumatoid arthritis |
| LDLR | low density lipoprotein receptor | dyslipidemias, atherosclerosis, and hypercholesterolemia |
| NANOG | Nanog homeobox | tissue regeneration |
| PTGS2 | prostaglandin-endoperoxide synthase 2 | inflammation, cancer, infectious disease |

TABLE 2-continued

| Gene Symbol | Protein name | Related Diseases |
| --- | --- | --- |
| | (prostaglandin G/H synthase and cyclooxygenase) | |
| RB1 | retinoblastoma 1 | cancer, e.g. bladder cancer, osteosarcoma, retinoblastoma, small cell lung cancer |
| SERPINF1 | serpin peptidase inhibitor, Glade F (alpha-2 antiplasmin, pigment epithelium derived factor), member 1 | cancer, choroidal neovascularization, cardiovascular disease, diabetes, and osteogenesis imperfecta |
| SIRT1 | sirtuin 1 | Metabolic disease, aging |
| SIRT6 | sirtuin 6 | antioxidative pathway, anti-NFkB |
| SMAD7 | SMAD family member 7 | Acute kidney injury (anti-TGFb), colorectal cancer |
| ST7 | suppression of tumorigenicity 7 | cancer, e.g. myeloid cancer, head and neck squamous cell carcinomas, breast cancer, colon carcinoma, and prostate cancer |
| STAT3 | signal transducer and activator of transcription 3 (acute-phase response factor) | tissue regeneration and Hyper-IgE recurrent infection syndrome |
| CFTR | Cystic fibrosis transmembrane conductance regulator | Cystic fibrosis (CF) and congenital bilateral absence of vas deferens (CBAVD) |
| PAH | Phenylalanine hydroxylase | Phenylketonuria (PKU) |
| CEP290 | Centrosomal protein of 290 kDa | Leber's congenital amaurosis (LCA), Bardet-Biedl syndrome (BBS), Joubert syndrome, Meckel syndrome, Sior-Loken syndrome |
| CD274 (also known as PD-L1) | cluster of differentiation 274 (also known as Programmed cell death 1 ligand 1) | Autoimmune disease, transplant rejection, allergies or asthma |
| ADIPOQ | adiponectin, C1Q and collagen domain containing (also known as adiponectin) | Obesity and obesity-linked diseases (e.g., hypertension, metabolic dysfunction, type 2 diabetes, atherosclerosis, and ischemic heart disease) |

Hemophilia-F8, F9, F11, VWF

Hemophilia is a group of hereditary genetic disorders that impair the body's ability to control blood clotting or coagulation, which is used to stop bleeding when a blood vessel is broken. Like most recessive sex-linked, X chromosome disorders, hemophilia is more likely to occur in males than females. For example, Hemophilia A (clotting factor VIII deficiency), the most common form of the disorder, is present in about 1 in 5,000-10,000 male births. Hemophilia B (factor IX deficiency) occurs in around 1 in about 20,000-34,000 male births. Hemophilia lowers blood plasma clotting factor levels of the coagulation factors, e.g. F8, needed for a normal clotting process. Thus when a blood vessel is injured, a temporary scab does form, but the missing coagulation factors prevent fibrin formation, which is necessary to maintain the blood dot. F8, for example, encodes Factor VIII (FVIII), an essential blood clotting protein. Factor VIII participates in blood coagulation; it is a cofactor for factor IXa which, in the presence of $Ca^{+2}$ and phospholipids forms a complex that converts factor X to the activated form Xa.

Aspects of the invention disclosed herein provide methods and compositions that are useful for upregulating F8 for the treatment and/or prevention of diseases associated with reduced F8 expression or function such as hemophilia. Aspects of the invention disclosed herein provide methods and compositions that are useful for upregulating F9 for the treatment and/or prevention of diseases associated with reduced F9 expression or function such as hemophilia. Aspects of the invention disclosed herein provide methods and compositions that are useful for upregulating F11 for the treatment and/or prevention of diseases associated with reduced F11 expression or function such as hemophilia. Aspects of the invention disclosed herein provide methods and compositions that are useful for upregulating VWF for the treatment and/or prevention of diseases associated with reduced VFW expression or function such as Von Willebrand's Disease Thus, in one embodiment, the compositions may be employed to prevent, inhibit or treat hemophilia including but not limited to hemophilia A, characterized by low levels of or the absence of factor 8 (Also called FVIII or factor VIII deficiency), hemophilia B, characterized by low levels of or the absence of factor 9 (Also called FIX or factor IX deficiency), hemophilia C, characterized by low levels of or the absence of factor 11 (Also called FXI or factor XI deficiency), or Von Willebrands Disease, characterized by a deficiency of a blood dotting protein Von Willebrand factor.

Lysosomal Storage Diseases

In one embodiment, the compositions may be employed to prevent, inhibit or treat a lysosomal storage disease. Lysosomal storage diseases include, but are not limited to, mucopolysaccharidosis (MPS) diseases, for instance, mucopolysaccharidosis type I, e.g., Hurler syndrome and the variants Scheie syndrome and Hurler-Scheie syndrome (a deficiency in alpha-L-iduronidase); Hunter syndrome (a deficiency of iduronate-2-sulfatase); mucopolysaccharidosis type III, e.g., Sanfilippo syndrome (A, B, C or D; a deficiency of heparan sulfate sulfatase, N-acetyl-alpha-D-glucosaminidase, acetyl CoA:alpha-glucosaminide N-acetyl transferase or N-acetylglucosamine-6-sulfate sulfatase); mucopolysaccharidosis type IV e.g., mucopolysaccharidosis type IV, e.g., Morquio syndrome (a deficiency of galactosamine-6-sulfate sulfatase or beta-galactosidase); mucopolysaccharidosis type VI, e.g., Maroteaux-Lamy syndrome (a deficiency of arylsulfatase B); mucopolysaccharidosis type II; mucopolysaccharidosis type III (A, B, C or D; a deficiency of heparan sulfate sulfatase, N-acetyl-alpha-D-glucosaminidase, acetyl CoA:alpha-glucosaminide N-acetyl transferase or N-acetylglucosamine-6-sulfate sulfatase); mucopolysaccharidosis type IV (A or B; a deficiency of galactosamine-6-sulfatase and beta-galatacosidase); mucopolysaccharidosis type VI (a deficiency of arylsulfatase B); mucopolysaccharidosis type VII (a deficiency in beta-glucuronidase); mucopolysaccharidosis type VIII (a deficiency of glucosamine-6-sulfate sulfatase); mucopolysaccharidosis type IX (a deficiency of hyaluronidase); Tay-Sachs disease (a deficiency in alpha subunit of beta-hexosaminidase); Sandhoff disease (a deficiency in both alpha and beta subunit of beta-hexosaminidase); GM1 gangliosidosis (type I or type II); Fabry disease (a deficiency in alpha galactosidase); metachromatic leukodystrophy (a deficiency of aryl sul-fatase A); Pompe disease (a deficiency of acid maltase);

fucosidosis (a deficiency of fucosidase); alpha-mannosidosis (a deficiency of alpha-mannosidase); beta-mannosidosis (a deficiency of beta-mannosidase), ceroid lipofuscinosis, and Gaucher disease (types I, II and III; a deficiency in glucocerebrosidase), as well as disorders such as Hermansky-Pudlak syndrome; Amaurotic idiocy; Tangier disease; aspartylglucosaminuria; congenital disorder of glycosylation, type Ia; Chediak-Higashi syndrome; macular dystrophy, corneal, 1; cystinosis, nephropathic; Fanconi-Bickel syndrome; Farber lipogranulomatosis; fibromatosis; geleophysic dysplasia; glycogen storage disease I; glycogen storage disease Ib; glycogen storage disease Ic; glycogen storage disease III; glycogen storage disease IV; glycogen storage disease V; glycogen storage disease VI; glycogen storage disease VII; glycogen storage disease 0; immunoosseous dysplasia, Schimke type; lipidosis; lipase b; mucolipidosis II, including the variant form; mucolipidosis IV; neuraminidase deficiency with beta-galactosidase deficiency; mucolipidosis I; Niemann-Pick disease (a deficiency of sphingomyelinase); Niemann-Pick disease without sphingomyelinase deficiency (a deficiency of a npc1 gene encoding a cholesterol metabolizing enzyme); Refsum disease; Sea-blue histiocyte disease; infantile sialic acid storage disorder; sialuria; multiple sulfatase deficiency; triglyceride storage disease with impaired long-chain fatty acid oxidation; Winchester disease; Wolman disease (a deficiency of cholesterol ester hydrolase); Deoxynbonuclease I-like 1 disorder, arylsulfatase E disorder; ATPase, H+ transporting, lysosomal, subunit 1 disorder; glycogen storage disease IIb; Ras-associated protein rab9 disorder; chondrodysplasia punctata 1, X-linked recessive disorder; glycogen storage disease VIII; lysosome-associated membrane protein 2 disorder; Menkes syndrome; congenital disorder of glycosylation, type Ic; and sialuria.

Cancer-SERPINF1, BCL2L11, BRCA1, RB1, ST7

In one embodiment, the compositions may be employed to prevent, inhibit or treat cancer. Cancer is a broad group of various diseases, all involving unregulated cell growth. In cancer, cells divide and grow uncontrollably, forming malignant tumors, and invade nearby parts of the body. Several genes, many classified as tumor suppressors, are downregulated during cancer progression, e.g., SERPINF1, BCL2L11, BRCA1, RB1, and ST7, and have roles in inhibiting genomic instability, metabolic processes, immune response, cell growth/cell cycle progression, migration, and/or survival. These cellular processes are important for blocking tumor progression. SERPINF1 encodes an anti-angiogenic factor. BCL2L11 encodes an apoptosis facilitator. BRCA1 encodes a RING finger protein involved in DNA damage repair. RB1 prevents excessive cell growth by inhibiting cell cycle progression until a cell is ready to divide. ST7 suppresses tumor growth in mouse models and is involved in regulation of genes involved in differentiation. Aspects of the invention disclosed herein provide methods and compositions that are useful for upregulating SERPINF1, BCL2L11, BRCA1, RB1, and ST7 for the treatment and/or prevention of diseases associated with reduced SERPINF1. BCL2L11, BRCA1, RB1, and ST7 expression or function such as cancer. For example, aspects of the invention disclosed herein provide methods and compositions that are useful for upregulating BCL2L11 for the treatment or prevention of human T-cell acute lymphoblastic leukemia and lymphoma. In another example, aspects of the invention disclosed herein provide methods and compositions that are useful for upregulating BRCA1 for the treatment or prevention of breast cancer or pancreatic cancer. In another example, aspects of the invention disclosed herein provide methods and compositions that are useful for upregulating RB1 for the treatment or prevention of bladder cancer, osteosarcoma, retinoblastoma, or small cell lung cancer. In another example, aspects of the invention disclosed herein provide methods and compositions that are useful for upregulating ST7 for the treatment or prevention of myeloid cancer, head and neck squamous cell carcinomas, breast cancer, colon carcinoma, or prostate cancer.

Examples of cancer include but are not limited to leukemias, lymphomas, myelomas, carcinomas, metastatic carcinomas, sarcomas, adenomas, nervous system cancers and genito-urinary cancers. In some embodiments, the cancer is adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, osteosarcoma, fibrous histiocytoma, brain cancer, brain stem glioma, cerebellar astrocytoma, malignant glioma, ependymoma, medulloblastoma, supratentorial primitive neuroectodermal tumors, hypothalamic glioma, breast cancer, male breast cancer, bronchial adenomas. Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinemia, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, or Wilms tumor.

Fragile X Syndrome-FMR1

Fragile X syndrome (FXS) (also known as Martin-Bell syndrome, or Escalante's syndrome) is a genetic syndrome that is the most common known single-gene cause of autism and the most common inherited cause of intellectual disability. It results in a spectrum of intellectual disability ranging from mild to severe as well as physical characteristics such as an elongated face, large or protruding ears, and larger testes (macroorchidism), behavioral characteristics such as stereotypical movements (e.g. hand-flapping), and social anxiety. Fragile X syndrome is associated with the expansion of the CGG trinucleotide repeat affecting the Fragile X mental retardation 1 (FMR1) gene on the X chromosome, resulting reduced expression of the X mental retardation protein (FMRP), which is required for normal neural development. Aspects of the invention disclosed herein provide methods and compositions that are useful for upregulating FMR1 for the treatment and/or prevention of diseases associated with reduced FMR1 expression or function such as Fragile X syndrome.

Premature Ovarian Failure—FMR1

Premature Ovarian Failure (POF), also known as premature ovarian insufficiency, primary ovarian insufficiency, premature menopause, or hypergonadotropic hypogonadism, is the loss of function of the ovaries before age 40. POF can be associated mutations in the Fragile X mental retardation 1 (FMR1) gene on the X chromosome, resulting reduced expression of the X mental retardation protein (FMRP). Aspects of the invention disclosed herein provide methods and compositions that are useful for upregulating FMR1 for the treatment and/or prevention of diseases associated with reduced FMR1 expression or function such as Premature Ovarian Failure.

Obesity—FNDC5, GCK, ADIPOQ

Obesity is a medical condition in which excess body fat has accumulated to the extent that it may have an adverse effect on health, leading to reduced life expectancy and/or increased health problems. A person is considered obese when his or her weight is 20% or more above normal weight. The most common measure of obesity is the body mass index or BMI. A person is considered overweight if his or her BMI is between 25 and 29.9; a person is considered obese if his or her BMI is over 30. Obesity increases the likelihood of various diseases, particularly heart disease, type 2 diabetes, obstructive sleep apnea, certain types of cancer, and osteoarthritis. Obesity is most commonly caused by a combination of excessive food energy intake, lack of physical activity, and genetic susceptibility. Overexpression of FNDC5, fibronectin type II containing 5, has been shown in animal models to reduce body weight in obese mice. GCK, glucokinase (hexokinase 4), phosphorylates glucose to produce glucose-6-phosphate, the first step in most glucose metabolism pathways. Mutations in the GCK gene have been found to be associated with obesity in humans. Aspects of the invention disclosed herein provide methods and compositions that are useful for upregulating FNDC5 for the treatment and/or prevention of diseases associated with reduced FNDC5 expression or function such as obesity. Aspects of the invention disclosed herein provide methods and compositions that are useful for upregulating GCK for the treatment and/or prevention of diseases associated with reduced GCK expression or function such as obesity.

Adiponectin, encoded by the ADIPOQ gene, is a hormone that regulates metabolism of lipids and glucose. Adipocytes found in adipose tissue secrete adiponectin into the bloodstream where it self-associates into larger structures by binding of multiple adiponectin trimers to form hexamers and dodecamers. Adiponectin levels are inversely related to the amount of body fat in an individual and positively associated with insulin sensitivity both in healthy subjects and in diabetic patients. Adiponectin has a variety of protective properties against obesity-linked complications, such as hypertension, metabolic dysfunction, type 2 diabetes, atherosclerosis, and ischemic heart disease through its anti-inflammatory and anti-atherogenic properties. Specifically with regard to type 2 diabetes, administration of adiponectin has been accompanied by a reduction in plasma glucose and an increase in insulin sensitivity. Aspects of the invention disclosed herein provide methods and compositions that are useful for upregulating ADIPOQ for the treatment and/or prevention of diseases associated with reduced ADIPOQ expression or function such as obesity or an obesity-linked disease or disorders such as hypertension, metabolic dysfunction, type 2 diabetes, atherosclerosis, and ischemic heart disease.

Type 2 Diabetes—FNDC5, GCK, GLP1R, SIRT1, ADIPOQ

Type 2 diabetes (also called Diabetes mellitus type 2 and formally known as adult-onset diabetes) a metabolic disorder that is characterized by high blood glucose in the context of insulin resistance and relative insulin deficiency. Type 2 diabetes makes up about 90% of cases of diabetes with the other 10% due primarily to diabetes mellitus type 1 and gestational diabetes. Obesity is thought to be the primary cause of type 2 diabetes in people who are genetically predisposed to the disease. The prevalence of diabetes has increased dramatically in the last 50 years. As of 2010 there were approximately 285 million people with the disease compared to around 30 million in 1985. Overexpression of FNDC5, fibronectin type II containing 5, has been shown in animal models to improve their insulin sensitivity. GCK, glucokinase (hexokinase 4), phosphorylates glucose to produce glucose-6-phosphate, the first step in most glucose metabolism pathways. Mutations in the GCK gene are known to be associated with Type 2 Diabetes. Glucagon-like peptide 1 receptor (GLP1R) is known to be expressed in pancreatic beta cells. Activated GLP1R stimulates the adenylyl cyclase pathway which results in increased insulin synthesis and release of insulin. SIRT1 (Sirtuin 1, also known as NAD-dependent deacetylase sirtuin-1) is an enzyme that deacetylates proteins that contribute to cellular regulation. Sirtuin 1 is downregulated in cells that have high insulin resistance and inducing its expression increases insulin sensitivity, suggesting the molecule is associated with improving insulin sensitivity. Aspects of the invention disclosed herein provide methods and compositions that are useful for upregulating FNDC5 for the treatment and/or prevention of diseases associated with reduced FNDC5 expression or function such as Type 2 Diabetes. Aspects of the invention disclosed herein provide methods and compositions that are useful for upregulating GCK for the treatment and/or prevention of diseases associated with reduced GCK expression or function such as Type 2 Diabetes. Aspects of the invention disclosed herein provide methods and compositions that are useful for upregulating GLP1R for the treatment and/or prevention of diseases associated with reduced GLP1R expression or function such as Type 2 Diabetes. Aspects of the invention disclosed herein provide methods and compositions that are useful for upregulating SIRT1 for the treatment and/or prevention of diseases associated with reduced SIRT1 expression or function such as Type 2 Diabetes. Aspects of the invention disclosed herein provide methods and compositions that are useful for upregulating ADIPOQ for the treatment and/or prevention of diseases associated with reduced ADIPOQ expression or function such as Type 2 Diabetes.

Metabolic Disease—IGF1, SIRT1

Inborn errors of metabolism comprise a large class of genetic diseases involving disorders of metabolism. The majority are due to defects of single genes that code for enzymes that facilitate conversion of various substances (substrates) into others (products). In most of the disorders, problems arise due to accumulation of substances which are toxic or interfere with normal function, or to the effects of reduced ability to synthesize essential compounds. Inborn errors of metabolism are now often referred to as congenital metabolic diseases or inherited metabolic diseases. IGF-1. Insulin growth factor-1, is a hormone similar in molecular structure to insulin. IGF-1 plays an important role in childhood growth and continues to have anabolic effects in adults. Reduced IGF-1 and mutations in the IGF-1 gene are associated with metabolic disease. SIRT1 (Sirtuin 1, also known as NAD-dependent deacetylase sirtuin-1) is an enzyme that deacetylates proteins that contribute to cellular regulation. SIRT1 has been shown to de-acetylate and affect the activity of both members of the PGC1-alpha/ERR-alpha complex, which are essential metabolic regulatory transcription factors. Aspects of the invention disclosed herein provide methods and compositions that are useful for upregulating IGF-1 for the treatment and/or prevention of diseases associated with reduced IGF-1 expression or function such as metabolic disease. Aspects of the invention disclosed herein provide methods and compositions that are useful for upregulating SIRT1 for the treatment and/or prevention of diseases associated with reduced SIRT1 expression or function such as metabolic disease.

Aging/Senescence—SIRT1

Senescence is the state or process of aging. Cellular senescence is a phenomenon where isolated cells demonstrate a limited ability to divide in culture, while organismal senescence is the aging of organisms. After a period of near perfect renewal (in humans, between 20 and 35 years of age), organismal senescence/aging is characterised by the declining ability to respond to stress, increasing homeostatic imbalance and increased risk of disease. This currently irreversible series of changes inevitably ends in death. SIRT1 (Sirtuin 1, also known as NAD-dependent deacetylase sirtuin-1) is an enzyme that deacetylates proteins that contribute to cellular regulation. Mice overexpressing SIRT1 present lower levels of DNA damage, decreased expression of the ageing-associated gene p16Ink4a, a better general health and fewer spontaneous carcinomas and sarcomas. Aspects of the invention disclosed herein provide methods and compositions that are useful for upregulating SIRT1 for the treatment and/or prevention of biological processes associated with reduced SIRT1 expression or function such as aging.

Autoimmune—GRN, IDO1, CD274

Autoimmune diseases arise from an inappropriate immune response of the body against substances and tissues normally present in the body. In other words, the immune system mistakes some part of the body as a pathogen and attacks its own cells. Autoimmune diseases are classified by corresponding types of hypersensitivity: type II, type III, or type IV. Examples of autoimmune disease include, but are not limited to, Ankylosing Spondylitis, Autoimmune cardiomyopathy, Autoimmune hemolytic anemia, Autoimmune hepatitis, Autoimmune inner ear disease, immune lymphoproliferative syndrome, Autoimmune peripheral neuropathy, Autoimmune pancreatitis, Autoimmune polyendocrine syndrome, Autoimmune thrombocytopenic purpura, Celiac disease, Cold agglutinin disease, Contact dermatitis, Crohn's disease, Dermatomyositis, Diabetes mellitus type 1, Eosinophilic fasciitis, Gastrointestinal pemphigoid, Goodpasture's syndrome, Graves' disease, Guillain-Barré syndrome, Hashimoto's encephalopathy, Hashimoto's thyroiditis, Idiopathic thrombocytopenic purpura, Lupus erythematosus, Miller-Fisher syndrome, Myasthenia gravis, Pemphigus vulgaris, Pernicious anaemia, Polymyositis, Primary biliary cirrhosis, Psoriasis, Psoriatic arthritis, Relapsing polychondritis, Rheumatoid arthritis, Sjögren's syndrome, Temporal arteritis, Transverse myelitis, Ulcerative colitis, Undifferentiated connective tissue disease, Vasculitis, Vitiligo, and Wegener's granulomatosis. IDO1 encodes indoleamine 2,3-dioxygenase (IDO)—a heme enzyme that catalyzes the first and rate-limiting step in tryptophan catabolism to N-formylkynurenine. This enzyme acts on multiple tryptophan substrates including D-tryptophan, L-tryptophan, 5-hydroxytryptophan, tryptamine, and serotonin. This enzyme is thought to play a role in a variety of pathophysiological processes such as antimicrobial and antitumor defense, neuropathology, immunoregulation, and antioxidant activity. Increased catabolism of tryptophan by IDO1 suppresses T cell responses in a variety of diseases or states, including autoimmune disorders. GRN encodes a precursor protein called Progranulin, which is then cleaved to form the secreted protein granulin. Granulin regulates cell division, survival, motility and migration. Granulin has roles in cancer, inflammation, host defense, cartilage development and degeneration, and neurological functions. Downregulation of GRN has been shown to increase the onset of autoimmune diseases like rheumatoid arthritis. Aspects of the invention disclosed herein provide methods and compositions that are useful for upregulating IDO1 for the treatment and/or prevention of diseases associated with reduced IDO1 expression or function such as autoimmune diseases. Aspects of the invention disclosed herein provide methods and compositions that are useful for upregulating GRN for the treatment and/or prevention of diseases associated with reduced GRN expression or function such as autoimmune diseases.

CD274 (also known as PDL1) is a transmembrane protein containing IgV-like and IgC-like extracellular domains expressed on immune cells and non-hematopoietic cells, and is a ligand for the programmed death receptor (PD-1) expressed on lymphocytes and macrophages. PD-1 and CD274 interactions are essential in maintaining the balance of T-cell activation, tolerance, and immune-mediated tissue damage. CD274 is involved in inhibiting the initial phase of activation and expansion of self-reactive T cells, and restricting self-reactive T-cell effector function and target organ injury. More specifically, activation of PD-1 by CD274 inhibits T-cell proliferation, cytokine production, and cytolytic function by blocking the induction of phosphatidylinositol-3-kinase (PI3K) activity and downstream activation of Akt.

Decreased expression of CD274 results in autoimmunity in animal models. For example, mice deficient for the CD274 receptor, PD-1, developed features of late onset lupus. In another instance, blockade of CD274 activity in a mouse model of Type 1 diabetes resulted in accelerated progression of diabetes. In yet another example, CD274 blockade in an animal model of multiple sclerosis resulted in accelerated disease onset and progression.

Increasing expression of CD274 offers a novel approach for treating diseases related to inappropriate or undesirable activation of the immune system, including in the context of translation rejection, allergies, asthma and autoimmune disorders. Aspects of the invention disclosed herein provide methods and compositions that are useful for upregulating CD274 for the treatment and/or prevention of diseases associated with reduced CD274 expression or function such as autoimmune disease, transplant rejection, allergies or asthma.

Inflammation (Chronic Inflammation)—GRN, IDO1, IL10

Inflammation is part of the complex biological response of vascular tissues to harmful stimuli, such as pathogens, damaged cells, or irritants. Inflammation is a protective attempt by the organism to remove the injurious stimuli and to initiate the healing process. However, chronic inflammation can also lead to a host of diseases, such as hay fever, periodontitis, atherosclerosis, and rheumatoid arthritis. Prolonged inflammation, known as chronic inflammation, leads to a progressive shift in the type of cells present at the site of inflammation and is characterized by simultaneous destruction and healing of the tissue from the inflammatory process. Inflammatory disorder include, but are not limited to, acne vulgaris, asthma, autoimmune diseases, celiac disease, chronic prostatitis, glomerulonephritis, inflammatory bowel diseases, pelvic inflammatory disease, reperfusion injury, rheumatoid arthritis, sarcoidosis, transplantation rejection (graft vs host disease), vasculitis and interstitial cystitis.

GRN encodes a precursor protein called Progranulin, which is then cleaved to form the secreted protein granulin. Granulin regulates cell division, survival, motility and migration. Granulin has roles in cancer, inflammation, host defense, cartilage development and degeneration, and neurological functions. GRN has been shown to alleviate inflammatory arthritis symptoms in mouse models. Indoleamine 2,3-dioxygenase 1 (IDO1; previously referred as IDO or INDO) is the main inducible and rate-limiting enzyme for the catabolism of the amino acid tryptophan through the kynurenine pathway. Increased catabolism of tryptophan by IDO1 suppresses T cell responses in a variety of diseases, such as allograft rejection.

Aspects of the invention disclosed herein provide methods and compositions that are useful for upregulating GRN for the treatment and/or prevention of diseases associated with reduced GRN expression or function such as chronic inflammation. Aspects of the invention disclosed herein provide methods and compositions that are useful for upregulating GRN for the treatment and/or prevention of diseases associated with reduced GRN expression or function such as rheumatoid arthritis. Aspects of the invention disclosed herein provide methods and compositions that are useful for upregulating IDO1 for the treatment and/or prevention of diseases associated with reduced IDO1 expression or function such as chronic inflammation. Aspects of the invention disclosed herein provide methods and compositions that are useful for upregulating IDO1 for the treatment and/or prevention of diseases associated with reduced IDO1 expression or function such as graft vs. host disease.

IL-10 is capable of inhibiting synthesis of pro-inflammatory cytokines such as IFN-γ, IL-2, IL-3, TNFα and GM-CSF made by cells such as macrophages and regulatory T-cells. It also displays a potent ability to suppress the antigen-presentation capacity of antigen presenting cells. Treatment with IL-10 (e.g. as a recombinant protein given to patients) is currently in clinical trials for Crohn's disease. Genetic variation in the IL-10 pathway modulates severity of acute graft-versus-host disease. Mouse models of arthritis have been shown to have decreased levels of IL-10. Aspects of the invention disclosed herein provide methods and compositions that are useful for upregulating GRN for the treatment and/or prevention of diseases associated with reduced GRN expression or function such as chronic inflammation.

Aspects of the invention disclosed herein provide methods and compositions that are useful for upregulating IL-10 for the treatment and/or prevention of diseases associated with reduced IL-10 expression or function such as chronic inflammation. Aspects of the invention disclosed herein provide methods and compositions that are useful for upregulating IL-10 for the treatment and/or prevention of diseases associated with reduced IL-10 expression or function such as rheumatoid arthritis. Aspects of the invention disclosed herein provide methods and compositions that are useful for upregulating IL-10 for the treatment and/or prevention of diseases associated with reduced IL-10 expression or function such as graft vs host disease. Aspects of the invention disclosed herein provide methods and compositions that are useful for upregulating IL-10 for the treatment and/or prevention of diseases associated with reduced IL-10 expression or function such as Crohn's disease.

Infectious Disease—PTGS2

Infectious diseases, also known as transmissible diseases or communicable diseases comprise clinically evident illness (i.e., characteristic medical signs and/or symptoms of disease) resulting from the infection, presence and growth of pathogenic biological agents in an individual host organism. Infectious pathogens include some viruses, bacteria, fungi, protozoa, multicellular parasites, and aberrant proteins known as prions. A contagious disease is a subset of infectious disease that is especially infective or easily transmitted. Prostaglandin-endoperoxide synthase 2, also known as cyclooxygenase-2 or simply COX-2, is an enzyme that in humans is encoded by the PTGS2 gene. Prostaglandin endoperoxide H synthase, COX 2, converts arachidonic acid (AA) to prostaglandin endoperoxide H2. COX-2 is elevated during inflammation and infection. Aspects of the invention disclosed herein provide methods and compositions that are useful for upregulating PTGS2 for the treatment and/or prevention of diseases associated with reduced PTGS2 expression or function such as infectious disease.

CNS Disease—IGF1, GRN

Central nervous system (CNS) disease can affect either the spinal cord (myelopathy) or brain (encephalopathy), both of which are part of the central nervous system. CNS diseases include Encephalitis, Meningitis, Tropical spastic paraparesis, Arachnoid cysts, Amyotrophic lateral sclerosis, Huntington's disease, Alzheimer's disease, Dementia, Locked-in syndrome, Parkinson's disease, Tourette', and Multiple sclerosis. CNS diseases have a variety of causes including Trauma, Infections, Degeneration, Structural defects, Tumors, Autoimmune Disorders, and Stroke. Symptoms range from persistent headache, loss of feeling, memory loss, loss of muscle strength, tremors, seizures, slurred speech, and in some cases, death. IGF-1. Insulin growth factor-1, is a hormone similar in molecular structure to insulin. IGF-I deficiency is associated with neurodegenerative disease and has been shown to improve survival of neurons both in vitro and in vivo. Aspects of the invention disclosed herein provide methods and compositions that are useful for upregulating IGF1 for the treatment and/or prevention of diseases associated with reduced IGF1 expression or function such as CNS disease.

GRN encodes a precursor protein called Progranulin, which is then cleaved to form the secreted protein granulin. Granulin regulates cell division, survival, motility and migration. Granulin has roles in cancer, inflammation, host defense, cartilage development and degeneration, and neurological functions. Mutations in granulin are associated with dementia. Aspects of the invention disclosed herein provide methods and compositions that are useful for upregulating GRN for the treatment and/or prevention of diseases associated with reduced GRN expression or function such as CNS disease.

Hemochromatosis—HAMP

Hemochromatosis is the abnormal accumulation of iron in parenchymal organs, leading to organ toxicity. This is the most common inherited liver disease in Caucasians and the most common autosomal recessive genetic disorder. HAMP (hepcidin antimicrobial peptide) encodes the protein hepcidin, which plays a major role in maintaining iron balance in the body. Hepcidin circulates in the blood and inhibits iron absorption by the small intestine when the body's supply of iron is too high. Hepcidin interacts primarily with other proteins in the intestines, liver, and certain white blood cells to adjust iron absorption and storage. At least eight mutations in the HAMP-gene have been identified that result in reduced levels of hepcidin and hemochromatosis. Aspects of the invention disclosed herein provide methods and compositions that are useful for upregulating HAMP for the treatment and/or prevention of diseases associated with reduced HAMP expression or function such as hemochromatosis.

Acute Kidney Injury—SMAD7

Acute kidney injury (AKI), previously called acute renal failure (ARF), is a rapid loss of kidney function. Its causes are numerous and include low blood volume from any cause, exposure to substances harmful to the kidney, and obstruction of the urinary tract. AKI may lead to a number of complications, including metabolic acidosis, high potassium levels, uremia, changes in body fluid balance, and effects to other organ systems. SMAD7 (Mothers against decapentaplegic homolog 7) is a protein that, as its name describes, is a homolog of the *Drosophila* gene: "Mothers against decapentaplegic". It belongs to the SMAD family of proteins, which belong to the TGFβ superfamily of ligands. Like many other TGFβ family members, SMAD7 is involved in cell signalling. It is a TGFβ type 1 receptor antagonist. It blocks TGFβ1 and activin associated with the receptor, blocking access to SMAD2. It is an inhibitory SMAD (I-SMAD) and is enhanced by SMURF2. Upon TGF-β treatment, SMAD7 binds to discrete regions of Pellino-1 via distinct regions of the SMAD MH2 domains. The interaction block formation of the IRAK1-mediated IL-1R/TLR signaling complex therefore abrogates NF-κB activity, which subsequently causes reduced expression of pro-inflammatory genes. Overexpression of SMAD7 in the kidney using gene therapy inhibited renal fibrosis and inflammatory pathways. Aspects of the invention disclosed herein provide methods and compositions that are useful for upregulating SMAD7 for the treatment and/or prevention of diseases associated with reduced SMAD7 expression or function such as acute kidney injury.

Thalassemia—HAMP

Thalassemia is a group of inherited autosomal recessive blood disorders, resulting in a reduced rate of synthesis or no synthesis of one of the globin chains that make up hemoglobin. This can cause the formation of abnormal hemoglobin molecules or reduced numbers of hemoglobin, thus causing anemia, the characteristic presenting symptom of the thalassemias. HAMP (hepcidin antimicrobial peptide) encodes the protein hepcidin, which plays a major role in maintaining iron balance in the body. Hepcidin circulates in the blood and inhibits iron absorption by the small intestine when the body's supply of iron is too high. HAMP expression has been shown to be lower in patients with thalassemia and is associated with iron-overload (sometimes called hemochromatosis) in these patients. Aspects of the invention disclosed herein provide methods and compositions that are useful for upregulating HAMP for the treatment and/or prevention of diseases associated with reduced HAMP expression or function such as thalassemia.

Lesch-Nyhan Disease—HPRT1

Lesch-Nyhan syndrome (LNS), also known as Nyhan's syndrome, Kelley-Seegmiller syndrome and Juvenile gout, is a rare inherited disorder caused by a deficiency of the enzyme hypoxanthine-guanine phosphoribosyltransferase (HGPRT), produced by mutations in the HPRT gene located on the X chromosome. LNS affects about one in 380,000 live births. The HGPRT deficiency causes a build-up of uric acid in all body fluids. This results in both hyperuricemia and hyperuricosuria, associated with severe gout and kidney problems. Neurological signs include poor muscle control and moderate mental retardation. Aspects of the invention disclosed herein provide methods and compositions that are useful for upregulating HPRT for the treatment and/or prevention of diseases associated with reduced HPRT expression or function such as Lesch-Nyhan syndrome.

Delayed Growth—GF-1

Delayed growth is poor or abnormally slow height or weight gains in a child typically younger than age 5. IGF-1, Insulin growth factor-1, is a hormone similar in molecular structure to insulin. IGF-1 plays an important role in childhood growth and continues to have anabolic effects in adults. IGF1 deficiency has been shown to be associated with delayed growth and short stature in humans. Aspects of the invention disclosed herein provide methods and compositions that are useful for upregulating IGF1 for the treatment and/or prevention of diseases associated with reduced IGF1 expression or function such as delayed growth.

Dyslioidemias and Atherosclerosis—LDLR

Accumulation of lipids in the blood can cause a variety of conditions and diseases, e.g. dyslipidemia and atherosclerosis. Atherosclerosis in particular is the leading cause of death in industrialized societies, making prevention and treatment a high public health concern. Low-density lipoprotein (LDL) is a major transporter of fat molecules, e.g., cholesterol, in the blood stream that delivers fat molecules to cells. High-density lipoprotein (HDL) is another transporter of fat molecules that moves lipids, e.g. cholesterol, from cells to the liver. High levels of LDL are associated with health problems such as dyslipidemia and atherosclerosis, while HDL is protective against atherosclerosis and is involved in maintenance of cholesterol homeostasis.

Dyslipidemia generally describes a condition when an abnormal amount of lipids is present in the blood. Hyperlipidemia, which accounts for the majority of dyslipidemias, refers to an abnormally high amount of lipids in the blood. Hyperlipidemia is often associated with hormonal diseases such as diabetes, hypothyroidism, metabolic syndrome, and Cushing syndrome. Examples of common lipids in dyslipidemias include triglycerides, cholesterol and fat. Abnormal amounts lipids or lipoproteins in the blood can lead to atherosclerosis, heart disease, and stroke.

Atherosclerosic diseases, e.g. coronary artery disease (CAD) and myocardial infarction (MI), involve a thickening of artery walls caused by accumulation of fat in the blood, most commonly cholesterol. This thickening is thought to be the result of chronic inflammation of arteriole walls due to accumulation of LDLs in the vessel walls. LDL molecules can become oxidized once inside vessel walls, resulting in cell damage and recruitment of immune cells like macrophages to absorb the oxidized LDL. Once macrophages internalize oxidized LDL, they become saturated with cholesterol and are referred to as foam cells. Smooth muscle cells are then recruited and form a fibrous region. These processes eventually lead to formation of plaques that block arteries and can cause heart attack and stroke. HDL is capable of transporting cholesterol from foam cells to the liver, which aids in inhibition of inflammation and plaque formation.

The LDLR gene encodes the Low-Density Lipoprotein (LDL) Receptor, which is a mosaic protein of about 840 amino acids (after removal of signal peptide) that mediates the endocytosis of cholesterol-rich LDL. It is a cell-surface receptor that recognizes the apoprotein B 100 which is embedded in the phospholipid outer layer of LDL particles. LDL receptor complexes are present in clathrin-coated pits (or buds) on the cell surface, which when bound to LDL-cholesterol via adaptin, are pinched off to form clathrin-coated vesicles inside the cell. This allows LDL-cholesterol to be bound and internalized in a process known as endocytosis. This occurs in all nucleated cells (not erythrocytes), but mainly in the liver which removes about 70% of LDL from the circulation. Aspects of the invention disclosed herein provide methods and compositions that are useful for upregulating LDLR for the treatment and/or prevention of diseases associated with reduced LDLR expression or function such as dyslipidemia or atherosclerosis.

Tissue Regeneration—NANOG

Regeneration is the process of renewal, restoration, and growth of cells and organs in response to disturbance or damage. Strategies for regeneration of tissue include the rearrangement of pre-existing tissue, the use of adult somatic stem cells and the dedifferentiation and/or transdifferentiation of cells, and more than one mode can operate in different tissues of the same animal. During the developmental process, genes are activated that serve to modify the properties of cells as they differentiate into different tissues. Development and regeneration involves the coordination and organization of populations cells into a blastema, which is a mound of stem cells from which regeneration begins. Dedifferentiation of cells means that they lose their tissue-specific characteristics as tissues remodel during the regeneration process. Transdifferentiation of cells occurs when they lose their tissue-specific characteristics during the regeneration process, and then re-differentiate to a different kind of cell. These strategies result in the re-establishment of appropriate tissue polarity, structure and form. NANOG is a transcription factor critically involved with self-renewal of undifferentiated embryonic stem cells through maintenance of pluripotency. Aspects of the invention disclosed herein provide methods and compositions that are useful for upregulating NANOG for tissue regeneration.

Oxidative Stress/Antioxidative Pathway—SIRT6

Cells are protected against oxidative stress by an interacting network of antioxidant enzymes. Oxidation reactions can produce superoxides or free radicals. In turn, these radicals can start chain reactions. When the chain reaction occurs in a cell, it can cause damage or death to the cell. Antioxidants terminate these chain reactions by removing free radical intermediates, and inhibit other oxidation reactions. The superoxide released by processes such as oxidative phosphorylation is first converted to hydrogen peroxide and then further reduced to give water. This detoxification pathway is the result of multiple enzymes, with superoxide dismutases catalysing the first step and then catalases and various peroxidases removing hydrogen peroxide. As oxidative stress appears to be an important part of many human diseases, the use of antioxidants in pharmacology is highly attractive. Mono-ADP-ribosyltransferase sirtuin-6 is an enzyme that in humans is encoded by the SIRT6 gene. Sirtuin-6 has been shown to have a protective role against metabolic damage caused by a high fat diet. SIRT6 deficiency is associated with metabolic defects that lead to oxidative stress. Aspects of the invention disclosed herein provide methods and compositions that are useful for upregulating SIRT6 for tissue regeneration. Aspects of the invention disclosed herein provide methods and compositions that are useful for upregulating SIRT6 for the treatment and/or prevention of diseases associated with reduced SIRT6 expression or function such as oxidative stress.

Choroidal Neovascularization—SERPINF1

Choroidal neovascularization (CNV) is the creation of new blood vessels in the choroid layer of the eye. This is a common symptom of the degenerative maculopathy wet AMD (age-related macular degeneration). Serpin F1 (SERPINF1), also known as Pigment epithelium-derived factor (PEDF), is a multifunctional secreted protein that has anti-angiogenic, anti-tumorigenic, and neurotrophic functions. The anti-angiogenic properties of SERPINF1 allow it to block new blood vessel formation. Aspects of the invention disclosed herein provide methods and compositions that are useful for upregulating SERPINF1 for the treatment and/or prevention of diseases associated with reduced SERPINF1 expression or function such as Choroidal neovascularization.

Cardiovascular Disease—SERPINF1

Cardiovascular disease is a class of diseases that involve the heart or blood vessels (arteries and veins). Cardiovascular diseases remain the biggest cause of deaths worldwide. Types of cardiovascular disease include, Coronary heart disease, Cardiomyopathy. Hypertensive heart disease. Heart failure, Corpulmonale. Cardiac dysrhythmias, Inflammatory heart disease, Valvular heart disease, Stroke and Peripheral arterial disease. Serpin F1 (SERPINF1), also known as Pigment epithelium-derived factor (PEDF), is a multifunctional secreted protein that has anti-angiogenic, anti-tumorigenic, and neurotrophic functions. SERPINF1 has been shown to have a protective role in atherosclerosis, the main cause of coronary heart disease, myocardial infarction and heart failure due to its anti-inflammatory, antioxidant and antithrombotic effects in the vessel wall and platelets. Additionally SERPINF1 has strong antiangiogenic effects by inducing apoptosis in endothelial cells and by regulating the expression of other angiogenic factors. Aspects of the invention disclosed herein provide methods and compositions that are useful for upregulating SERPINF1 for the treatment and/or prevention of diseases associated with reduced SERPINF1 expression or function such as cardiovascular disease.

Hyperimmunoglobulin E Syndrome—STAT3

Loss-of-function mutations in the STAT3 gene result in Hyperimmunoglobulin E syndrome, associated with recurrent infections as well as disordered bone and tooth development.

Leber's Congenital Amaurosis (LCA), Bardet-Biedl Syndrome (BBS), Joubert Syndrome, Meckel Syndrome, Sior-Loken Syndrome—CEP290

Leber's congenital amaurosis (LCA) is a rare autosomal recessive eye disease resulting in a severe form of retinal dystrophy that is present from birth. LCA results in slow or non-existent pupillary responses, involuntary eye movement, and severe loss of vision. LCA is thought to be caused by abnormal photoreceptor cell development or degeneration. Bardet-Biedl syndrome (BBS) is characterized by retinal dystrophy and retinitis pigmentosa. Other manifestations include polydactyly and renal abnormalities. Both LCA and BBS are associated with mutations in Centrosomal protein 290 kDA (CEP290).

CEP290 is a large coiled-coil protein found in the centrosome and cilia of cells. CEP290 modulates ciliary formation and is involved in trafficking ciliary proteins between the cell body and the cilium of a cell. Reduction or abolishment of CEP290 activity, results in retinal and photoreceptor degeneration. This generation is thought to be the result of defects in ciliogenesis. CEP290 is also associated with Joubert syndrome, Meckel syndrome, and Sior-Loken syndrome. Aspects of the invention disclosed herein provide methods and compositions that are useful for upregulating CEP290 for the treatment and/or prevention of diseases associated with reduced CEP290 expression or function such as Leber's congenital amaurosis (LCA), Bardet-Biedl syndrome (BBS), Joubert syndrome, Meckel syndrome, Sior-Loken syndrome.

Phenylketonuria—PAH

Phenylketonuria (PKU) is an autosomal recessive metabolic disease caused by elevated levels of Phenylalanine (Phe) in the blood. Phe is a large neutral amino acid (LNAA) that interacts with the LNAA transporter in order to cross the blood-brain barrier. When Phe is in excess in the blood, it saturates the LNAA transporter, prevent other essential LNAAs from crossing the blood-brain barrier. This results in depletion of these amino acids in the brain, leading to slowing of the development of the brain and mental retardation. PKU can be managed by strictly controlling and monitoring Phe levels in the diet in infants and children. However, if left untreated, severe mental retardation, irregular motor functions, and behavioral disorders result from Phe accumulation in the blood.

Phe accumulation in the blood is the result of mutations in the Phenylalanine hydroxylase (PAH) gene, which encodes phenylalanine hydroxylase protein. Phenylalanine hydroxylase is an enzyme that generates tyrosine through hydroxylation of the aromatic side-chain of Phe. Phenylalanine hydroxylase is the rate-limiting enzyme in the degradation of excess Phe. When phenylalanine hydroxylase levels are decreased or enzyme functionality is compromised, Phe begins to accumulate in the blood, resulting in PKU. Aspects of the invention disclosed herein provide methods and compositions that are useful for upregulating PAH for the treatment and/or prevention of diseases associated with reduced PAH expression or function such as PKU.

Congenital Bilateral Absence of Vas Deferens (CBAVD) and Cystic Fibrosis (CF)—CFTR CFTR is a cyclic-AMP activated ATP-gated anion channel that transports ions across cell membranes. CFTR is predominantly found in epithelial cells in the lung, liver, pancreas, digestive tract, reproductive tract, and skin. A main function of CFTR is to move chloride and thiocyanate ions out of epithelial cells. In order to maintain electrical balance, sodium ions move with the chloride and thiocyanate ions, resulting in an increase of electrolytes outside of the cell. This increase results in movement of water out of the cell by osmosis, creating bodily fluids such as mucus, sweat, and digestive juices, depending on the organ. When CFTR activity is reduced or abolished, ion transport is affected, resulting in reduced water movement out of cells and abnormally viscous bodily fluids (e.g. sticky and viscous mucus, sweat, or digestives juices).

Mutations in CFTR are associated with congenital bilateral absence of vas deferens (CBAVD) and cystic fibrosis. Males with congenital bilateral absence of the vas deferens often have mutations that result in reduced CFTR activity. As a result of these mutations, the movement of water and salt into and out of cells is disrupted. This disturbance leads to the production of a large amount of thick mucus that blocks the developing vas deferens (a tube that carries sperm from the testes) and causes it to degenerate, resulting in infertility.

Cystic fibrosis (CF) is an autosomal recessive disease characterized by overly viscous secretions in the lungs, pancreas, liver, and intestine. In the lungs, difficulty breathing and frequent infection are common results of mucus build-up. Viscous secretions in the pancreas lead to scarring, fibrosis, and cyst formation which can subsequently lead to diabetes. Additionally, absorption of nutrients in the intestine is decreased due to a lack of digestive enzymes provided by the pancreas. Blockage of the intestine is also common due to thickening of the feces. Aspects of the invention disclosed herein provide methods and compositions that are useful for upregulating CFTR for the treatment and/or prevention of diseases associated with reduced CFTR expression or function such CBAVD or CF.

Exemplary Nucleotide Analogs

Each strand of the ds mRNA molecule can independently include one or more nucleotide analogs, e.g., having modifications to the base, e.g., nucleobases including but not limited to 1,5-dimethyluracil, 1-methyluracil, 2-amino-6-hydroxyaminopurine, 2-aminopurine, 3-methyluracil, 5-(hydroxymethyl)cytosine, 5-bromouracil, 5-carboxycytosine, 5-fluoroorotic acid, 5-fluorouracil, 5-formylcytosine, 8-azaadenine, 8-azaguanine, $N^6$-hydroxyadenine, allopurinol, hypoxanthine, or thiouracil, modifications of the sugar group or modifications of the phosphate group. In one embodiment, at least one strand of the ds mRNA molecule includes, but is not limited to, 1-methyladenosine, 2-methylthio-$N^6$-hydroxynorvalyl carbamoyladenosine, 2-methyladenosine, 2-O-ribosylphosphate adenosine, $N^6$-methyl-$N^6$-threonylcarbamoyladenosine, $N^6$-acetyladenosine, $N^6$-glycinylcarbamoyladenosine, $N^6$-isopentenyladenosine, $N^6$-methyladenosine, $N^6$-threonylcarbamoyladenosine. $N^6$, $N^6$-dimethyladenosine, N $N^6$-(cis-hydroxyisopentenyl)adenosine. $N^6$-hydroxynorvalylcarbamoyladenosine, 1,2-O-dimethyladenosine, $N^6$,2-O-dimethyladenosine, 2-O-methyladenosine, $N^6$, $N^6$,O-2-trimethyladenosine, 2-methylthio-$N^6$-(cis-hydroxyisopentenyl) adenosine, 2-methylthio-$N^6$-methyladenosine, 2-methylthio-$N^6$-isopentenyladenosine, 2-methylthio-$N^6$-threonyl carbamoyladenosine, 2-thiocytidine, 3-methylcytidine, $N^4$-acetylcytidine, 5-formylcytidine, $N^4$-methylcytidine, 5-methylcytidine, 5-hydroxymethylcytidine, lysidine, $N^4$-acetyl-2-O-methylcytidine, 5-formyl-2-O-methylcytidine, 5,2-O-dimethylcytidine, 2-O-methylcytidine, $N^4$,2-O-dimethylcytidine, $N^4$, $N^4$,2-O-trimethylcytidine, 1-methylguanosine, $N^2$,7-dimethylguanosine, $N^2$-methylguanosine, 2-O-ribosylphosphate guanosine, 7-methylguanosine, under modified hydroxywybutosine, 7-aminomethyl-7-deazaguanosine, 7-cyano-7-deazaguanosine, $N^2$, $N^2$-dimethylguanosine, 4-demethylwyosine, epoxyqueuosine, hydroxywybutosine, isowyosine, $N^2$,7,2-O-trimethylguanosine, $N^2$,2-O-dimethylguanosine, 1,2-O-dimethylguanosine, 2-O-methylguanosine, N $N^2$2,2-O-trimethylguanosine, N2,N2,7-trimethylguanosine, peroxywybutosine, galactosyl-queuosine, mannosyl-queuosine, queuosine, archaeosine, wybutosine, methywyosine, wyosine, 2-thioundine, 3-(3-amino-3-carboxypropyl)uridine, 3-methyluridine, 4-thiouridine, 5-methyl-2-thioundine, 5-methylaminomethyluridine, 5-carboxymethyluridine, 5-carboxymethylaminomethyluridine, 5-hydroxyuridine, 5-methyluridine, 5-taurinomethyluridine, 5-carbamoylmethyluridine, 5-(carboxyhydroxymethyl)uridine methyl ester, dihydrouridine, 5-methyldihydrouridine, 5-methylaminomethyl-2-thiouridine, 5-(carboxyhydroxymethyl)uridine, 5-(isopentenylaminomethyl)uridine, 5-(isopentenylaminomethyl)-2-thiouridine, 3,2-O-dimethyluridine, 5-carboxymethylaminomethyl-2-O-methylundine, 5-carbamoylmethyl-2-O-methyluridine, 5-methoxycarbonylmethyl-2-O-methyluridine, 5-(isopentenylaminomethyl)-2-O-methyluridine, 5,2-O-dimethyluridine, 2-O-methyluridine, 2-thio-2-O-methylundine, uridine 5-oxyacetic acid, 5-methoxycarbonylmethyluridine, uridine 5-oxyacetic acid methyl ester, 5-methoxyuridine, 5-aminomethyl-2-thiouridine, 5-carboxymethylaminomethyl-2-thiouridine, 5-methylaminomethyl-2-selenouridine, 5-methoxycarbonylmethyl-2-thiouridine, 5-taurinomethyl-2-thiouridine, pseudouridine, 1-methyl-3-(3-amino-3-carboxypropyl) pseudouridine, 1-methylpseudouridine, 3-methylpseudouridine, 2-O-methylpseudouridine, inosine, 1-methylinosine, 1,2-O-dimethylinosine and 2-O-methylinosine, or any combination thereof.

In one embodiment, at least one strand of the ds mRNA molecule includes, but is not limited to, cytosine arabinoside or fludarabine. In one embodiment, at least one strand of the ds mRNA molecule includes, but is not limited to, cladribine, acyclovir, 2',3'-dideoxyinosine; 9-β-D-ribofuranosyladenine; .beta.-arabinofuranosylcytosine; arabinosylcytosine; 4-amino-5-fluoro-1-[(2R,5S)-2-(hydroxymethyl)-1,3-oxathiolan-5-yl]-1,2-di-hydropyrimidin-2-one; 2',3'-dideoxy-3'-thiacytidine; 2'-3'-dideoxycytidine; {(1S,4R)-4-[2-amino-6-(cyclopropylamino)-9H-purin-9-yl]cyclopent-2-en-1-y-l}methanol; 2-Amino-9-[(1S,3R,4S)-4-hydroxy-3-(hydroxymethyl)-2-methylidenecyclopenty-1]-6,9-dihydro-3H-purin-6-one; 2'-3'-didehydro-2'-3'-dideoxythymidine; 1-(2-deoxy-.beta.-L-erythro-pentofuranosyl)-5-methylpyrimidine-2,4(1H,3H)-1-dione; 1-[(2R,4S,5S)-4-azido-5-(hydroxymethyl)oxolan-2-yl]-5-methylpyrimi-dine-2,4-dione; 1-[(2R,4S,5R)-4-hydroxy-5-(hydroxymethyl)oxolan-2-yl]-5-iodo-1,2,3,4-tetr-ahydropyrimidine-2,4-dione; 1-[4-hydroxy-5-(hydroxymethyl)oxolan-2-yl]-5-(trifluoromethyl) pyrimidine-2,4-dione; 5-Fluoro-2'-deoxycytidine; 5-Fluorodeoxycytidine; Floxuridine (5-Fluoro-1-[4-hydroxy-5-(hydroxymethyl)tetrahydrofuran-2-yl]-1H-pyrimidi-ne-2,4-dione); 4-amino-1-(2-deoxy-2,2-difluoro-A-D-erythropentofuranosyl)pyrimidin-1-2(1H)-one; or 2',2'-difluoro-2'-deoxycytidine; (8R)-3-(2-deoxy-β-D-erythropentofuranosyl)-3,4,7,8-tetrahydroimidaz-o[4,5-d][1,3] diazepin-8-ol, or any combination thereof.

In one embodiment, a strand of the ds mRNA may include analogs such as 2'-O-methyl-substituted RNA, locked nucleic acid (LNA) or BNA (Bridged Nucleic Acid), morpholino, or peptide nucleic acid (PNA), or any combination thereof.

In one embodiment, nucleotide analogs include phosphorothioate nucleotides or deazapurine nucleotides and other nucleotide analogs.

In one embodiment, one or more strands of the ds mRNA molecule can independently include a modified nucleotide selected from a deoxyribonucleotide, a dideoxyribonucleotide, an acydonucleotide, a 3'-deoxyadenosine (cordycepin), a 3'-azido-3'-deoxythymidine (AZT), a 2',3'-dideoxyinosine (ddl), a 2',3'-dideoxy-3'-thiacytidine (3TC), a 2',3'-didehydro-2',3'-dideoxythymidine (d4T), a monophosphate nucleotide of 3'-azido-3'-deoxythymidine (AZT), a 2',3'-dideoxy-3'-thiacytidine (3TC) and a monophosphate nucleotide of 2',3'-didehydro-2',3'-dideoxythymidine (d4T), a 4-thiouracil, a 5-bromouracil, a 5-iodouracil, a 5-(3-aminoallyl)-uracil, a 2'-O-alkyl ribonucleotide, a 2'-O-methyl ribonucleotide, a 2'-amino ribonucleotide, a 2'-fluoro ribonucleotide, or a locked nucleic acid; or any combination thereof.

In one embodiment, the nucleotide modification includes 2' modifications, e.g., 2' F on pyrimidines or 2' H or 2' OMe on purines.

In one embodiment, the nucleotide modification includes a phosphate backbone modification selected from a phosphonate, a phosphorothioate, a phosphotriester; a morpholino nucleic acid; or a peptide nucleic acid (PNA).

Sugar modifications in the strand(s) include, but are not limited to, replacing the heteroatoms at the 2' and 3' carbons with hydrogen, another heteroatom or an alkyl group; replacing the H's at the 2' carbon with a heteroatom or alkyl group; replacing the 2' and 3' carbons with a heteroatom, most commonly S or O; removing the 2' and/or 3' carbons to generate acyclic sugars; replacing the 4'-OH with N, S, or an alkyl group; adding alkyl groups to the 4'-carbon; replacing the 5'-hydroxyl with N or a phosphonate, or interconversion of both the sugar stereochemistry (D vs. L) and anomeric configuration (a vs. 3).

The invention will be described by the following non-limiting examples.

Example 1

A codon-optimized firefly luciferase gene with 5' and 3' human beta globin untranslated regions (UTRs) was installed onto the pcDNA3.1 plasmid (FIG. 1). This firefly luciferase gene was transcribed by in vitro transcription. A 5' 7-methyl guanosine cap and 3' poly-A tail was added by enzymatic synthesis. The 5' m$^7$G cap, 3' poly-A tail, both UTRs, and codon optimization have been shown to dramatically increased luciferase expression in vivo.

Figure 2:
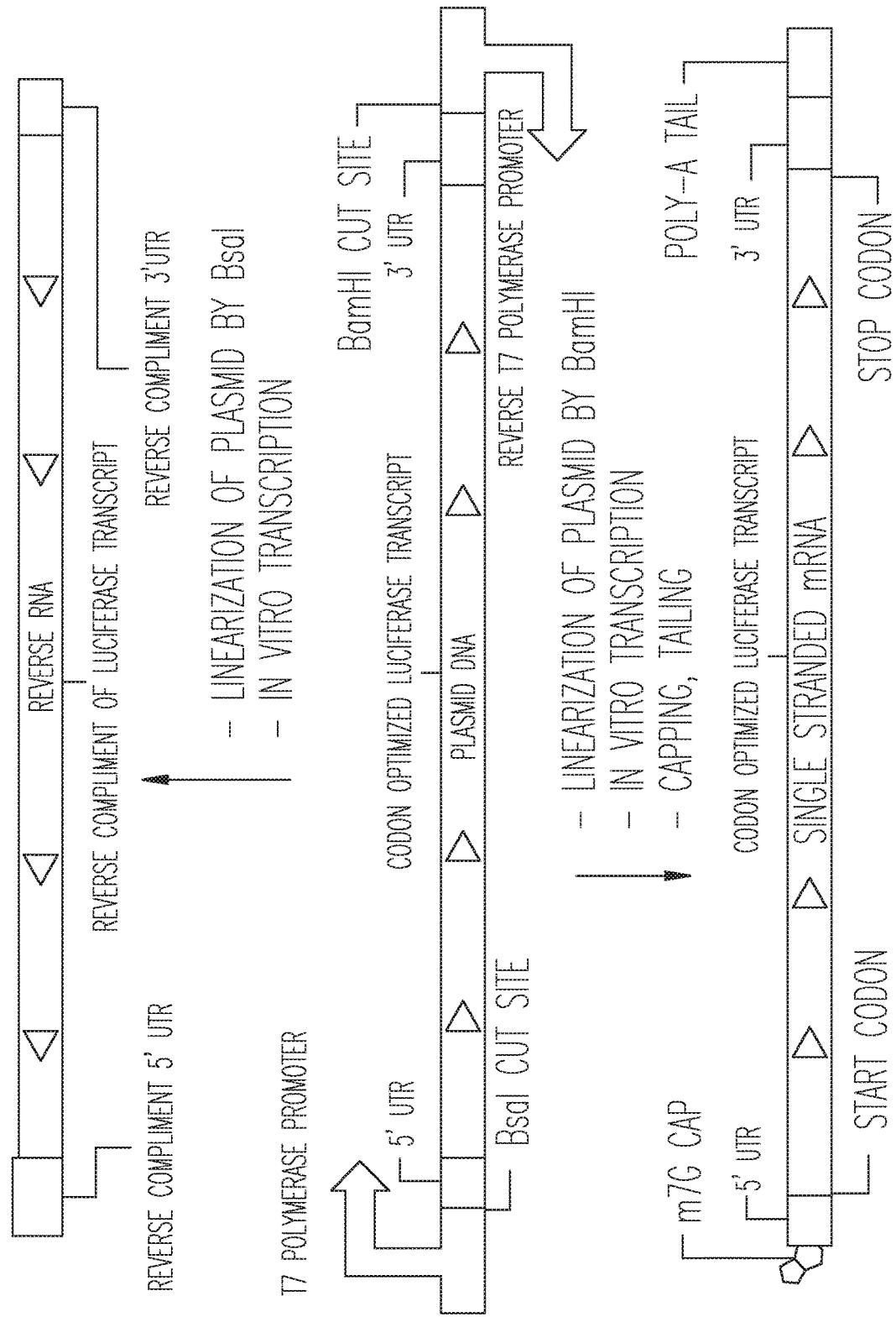
FIG. 2. Schematic of use of exemplary vector for reverse RNA expression.

Double stranded mRNA was produced by constructing a plasmid with two T7 promoters in reverse orientations, both flanking the codon-optimized luciferase gene. Sense and antisense strands were produced in separate reactions by cutting the plasmid in different positions (FIG. 2). The sense strand was capped with 7-methyl guanosine and poly-A tailed. The sense and antisense strands were annealed by heating to 65° C. with slow cooling. Uridine was replaced with pseudouridine to reduce the immune response.

Figure 3:
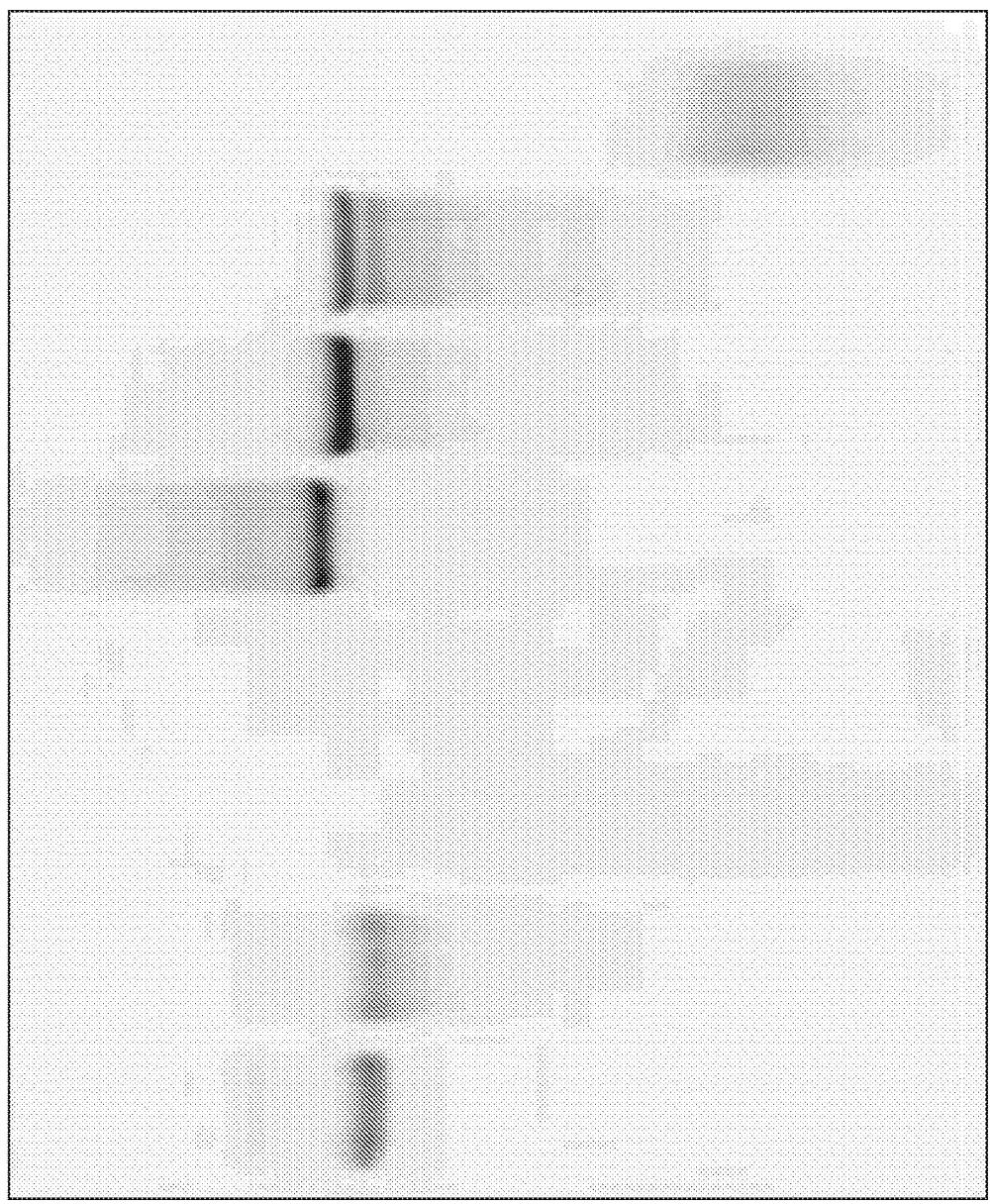
FIG. 3. Resistance of ssRNA and ds mRNA to RNase.

The relative stability of ss mRNA and ds mRNA when challenged by digestion with RNase A was compared. ss mRNA and ds mRNA were incubated with increasing amounts of RNase A for 10 minutes at 37° C. and products were immediately separated on an agarose gel. The relatively stability of ds mRNA versus ss mRNA approaches infinity when both are digested with 10 μg of RNAse A (FIG. 3).

Figure 4:
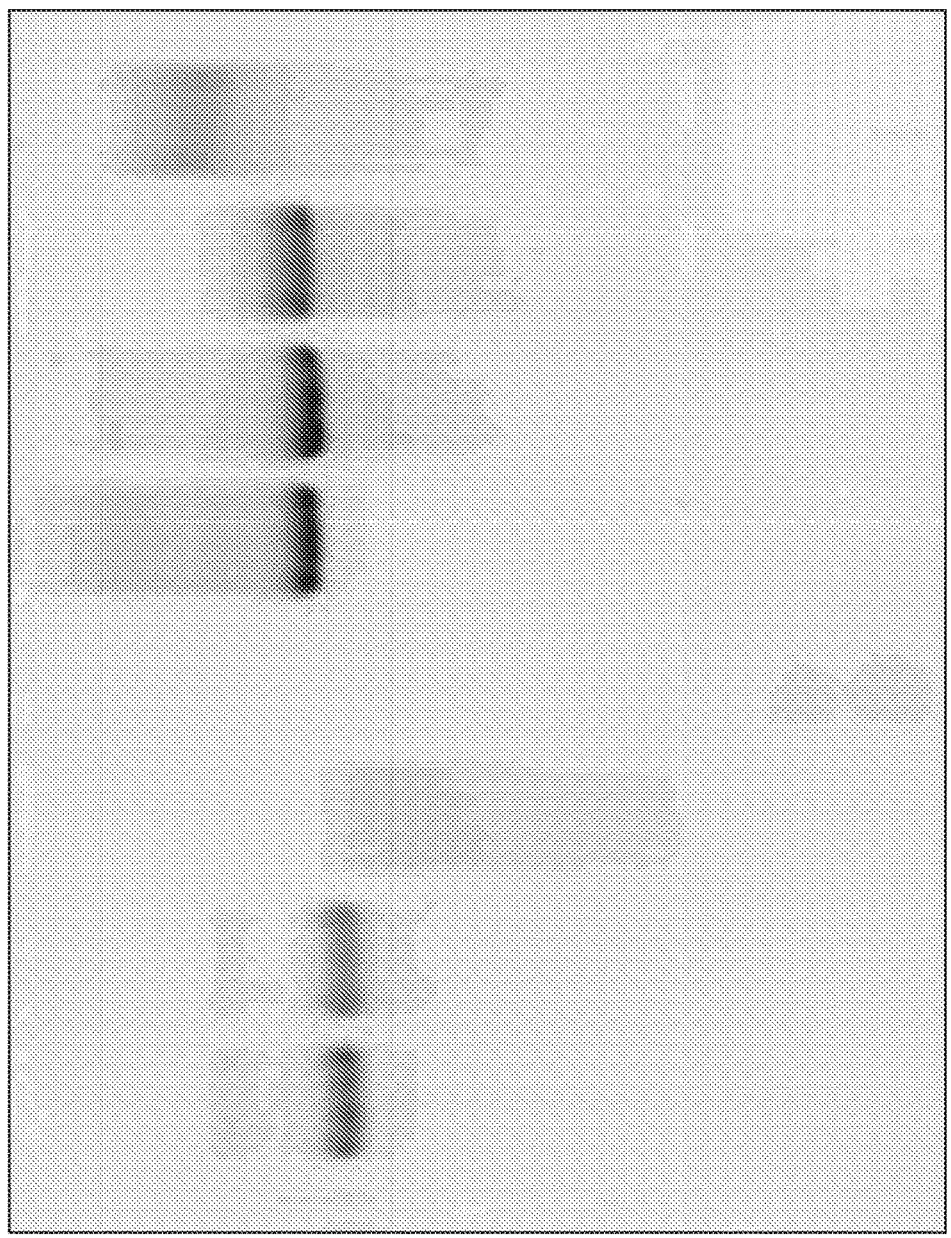
FIG. 4. Resistance of ssRNA and ds mRNA to serum nucleases.

Serum nucleases degrade RNA. The relative stability of ds mRNA versus ss mRNA was compared when digested with increasing amounts of mouse serum. ss mRNA and ds mRNA were incubated with 0.0008% to 8% vol/vol ratio of mouse serum for 10 minutes at 37° C. then analyzed on an agarose gel (FIG. 4). ds mRNA is shown to be highly stable compared to ss mRNA. The relative increase in stability approaches infinity by comparing ss mRNA and ds mRNA digested with 0.8% serum.

Figure 5:
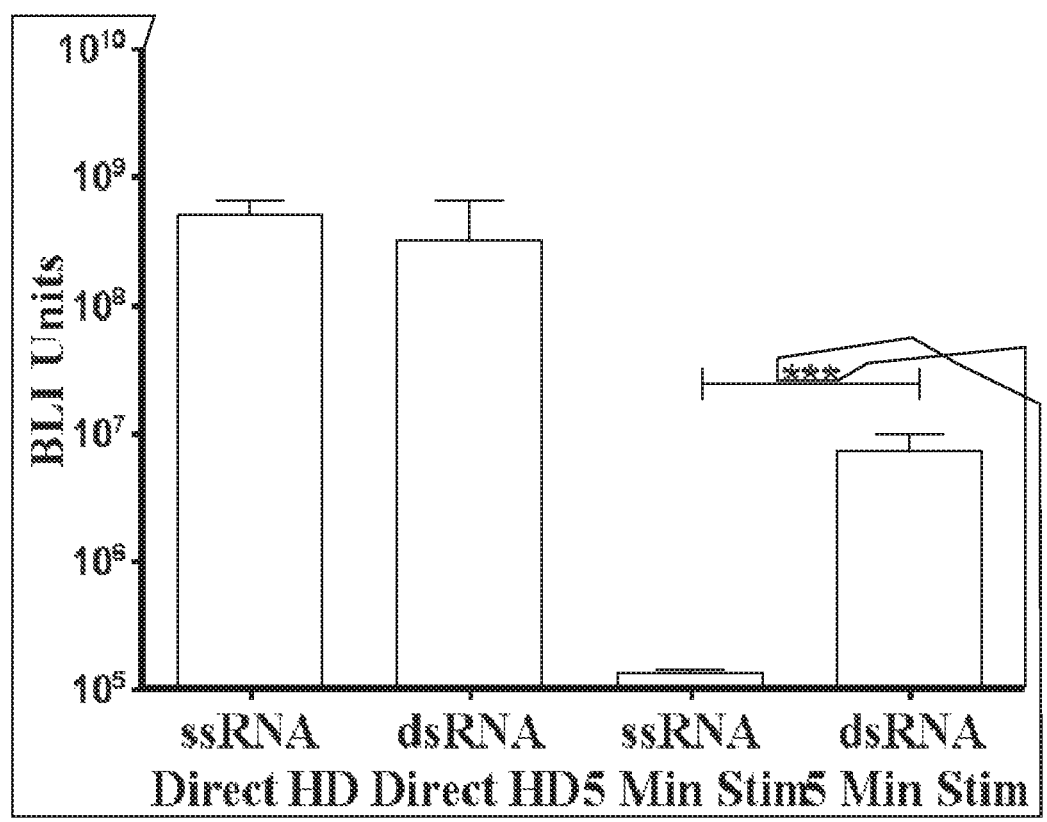
FIG. 5. Stability in vivo of ds mRNA-PEG-peptide complexes.

The relative translation of ss mRNA and ds mRNA into protein was compared by administering a 1 μg dose of each into mice via the tail vein by direct hydrodynamic injection. The expression of luciferase in the liver was determined at times ranging from 4 to 72 hours by serially measuring the light produced from the liver by in vivo bioluminescence imaging following i.p. dosing of luciferin (FIG. 5). The level of luciferase expression for both ss mRNA and ds mRNA peaked at 4 hours and was maintained for 24 hours before declining over 48 and 72 hours. The results demonstrate that ds mRNA and ss mRNA produce equivalent expression of luciferase at times ranging from 4-72 hours.

Example 2

Double stranded mRNA may be produced by constructing a plasmid with two T7 promoters in reverse orientations, both flanking a gene of interest, e.g., one useful for applications including but not limited to cancer immunotherapy, such as Melan-A, tyrosinase, gp100, MAGE-A1, MAGE-A3 or survivin, infectious disease, e.g., a viral or bacterial protein, protein replacement or augmentation, e.g., EPO, IL-10, VEGF-A, surface B protein or Foxp3, somatic reprogramming, or genome editing. Sense and antisense strands may be produced in separate reactions by cutting the plasmid in different positions. The sequences may be codon optimized, e.g., to improve translation or to decrease endonuclease activity, for instance, one or more uridine residues may be replaced with pseudouridine to reduce the immune response, or natural residues may be replaced with other analogs such as 2-thiouridine, 5-methyluridine, 5-methylcytidine or N6-methyl adenosine, or any combination thereof. The sense strand may be capped with 7-methyl guanosine or with cap analogs, and poly-A tailed. The sense and antisense strands are annealed by heating to 65° C. with slow cooling.

For example, for cancer immunotherapy, a double stranded mRNA having a sense strand that encodes a mammalian melanoma antigen recognized by T-cells (MART-1), e.g., where the sense strand has nucleic acid sequences with at least 90%, 92%, 95%, 97%, 98%, 99% or 100% nucleic acid sequence identity to coding sequences in SEQ ID NO:1 or a nucleic acid sequence that encodes a protein with at least 80% amino acid sequence identity to a protein encoded by SEQ ID NO:1; a double stranded mRNA having a sense strand that encodes a mammalian tyrosinase, e.g., where the sense strand has nucleic acid sequences with at least 90%, 92%, 95%, 97%, 98%, 99% or 100% nucleic acid sequence identity to coding sequences in SEQ ID NO:2 or a nucleic acid sequence that encodes a protein with at least 80%, 82%, 85%, 87%, 90%, 92%, 95%, 97%, 98%, 99% or 100% amino acid sequence identity to a protein that is encoded by SEQ ID NO:2; a double stranded mRNA having a sense strand that encodes a mammalian melanoma antigen, e.g., where the sense strand has nucleic acid sequences with at least 90%, 92%, 95%, 97%, 98%, 99% or 100% nucleic acid sequence identity to coding sequences in SEQ ID NO:3 or a nucleic acid sequence that encodes a protein with at least 80%, 82%, 85%, 87%, 90%, 92%, 95%, 97%, 98%, 99% or 100% amino acid sequence identity to a protein that is encoded by SEQ ID NO:3; or a double stranded mRNA having a sense strand that encodes a mammalian survivin, e.g., where the sense strand has nucleic acid sequences with at least 90%, 92%, 95%, 97%, 98%, 99% or 100% nucleic acid sequence identity to coding sequences in SEQ ID NO:4 or a nucleic acid sequence that encodes a protein with at least 80%, 82%, 85%, 87%, 90%, 92%, 95%, 97%, 98%, 99% or 100% amino acid sequence identity to a protein that is encoded by SEQ ID NO:4, may be employed.

```
                                                            (SEQ ID NO: 1)
AGCAGACAGAGGACTCTCATTAAGGAAGGTGTCCTGTGCCCTGACCCTACAAGATGCCAA

GAGAAGATGCTCACTTCATCTATGGTTACCCCAAGAAGGGGCACGGCCACTCTTACACCA

CGGCTGAAGAGGCCGCTGGGATCGGCATCCTGACAGTGATCCTGGGAGTCTTACTGCTCA

TCGGCTGTTGGTATTGTAGAAGACGAAATGGATACAGAGCCTTGATGGATAAAAGTGTTC

ATGTTGGCACTCAATGTGCCTTAACAAGAAGATGCCCACAAGAAGGGTTTGATCATCGGG

ACAGCAAAGTGTCTCTTCAAGAGAAAAACTGTGAACCTGTGGTTCCCAATGCTCCACCTG

CTTATGAGAAACTCTCTGCAGAACAGTCACCACCACCTTATTCACCTTAAGAGCCAGCGA

GACACCTGAGACATGCTGAAATTATTTCTCTCACACTTTTGCTTGAATTTAATACAGACA

TCTAATGTTCTCCTTTGGAATGGTGTAGGAAAAATGCAAGCCATCTCTAATAATAAGTCA

GTGTTAAAATTTTAGTAGGTCCGCTAGCAGTACTAATCATGTGAGGAAATGATGAGAAAT

ATTAAATTGGGAAAACTCCATCAATAAATGTTGCAATGCATGATACTATCTGTGCCAGAG

GTAATGTTAGTAAATCCATGGTGTTATTTTCTGAGAGACAGAATTCAAGTGGGTATTCTG

GGGCCATCCAATTTCTCTTTACTTGAAATTTGGCTAATAACAAACTAGTCAGGTTTTCGA

ACCTTGACCGACATGAACTGTACACAGAATTGTTCCAGTACTATGGAGTGCTCACAAAGG

ATACTTTTACAGGTTAAGACAAAGGGTTGACTGGCCTATTTATCTGATCAAGAACATGTC

AGCAATGTCTCTTTGTGCTCTAAAATTCTATTATACTACAATAATATATTGTAAAGATCC

TATAGCTCTTTTTTTTTGAGATGGAGTTTCGCTTTTGTTGCCCAGGCTGGAGTGCAATGG

CGCGATCTTGGCTCACCATAACCTCCGCCTCCCAGGTTCAAGCAATTCTCCTGCCTTAGC

CTCCTGAGTAGCTGGGATTACAGGCGTGCGCCACTATGCCTGACTAATTTTGTAGTTTTA

GTAGAGACGGGGTTTCTCCATGTTGGTCAGGCTGGTCTCAAACTCCTGACCTCAGGTGAT
```

-continued

CTGCCCGCCTCAGCCTCCCAAAGTGCTGGAATTACAGGCGTGAGCCACCACGCCTGGCTG

GATCCTATATCTTAGGTAAGACATATAACGCAGTCTAATTACATTTCACTTCAAGGCTCA

ATGCTATTCTAACTAATGACAAGTATTTTCTACTAAACCAGAAATTGGTAGAAGGATTTA

AATAAGTAAAAGCTACTATGTACTGCCTTAGTGCTGATGCCTGTGTACTGCCTTAAATGT

ACCTATGGCAATTTAGCTCTCTTGGGTTCCCAAATCCCTCTCACAAGAATGTGCAGAAGA

AATCATAAAGGATCAGAGATTCTG (SEQ ID NO: 2)
TATTGAGTTCTTCAAACATTGTAGCCTCTTTATGGTCTCTGAGAAATAACTACCTTAAAC

CCATAATCTTTAATACTTCCTAAACTTTCTTAATAAGAGAAGCTCTATTCCTGACACTAC

CTCTCATTTGCAAGGTCAAATCATCATTAGTTTTGTAGTCTATTAACTGGGTTTGCTTAG

GTCAGGCATTATTATTACTAACCTTATTGTTAATATTCTAACCATAAGAATTAAACTATT

AATGGTGAATAGAGTTTTTCACTTTAACATAGGCCTATCCCACTGGTGGGATACGAGCCA

ATTCGAAAGAAAAGTCAGTCATGTGCTTTTCAGAGGATGAAAGCTTAAGATAAAGACTAA

AAGTGTTTGATGCTGGAGGTGGGAGTGGTATTATATAGGTCTCAGCCAAGACATGTGATA

ATCACTGTAGTAGTAGCTGGAAAGAGAAATCTGTGACTCCAATTAGCCAGTTCCTGCAGA

CCTTGTGAGGACTAGAGGAAGAATGCTCCTGGCTGTTTTGTACTGCCTGCTGTGGAGTTT

CCAGACCTCCGCTGGCCATTTCCCTAGAGCCTGTGTCTCCTCTAAGAACCTGATGGAGAA

GGAATGCTGTCCACCGTGGAGCGGGGACAGGAGTCCCTGTGGCCAGCTTTCAGGCAGAGG

TTCCTGTCAGAATATCCTTCTGTCCAATGCACCACTTGGGCCTCAATTTCCCTTCACAGG

GGTGGATGACCGGGAGTCGTGGCCTTCCGTCTTTTATAATAGGACCTGCCAGTGCTCTGG

CAACTTCATGGGATTCAACTGTGGAAACTGCAAGTTTGGCTTTTGGGGACCAAACTGCAC

AGAGAGACGACTCTTGGTGAGAAGAAACATCTTCGATTTGAGTGCCCCAGAGAAGGACAA

ATTTTTTGCCTACCTCACTTTAGCAAAGCATACCATCAGCTCAGACTATGTCATCCCCAT

AGGGACCTATGGCCAAATGAAAAATGGATCAACACCCATGTTTAACGACATCAATATTTA

TGACCTCTTTGTCTGGATGCATTATTATGTGTCAATGGATGCACTGCTTGGGGGATCTGA

AATCTGGAGAGACATTGATTTTGCCCATGAAGCACCAGCTTTTCTGCCTTGGCATAGACT

CTTCTTGTTGCGGTGGGAACAAGAAATCCAGAAGCTGACAGGAGATGAAAACTTCACTAT

TCCATATTGGGACTGGCGGGATGCAGAAAAGTGTGACATTTGCACAGATGAGTACATGGG

AGGTCAGCACCCCACAAATCCTAACTTACTCAGCCCAGCATCATTCTTCTCCTCTTGGCA

GATTGTCTGTAGCCGATTGGAGGAGTACAACAGCCATCAGTCTTTATGCAATGGAACGCC

CGAGGGACCTTTACGGCGTAATCCTGGAAACCATGACAAATCCAGAACCCCAAGGCTCCC

CTCTTCAGCTGATGTAGAATTTTGCCTGAGTTTGACCCAATATGAATCTGGTTCCATGGA

TAAAGCTGCCAATTTCAGCTTTAGAAATACACTGGAAGGATTTGCTAGTCCACTTACTGG

GATAGCGGATGCCTCTCAAAGCAGCATGCACAATGCCTTGCACATCTATATGAATGGAAC

AATGTCCCAGGTACAGGGATCTGCCAACGATCCTATCTTCCTTCTTCACCATGCATTTGT

TGACAGTATTTTTGAGCAGTGGCTCCGAAGGCACCGTCCTCTTCAAGAAGTTTATCCAGA

AGCCAATGCACCCATTGGACATAACCGGGAATCCTACATGGTTCCTTTTATACCACTGTA

CAGAAATGGTGATTTCTTTATTTCATCCAAAGATCTGGGCTATGACTATAGCTATCTACA

AGATTCAGACCCAGACTCTTTTCAAGACTACATTAAGTCCTATTTGGAACAAGCGAGTCG

GATCTGGTCATGGCTCCTTGGGGCGGCGATGGTAGGGGCCGTCCTCACTGCCCTGCTGGC

AGGGCTTGTGAGCTTGCTGTGTCGTCACAAGAGAAAGCAGCTTCCTGAAGAAAAGCAGCC

-continued
ACTCCTCATGGAGAAAGAGGATTACCACAGCTTGTATCAGAGCCATTTATAAAAGGCTTA

GGCAATAGAGTAGGGCCAAAAAGCCTGACCTCACTCTAACTCAAAGTAATGTCCAGGTTC

CCAGAGAATATCTGCTGGTATTTTTCTGTAAAGACCATTTGCAAAATTGTAACCTAATAC

AAAGTGTAGCCTTCTTCCAACTCAGGTAGAACACACCTGTCTTTGTGTTGCTGTTTTCAC

TCAGCCCTTTTAACATTTTCCCCTAAGCCCATATGTCTAAGGAAAGGATGCTATTTGGTA

ATGAGGAACTGTTATTTGTATGTGAATTAAAGTGCTCTTATTTT (SEQ ID NO: 3)
CCCACACTCCCGCCTGTTGCCCTGACCAGAGTCATCATGCCTCTTGAGCAGAGGAGTCAG

CACTGCAAGCCTGAAGAAGGCCTTGAGGCCCGAGGAGAGGCCCTGGGCCTGGTGGGTGCG

CAGGCTCCTGCTACTGAGGAGCAGGAGGCTGCCTCCTCCTCTTCTACTCTAGTTGAAGTC

ACCCTGGGGGAGGTGCCTGCTGCCGAGTCACCAGATCCTCCCCAGAGTCCTCAGGGAGCC

TCCAGCCTCCCCACTACCATGAACTACCCTCTCTGGAGCCAATCCTATGAGGACTCCAGC

AACCAAGAAGAGGAGGGGCCAAGCACCTTCCCTGACCTGGAGTCCGAGTTCCAAGCAGCA

CTCAGTAGGAAGGTGGCCGAGTTGGTTCATTTTCTGCTCCTCAAGTATCGAGCCAGGGAG

CCGGTCACAAAGGCAGAAATGCTGGGGAGTGTCGTCGGAAATTGGCAGTATTTCTTTCCT

GTGATCTTCAGCAAAGCTTTCAGTTCCTTGCAGCTGGTCTTTGGCATCGAGCTGATGGAA

GTGGACCCCATCGGCCACTTGTACATCTTTGCCACCTGCCTGGGCCTCTCCTACGATGGC

CTGCTGGGTGACAATCAGATCATGCCCAAGGCAGGCCTCCTGATAATCGTCCTGGCCATA

ATCGCAAGAGAGGGCGACTGTGCCCCTGAGGAGAAAATCTGGGAGGAGCTGAGTGTGTTA

GAGGTGTTTGAGGGAGGGAAGACAGTATCTTGGGGGATCCCAAGAAGCTGCTCACCCAA

CATTTCGTGCAGGAAAACTACCTGGAGTACCGGCAGGTCCCCGGCAGTGATCCTGCATGT

TATGAATTCCTGTGGGGTCCAAGGGCCCTCGTTGAAACCAGCTATGTGAAAGTCCTGCAC

CATATGGTAAAGATCAGTGGAGGACCTCACATTTCCTACCCACCCCTGCATGAGTGGGTT

TTGAGAGAGGGGAAGAGTGAGTCTGAGCACGAGTTGCAGCCAGGGCCAGTGGGAGGGGG

TCTGGGCCAGTGCACCTTCCGGGGCCGCATCCCTTAGTTTCCACTGCCTCCTGTGACGTG

AGGCCCATTCTTCACTCTTTGAAGCGAGCAGTCAGCATTCTTAGTAGTGGGTTTCTGTTC

TGTTGGATGACTTTGAGATTATTCTTTGTTTCCTGTTGGAGTTGTTCAAATGTTCCTTTT

AACGGATGGTTGAATGAGCGTCAGCATCCAGGTTTATGAATGACAGTAGTCACACATAGT

GCTGTTTATATAGTTTAGGAGTAAGGGTCTTGTTTTTTACTCAAATTGGGAAATCCATTC

CATTTTGTGAATTGTGACATAATAATAGCAGTGGTAAAAGTATTTGCTTAAAATTGTGAG

CGAATTAGCAATAACATACATGAGATAACTCAAGAAATCAAAAGATAGTTGATTCTTGCC

TTGTACCTCAATCTATTCTGTAAAATTAAACAAATATGCAAACCAGGATTTCCTTGACTT

CTTTGAGAATGCAAGCGAAATTAAATCTGAATAAATAATTCTTCCTCTTCAAAAAAAAAA

AAAAAAAAAAAAGGCCACA (SEQ ID NO: 4)
GTTGGCAGAGGTGGCGGCGGCGGCATGGGTGCCCCGACGTTGCCCCCTGCCTGGCAGCCC

TTTCTCAAGGACCACCGCATCTCTACATTCAAGAACTGGCCCTTCTTGGAGGGCTGCGCC

TGCACCCCGGAGCGGATGGCCGAGGCTGGCTTCATCCACTGCCCCACTGAGAACGAGCCA

GACTTGGCCCAGTGTTTCTTCTGCTTCAAGGAGCTGGAAGGCTGGGAGCCAGATGACGAC

CCCATAGAGGAACATAAAAAGCATTCGTCCGGTTGCGCTTTCCTTTCTGTCAAGAAGCAG

TTTGAAGAATTAACCCTTGGTGAATTTTTGAAACTGGACAGAGAAAGAGCCAAGAACAAA

ATTGCAAAGGAAACCAACAATAAGAAGAAAGAATTTGAGGAAACTGCGAAGAAAGTGCGC

-continued

```
CGTGCCATCGAGCAGCTGGCTGCCATGGATTGAGGCCTCTGGCCGGAGCTGCCTGGTCCC

AGAGTGGCTGCACCACTTCCAGGGTTTATTCCCTGGTGCCACCAGCCTTCCTGTGGGCCC

CTTAGCAATGTCTTAGGAAAGGAGATCAACATTTTCAAATTAGATGTTTCAACTGTGCTC

TTGTTTTGTCTTGAAAGTGGCACCAGAGGTGCTTCTGCCTGTGCAGCGGGTGCTGCTGGT

AACAGTGGCTGCTTCTCTCTCTCTCTCTTTTTTGGGGGCTCATTTTTGCTGTTTTGAT

TCCCGGGCTTACCAGGTGAGAAGTGAGGGAGGAAGAAGGCAGTGTCCCTTTTGCTAGAGC

TGACAGCTTTGTTCGCGTGGGCAGAGCCTTCCACAGTGAATGTGTCTGGACCTCATGTTG

TTGAGGCTGTCACAGTCCTGAGTGTGGACTTGGCAGGTGCCTGTTGAATCTGAGCTGCAG

GTTCCTTATCTGTCACACCTGTGCCTCCTCAGAGGACAGTTTTTTTGTTGTTGTGTTTTT

TTGTTTTTTTTTTTTGGTAGATGCATGACTTGTGTGTGATGAGAGAATGGAGACAGAGT

CCCTGGCTCCTCTACTGTTTAACAACATGGCTTTCTTATTTTGTTTGAATTGTTAATTCA

CAGAATAGCACAAACTACAATTAAAACTAAGCACAAAGCCATTCTAAGTCATTGGGGAAA

CGGGGTGAACTTCAGGTGGATGAGGAGACAGAATAGAGTGATAGGAAGCGTCTGGCAGAT

ACTCCTTTTGCCACTGCTGTGTGATTAGACAGGCCCAGTGAGCCGCGGGCACATGCTGG

CCGCTCCTCCCTCAGAAAAAGGCAGTGGCCTAAATCCTTTTTAAATGACTTGGCTCGATG

CTGTGGGGACTGGCTGGGCTGCTGCAGGCCGTGTGTCTGTCAGCCCAACCTTCACATCT

GTCACGTTCTCCACACGGGGGAGAGACGCAGTCCGCCCAGGTCCCCGCTTTCTTTGGAGG

CAGCAGCTCCCGCAGGGCTGAAGTCTGGCGTAAGATGATGGATTTGATTCGCCCTCCTCC

CTGTCATAGAGCTGCAGGGTGGATTGTTACAGCTTCGCTGGAAACCTCTGGAGGTCATCT

CGGCTGTTCCTGAGAAATAAAAAGCCTGTCATTTCAAACACAAAAAAAAAAAAAAAAAA

AAAAAAAA
```

Thus, in one embodiment, double stranded RNA having a sense strand that encodes a cancer antigen, e.g., one that is useful to prevent, inhibit or treat cancer or otherwise enhance the immune system, may be introduced to a host organism, e.g., a mammal such as a human, optionally with an adjuvant. The double stranded RNA may be directly administered, or by administration of two plasmids, each encoding one of the strands, optionally in conjunction with positively charged polymers such as PEI, cationic polypeptides, e.g., protamine, or dendrimers, or using a delivery vehicle, e.g., a microparticle or nanoparticle, for instance, a liposome. For instance, double stranded RNA having a sense strand that encodes tyrosinase or survivin may be used to treat a melanoma patient, e.g., as an immunotherapeutic.

For infectious disease, a double stranded mRNA having a sense strand that encodes a microbial protein including a protein or glycoprotein specific for a viral pathogen, a bacterial pathogen, an algal pathogen, or a fungal pathogen, for example, a respiratory syncytial virus (RSV) fusion protein, e.g., where the sense strand has nucleic acid sequences with at least 90%, 92%, 95%, 97%, 98%, 99% or 100% nucleic acid sequence identity to coding sequences in SEQ ID NO:5 or a nucleic acid sequence that encodes a protein with at least 80%, 82%, 85%, 87%, 90%, 92%, 95%, 97%, 98%, 99% or 100% amino acid sequence identity to a protein that is encoded by SEQ ID NO:5, may be employed as a vaccine.

(SEQ ID NO: 5)
```
ATGGAGCTGCTGATCCACAGGTTAAGTGCAATCTTCCTAACTCTTGCTATTAATGCATTG

TACCTCACCTCAAGTCAGAACATAACTGAGGAGTTTTACCAATCGACATGTAGTGCAGTT

AGCAGAGGTTATTTTAGTGCTTTAAGAACAGGTTGGTATACCAGTGTCATAACAATAGAA

TTAAGTAATATAAAAGAAACCAAATGCAATGGAACTGACACTAAAGTAAAACTTATAAAA

CAAGAATTAGATAAGTATAAGAATGCAGTGACAGAATTACAGCTACTTATGCAAAACACA

CCAGCTGCCAACAACCGGGCCAGAAGAGAAGCACCACAGTATATGAACTATACAATCAAT

ACCACTAAAAACCTAAATGTATCAATAAGCAAGAAGAGGAAACGAAGATTTCTGGGCTTC

TTGTTAGGTGTAGGATCTGCAATAGCAAGTGGTATAGCTGTATCCAAAGTTCTACACCTT

GAAGGAGAAGTGAACAAGATCAAAAATGCTTTGTTATCTACAAACAAAGCTGTAGTCAGT
```

-continued

```
CTATCAAATGGGGTCAGTGTTTTAACCAGCAAAGTGTTAGATCTC

```
CCCTAGTCATGGTGGCACCGTCTGGGGCCCGACTAGGTCCCTCACCCCACCTACAGGCCC

TTCTCCAGGACAGACCACACTTCATGCATCAGCTCTCCACTGTGGATGCCCATGCCCAGA

CCCCTGTGCTCCAAGTGCGTCCACTGGACAACCCAGCCATGATCAGCCTCCCACCACCTT

CTGCTGCCACTGGGGTCTTCTCCCTCAAGGCCCGGCCTGGCCTGCCACCTGGGATCAATG

TGGCCAGTCTGGAATGGGTGTCCAGGGAGCCAGCTCTACTCTGCACCTTCCCACGCTCGG

GTACACCCAGGAAAGACAGCAACCTTTTGGCTGCACCCCAAGGATCCTACCCACTGCTGG

CAAATGGAGTCTGCAAGTGGCCTGGTTGTGAGAAGGTCTTCGAGGAGCCAGAAGAGTTTC

TCAAGCACTGCCAAGCAGATCATCTCCTGGATGAGAAAGGCAAGGCCCAGTGCCTCCTCC

AGAGAGAAGTGGTGCAGTCTCTGGAGCAGCAGCTGGAGCTGGAAAAGGAGAAGCTGGGAG

CTATGCAGGCCCACCTGGCTGGGAAGATGGCGCTGGCCAAGGCTCCATCTGTGGCCTCAA

TGGACAAGAGCTCTTGCTGCATCGTAGCCACCAGTACTCAGGGCAGTGTGCTCCCGGCCT

GGTCTGCTCCTCGGGAGGCTCCAGACGGCGGCCTGTTTGCAGTGCGGAGGCACCTCTGGG

GAAGCCATGGCAATAGTTCCTTCCCAGAGTTCTTCCACAACATGGACTACTTCAAGTACC

ACAATATGCGACCCCCTTTCACCTATGCCACCCTTATCCGATGGGCCATCCTGGAAGCCC

CGGAGAGGCAGAGGACACTCAATGAAATCTACCATTGGTTTACTCGCATGTTCGCCTACT

TCAGAAACCACCCCGCCACCTGGAAGAATGCCATCCGCCACAACCTGAGCCTGCACAAGT

GCTTTGTGCGAGTGGAGAGCGAGAAGGGAGCAGTGTGGACCGTAGATGAATTTGAGTTTC

GCAAGAAGAGGAGCCAACGCCCCAACAAGTGCTCCAATCCCTGCCCTTGACCTCAAAACC

AAGAAAAGGTGGGCGGGGAGGGGGCCAAAACCATGAGACTGAGGCTGTGGGGGCAAGGA

GGCAAGTCCTACGTGTACCTATGGAAACCGGGCGATGATGTGCCTGCTATCAGGGCCTCT

GCTCCCTATCTAGCTGCCCTCCTAGATCATATCATCTGCCTTACAGCTGAGAGGGGTGCC

AATCCCAGCCTAGCCCCTAGTTCCAACCTAGCCCCAAGATGAACTTTCCAGTCAAAGAGC

CCTCACAACCAGCTATACATATCTGCCTTGGCCACTGCCAAGCAGAAAGATGACAGACAC

CATCCTAATATTTACTCAACCCAAACCCTAAAACATGAAGAGCCTGCCTTGGTACATTCG

TGAACTTTCAAAGTTAGTCATGCAGTCACACATGACTGCAGTCCTACTGACTCACACCCC

AAAGCACTCACCCACAACATCTGGAACCACGGGCACTATCACACATAGGTGTATATACAG

ACCCTTACACAGCAACAGCACTGGAACCTTCACAATTACATCCCCCCAAACCACACAGGC

ATAACTGATCATACGCAGCCTCAAGCAATGCCCAAAATACAAGTCAGACACAGCTTGTCA

GAACACGCTCGTGTGCACGTACACACATGCAGCCCCTCCACTCTATCTCCTGAGTTCCAT

GAATACACACCGACTCTCCAAGATGTACCCCACGTCTCACTTGCCACTGACCCCAGTTCC

CTACCCACAAGCCCCAATCCATGCCTAAGCGTGGCCCACAGAAGAACTTCTCTTTTATTT

GGGATCCAAGGCCCCTGGCCCCCAGTGCCCATCCAATAAACTGTGGTCAGCTGGACAATC

ACCCTGATCAGATATGGGAACATATAAGCAGACAGCTGGGTTTAAGATCCCAGCAGGAGA

AAGCGGATACCAAATGAAAGAGAGTGCTAGAACAGGTGCCTCAGCACTGTCTCCAGCACC

CCAAATTCCTGCCTGTGGTTAGGAGACATCCATCAGGGCTCTAGGCCTCTCGGACCCGGC

CCAAGAGGCCAGCATTCTCCTGGCGAAGGGCTCGGTAGTCCTCACAGATCTTCTCCAGGT

TGCTCAAAGTCTTCTTGCCCATCTCTGTCTCAATCTAAGAAAACAGGATGCACACTTCTT

CAGCCCCTGCAGGCTGCCCCTCTACTGAACTCCTCCCTGCTCCTCCTATTCCCGTAACAG

CAGCCTGTTCCTTCCCATCACTGGGCTTCTGGGTATGTCCTTCCCTCCACTCCACCTAAA

GCAGCAACTTCTGCCATGGGCTCTGGGAGGCATTAGGAGCCGCAAGCTAAAAGCCAGGGC
```

-continued

TCAGAGTAGGCTACTGGCTAGCTTCAGGTCCCAGGCACAGTGGGCACGAAGGCAAAGCCT

CTAGCTGTTAGTTGTCTGGTTTCAAAGACTCTCAGCGCAAAACAAGGAACTATCCCCTGG

CCTGTCTCCATTCCCCTTACCAGTCCCAGGTCTCACCTGCTCCTCAAGATCTCGAACTTC

CCTCATGATAGTGCCTGTGTCCTCAATGGTCTGGATGAGCTGACTGCAATTCTGGAGACA

GCAAGAATACAAGGCTTGCACCTATGCTGGCCCTCTCCAGCCAACCCACCAGGCACATGG

CTCCCCTCACCTCATGCAGGGCAGCTAGGTACTTGTAGGCTTTCCGAACAGCATCATCCT

TCTTAGCATCCTGATAAGACAAAGGGGATCTCCGAGATATCAGCAAGCCATTCCCCCTTT

TCCACTACTCTATGCCCCTATAAGACCACCCTTTACTAGTACTTTGCCTTCATCCTCCAC

AGAGCAAAGCTAGGCCCCAAGCAACAGTGCACCTAAAGGACTCACAGAGGGGCAGGCAAC

AACTCAGTCCCGCCTCCACCCTCCCGGAGGCCAGCCTGGTCCATACCTTGAACACAAGCT

CATCAGTCACTGCAAATGTCCGGTCGAGCTTCCCAGAGAGAGAGTTGATTTCCTTCTGCA

GTTCCTTTGTGTCCGACAAGATCTGGTAGAAACCAGGGTAACTATCAGTGCACATCTTGG

GCAAGGTAGCTGATCAGTGATAACACTCACGTGCCTATACTTACATCCAGTCAGGGCCCA

TGTCGCTGTGTTGGGGTGACTATTATGTGTTGGAGTGTGCCTGAACAGCTCTGCCTAGTA

GTGAGCATAAAGTCCCTGTGT (SEQ ID NO: 7)
GGTACCATGTCTATCCTGACCCTAAGATTAGTTCCTCGGGTTTGAGGATTGCAGCAACAC

TGACCGTTCAGGCCCTGGTCAAGGTGGGGCTGCTGCTTCTTCCTTGGCTTCTTTCCAAGG

AGCCACCAAGAGGCAGAAAGAAATGAAGAGACACAAAGCAAGGCAGAATAGCACTTCGGA

TGACACTGTCCGCATTGCCCGACAGATATGGCACTAGACTGCAGCCAAAGGACTCTCTGA

AACTATTAACAAGGTTGTGAGAACTTGTGACCAGTCTGTGAGGTGCTGTGTCTGGGTGTC

ATGTCACTGGGGACATCATCAGTGTCACCAGTGGCACAGTGGAATGCCTGGTGAGCTGAG

ACACACAAATGAGGCAGGCGTGGTGGGCACACACCTGTAATCCCAACGGAACGTAAACCT

GGTATGGCAGTGCTCACCTGTATGTGGTGGCACTCAGGAAGTGGAGGCAGGAGCATTAGG

AGTCTAAGGTCATCCTCAGCTACATTGACAAATCTGAGACCAGCCTGGGCGACATGAGTC

CTTGTGTTAAAAAAAAAAAAAAAAAAAAAAAAAAAAAAGAGAGAGAGAGAGAGAGAG

AGAATCAGACAGTGGTGGTGCATGCTTTTAATCCAGCACTTGGGAGGCAGAGGCAAACAG

ATTACTGTGAGATCAAGGCCAGCCTGGTCTTCAGAGCAAGTTCCAGGACAAGCAGGGCTA

CATAGAAAAAACCCGTCTCTATAAACAAACAAACAAACAAACAAAAAAAGCAGATC

TCGTGACTCTCTGAAGAAGGCCATTTCCCGCCAGTCCTTGGGGTTAGCCGTAAGTAGCAG

GCTGTAGTGTCTCGAGGCCACAAAAACTAGGAGAACCCTGGGACCACTTCCAGGGTGTCG

TTTTACATCACATGTCCAACTATTTACCTTCATCTTGGGGCTAGCTCCCACCCCATACAG

CCTGTGAGTGCTGGAGGACTTTCTAGGGAGCCTCCGTAGGAAAGGCACTGGCAGGTCTCA

GAAAAGGATCGGGGTCCTGATGGGGGGCGGGGGTCAGTAGTGCCTAATGCACTCAGACA

AGCACCGGCGCTGCAGCCAGCCCTGAACTGCTTTTTCTCTAAGCCCAGCCAGGTGTGGAC

ATAGCCTCAGAGGACCACGTGTCAGCTGAATCCCATCTCATGCCCAGGAGGGTGACTGG

GAGAGATGGGCATCTGCTTCTGGGTAAAGCTACCTAAGAGCCACAGGGGACACAGAAATC

TCAGCCTCACAGGGCACTTTCCTGTTTGTCTAATGCTCCTCTCCCTAGCACCAGCCAGGA

GTCTATAGAATCAGAGGATTTAAAGTAAGGGGGGAGTGGGAGGTCGGTTGGCCCCAGGA

GCACCCTAAGTGTGCCCTTCCGGCACTTACCCTGCGTCAAGAGCCAGGAAGGAAGCTCTC

AAGGGCGTTGCATAAGAGTAGAGGATTGAGAAGCCTGGGGTGGGGCTAGAGAGGCTCATT

-continued

```
CTGACCCCACTCAGCATCCCTTGCACAGTCCAGAGCGTGGGGATCAAACGAGACCCCCTT
GTTTGACGGTGAACAAAGTCAGGCTGAGGGGGTTCGGGAAGGGGTAAAGGACTAGGAAC
CGACATCGGCCAGCACACGGGAGGTGGACAGGGGTGTCCCTGCTGAGAAGACCTGGAGGG
CTCTCAAGACACAGGCAAACACTGAGGTCAGCCTGTTCCCATGGAGTCCAGCCCCCAGGT
CCTCTCCCCTACTATAAGAGCCCATGACTCAAGTAGGGTACTAAGCAGTAGGCAGCCATG
GCCAAGTCGCACCTACTGCAGTGGCTACTGCTGCTTCCTACCCTCTGCTGCCCAGGTGCA
GGTGAGTCCCCGGCCTCCCTCACAGAGGCCTCTCCAGCACTTACTGAGTCAGCTCCGTGC
CCAGAAAGACCCCAGTCTGCACATAATCCAGAATTTAAACGCCAGTTAGCTGAGGCACAG
AGAAGTCCTAGGGCCTCATCCAAGGTCACAGTTAGTGGATGGATGTTGAAGCAGGAGGAC
TCAGAGCTGCCTGGCAGAAGCAATGGCCACTCCTTTGCAATGAAACTGGGTTGGAGGTGG
GGTGGAGGCAGGGTGCCGAGTGTATGCTGGATCCTGATGAGAGTTGCTCTGACCCCAACT
CCAGCTATCACGTCGGCCTCATCCCTGGAGTGTGCACAAGGCCCTCAATTCTGGTGCCAA
AGCCTGGAGCATGCAGTGCAGTGCAGAGCCCTGGGGCACTGCCTGCAGGAAGTCTGGGGG
CATGCAGGAGCTGTGAGTAGCACCAAGCGGGCACTGGAAATCCAGGGAGGAGGAACTGGG
GTGGATTCTGAGCGGACCTTAGGAAATTGGAGTTCCCACAAGGCTGGGGTGGCAGGGAAT
GATGGAATGGTATAGTGTGACAGGAAATGGTGGGCAGAGTACAATAGAAGGAAACATGGT
GGAATGAGATGAATGGGGTGGGCATGGTGGGTAAGACAGGGTGGATGTGTGGGTAAGACA
GGGTGGATGTGGTGGGTAAGACAGGGTAGATGTGGTGGGTAAGAGGGGGTGAGCATGTGG
GTAAGATGGGGTGGCTGGGGTGAGATGGACAAGATGGAATAGAACAGGGTGGATCAAGTG
GGTGGCACAGAATGGGATGGAATTTGCACAATGGGATGAGATGGATGATGGGTGGGTAG
CCTTAAGGTACCTGTCAGCCTGTGTCTGAGAAAGCCTCAATCCCTGGAGTTAGGAGCATG
CCCCCAACTCATTAGCCTCACTTGAGACCCTTTCTTCCAGAATGACCTGTGCCAAGAGTG
TGAGGATATTGTCCACCTCCTCACAAAGATGACCAAGGAAGATGCTTTCCAGGTAATGGG
AAACGGTACAGTGTGATCTGGTAGAGGCCTGGCGTCAGGGGACTCTGGTGGGGGCAGACC
TCAGAAAGACCAGGCTAATCCTCCCTTCTCTGCTCTCCCAGGAAGCAATCCGGAAGTTCC
TGGAACAAGAATGTGATATCCTTCCCTTGAAGCTGCTTGTGCCCCGGTGTCGCCAAGTGC
TTGATGTCTACCTGCCCCTGGTTATTGACTACTTCCAGAGCCAGATTGTGAGGACCCTGA
CCTACCTGCCGCACAGTGCATGTGCCTAAGTGGCCACTTACCTATATAAGTGGCACCCCA
ACACATGCACACACACATACACACCCACAGACGCAATAAGACACACACACACACGT
ACACACACACACACACACACACACACACACACACACACTTCCCACTACAGCCACAGGAAGCT
CAGTCTCTTCATCCAGATACCCAAATCAGAGCCTGCCTGCTCAGCATACTACAGACATTG
AGACCCGCCCTCCATCCCCTCACCCACACATGCCCACATTCTTATTGTCACACAATATGC
TCACACACACTCACTCTTTCCAGACACATGCTCCCAGGCCCTACACAGCCCCATCTCTCT
GTCTTTGTCCCTTTCATAGTGTCCTAAGATGCAGTACTTCACCCAGCCTGCTCCCCATAA
CCCCAGGCTCAAAGACTGTGGCCCTTGTCCCTGAATATGAACCTGGGCAGAGAGGGGTTC
CCTCCTTACCCTAAAACCCCTCACCTGTTCCATGCCCTAGAACCCCAAAGCCATCTGCAA
TCATGTAGGCCTGTGCCCACGTGGGCAGGCTAAGCCAGAACAGAATCCAGGGATGCCGGA
TGCCGTTCCAAACCCTCTGCTGGACAAGCTGGTCCTCCCTGTGCTGCCAGGAGCCCTCTT
GGCAAGGCCTGGGCCTCACACTCAGGTAAGCCAGTCCATTCCCAGCAGCTGCTGGGAATC
CAGAAGGCTAGCATGGCCGCTGAGACGCGTGGGCACCCAGAGAGGCTGAGCTCAAACTAG
GAGGCAGAGATGGCAAGGTCAGGCAAGGTCACACAACCGAGGTAGCTCCCAGCCTAACCA
```

-continued

```
CACTTCACCGCTTCCTTCCTCAGGACTTCTCTGAGCAACAGCTCCCCATTCCCCTGCCCT

TCTGCTGGCTTTGCAGAACTCTGATCAAGCGGGTTCAAGCCGTGATCCCCAAGGTAAGGA

CCACACAGAGCTCAGAGGGGCCCCCAATAGCTGGCACCTTCCTCCACCTCAACACTCCAA

GAAGGCTGTGAGGAGTTAGATGAGGAGACACCCACACATTGCTCCTACCCAAGGAACCTT

GAGGCTCAGGTATGGGAGGTTAGGTCAGAGCCACCTTCTCTTCCAACAGATCACCATCGG

AAGGCTGAGAAGCACTGGTTGTCACTGTAGGAAAAAAGTACATTAATTTCTCAAAAAAAA

AAAAAAACAGTTCATCAATAGTAAGCATCTCTTCTGTCCTCCAAATCCATGGTAGCCTCT

GCCAGTGCCTTGTCAGATGAGGATTGTTCTCCCCACAAATGGTCATGGCCTATCAACACT

AACACTAAGCCCACATCAGTCATAAAGACAACAGGGCACACAGTCAAGCCTTTCTGAAGC

CTGTGTGATGGAAGGAACGTGCAGACTATAGAGCAGGATGAGCTGAGGGGTCGCACAGAT

AAAAATGGTAACAGACAGGTCAGCCAGGGAGAGGCTCTGAAGAGGGTAACAACTAAGCCA

AGATCTAGGAGAAAACAAGGTCCCCAGGGGCCAAGGACATCCATCCATCAATAAAAAATG

AGCTCAATCAGATGTTGGAGGGAGGGACTCTGTAAGGAGGGACCAGGAGCAGGGGCAGC

GTTTGGGGTGTAAATGATAGATAAATGCCTTTAAAATGAGCTCAGAGGGCTAGGAAGATG

GCTCGGTGAGTACAGTCCTTGCTGAACCTGAGTTCAGATACTTGCACCCTCATAAAAGTT

GGGGGGTGGGCTGGAGACATGGCTCAGTAGTTAAGAGCACTGACTGCTCTTCTAGAGGTC

CTGAGTTCAATTCCCAGCAACCACTTGGTGGCTCACAACCACCTATAATGGGATCTGATG

CCCTCTTCTGGTGTGTCTGAACTTACATACATAAAATAAAAATAAAAGTTGGGGGTTGCT

CACAGTCAGCTAATGGATGGATCATAGGGCTCCCAATGGAGGAGCTAGAGAAAGTAGCCA

AGGAGCTAAAGGGATCTGCAACCCTATAGGTGGAACAACATTATGAGCTAACCAGTACCC

CGGAGCTCTTGACTCTAGCTGCATATATATCAAAAGATGGCCTAGTCGGCCATCACTGGA

AAGAGAGGCCCATTGGACTTGCAAACTTTATATGCCCCAGTACAGGGGAATACCAGGGCC

AAAAAGGGGGAGTGGGTGGGCAGGGGAGTGGGGGTGGGTGGATATGGGGGACTTTTGGTA

TAGCATTGGAAATGTAAATGAGTTAAATACCTAATAAAAAATGGAAAAAAAAAAGTTGG

GGGTTAGCAATGAACATTTGTAACCCTACACACTAGGTAGTCAGAAATAGGCAGATCCCT

AGAGCATGCTGGCCAGCCAGTCTAGCCAAATGGATGAGCTTCAGGGTTAGTGTGAGACCT

TGTCTCAAAAAAAAAAAAAAAAAAAAAAAAAATGGACGGCCTGAAGATTCGGATCGACAG

TTAGGAACATTTGCTGCTTTTCAGAAGAGTGAGTTGGGTACCCAGCACCACTGTCAGGCA

GCTCACAACCCCTGTAACTGCTGCTCTAGGGAATCCAATGCCCTCTTCTGGCAGCCAAG

GGCACCAGCACATATGTGGCATTCATATACTCAGATACACAGACATATGTAAAAATAAAA

ATAAATCTTTAGAAAATAATTAGGTAGGGAGTGAAGTGACTAAGGAAGACACTCAATCTT

GGCTCTGGCCTCCACACACATGTGCACATGTACTTAAACATCTACGTGCAAAACAAACAA

ACAAACACCCAGCCGTATCAATGTGAACATCACTGAGGACCGAAGGCATGAGCAAGACTG

TTAAGAGACAATGTATAGACAGATGGAGATGGCATCAGAATTGCTGAGAGGGGACAGGCA

GCCAACGGGGACCGTGCTGCATTGCCAGGGAAGCCAAGAGAGAAGGGTGTTTGACTGAT

TGAAAGGCAGCTGAACCATCAGGCAGGGTGAGAGTTAGGCAGGGGATGTGGAAGTGTTCC

AAAAAGGGGAGCAGGCATGGTGAGGCTTCCTAAGGTCAGAAGCCATTCTAGCGTGTTCTC

CAGGCAGCAGGGACCAGAGAGAGGATAAGGCCAGGGAAAGAGGCATGGGTGGAGGTAATC

CAGGAGTGAAGACCATTTCACCAATGAGCAGCTTGGTCATTGACTACAGTGACTATTGAT

TTACATCACCATGACAGGAGAGCCATGTGTGGGTCAATGATAACAGGTGGGTCTCTTAAG
```

-continued

```
TGAAGTGCCCCATTTGGGAGCCATCACACTCCAGGGGTGTCCATATTCTGAGTCCTCCCC

CTGCCTCAACCTCCTGGCACTGGGGCTAGCTGGTCACATGGGCTGAATAAGGAGTAAAGG

AAAAAGCCACACCCTGGTGACCTCTGTCACCCTTCAGCTAGAGCCTGCTTGGAATTGGAG

TTGAGGTAGGAGATGTGCTGGCTTTCCCAGGGGTTCCAAAAGCCAAAGACATGTCAGCTC

TGGGGGCCAGCAGAAGGAACTGCCTGTCTTCCTGATGCATAAGCATGGGAAGGTAGGTGG

CCCTCGGTCAGGGAATGGGTTTGAATTGGGTCAGGCTGTTAGATGCCATGGCCTTGCAGC

CCCCTTTCAAATGACTCAAGCCTTTAGAGCTAGATCTATATTTGGTGTCAACTGCAGATT

CTCTCAGTGACTCCGGGTGCACCTGAGACCCCTGCTGTCTTGGATGCTCAGTGACCTGTG

GACAGAACTGCTCTTTCCTAGAAGGGAGAAAGGGGATGCATCTGGGGTGCCCACTCAGTT

GGGCACAGTGACATCGTGCCAGAAGAAGGTTCTATGGTTGTCCTTTCTCCACCTTCACCC

CAGGGTGTGCTGGCTGTGGCTGTGTCCCAGGTGTGCCACGTGGTACCCCTGGTGGTGGGT

GGCATCTGCCAGTGCCTGGCTGAGCGCTACACAGTTCTCCTGCTAGACGCACTGCTGGGC

CGTGTGGTGCCCCAGCTAGTCTGTGGCCTTGTCCTCCGATGTTCCACTGAGGATGCCATG

GGCCCTGGTAAGACTTGCCCGTCCCCTCCCCCTCCCCAACTCACATCCCTCCAGTGCACA

TGGGAGGGAACATGGACAAGGTGGGGTTCAGGAACCAACACTTTTTTTAAACTATTTATT

TCTATGGATATGGCTGCTTTTATTTATATAGCTGAGGCTGGCTTTGAACTCCTAATTTCC

CTTCCTCAGCCATTCAAATGTTAGGAAAGGCTAGCAATGACTGTACTCAGCTTCTAGCTC

TCTCCAAGTGGACTTCTCCCAGTTGAGTTAAAGAGTGATGGGGAGGGGTGGGGAACAGG

GCAGGACCCTGGGAGAAGGCTAAGTTCTTTTTTTGCTCCAGCTTGGACATCTATATACCC

CATGTATGCCTGGCTCCCACAGAGGCCATAAAGGATGTCAAATCCCCTAGAATTGGAATA

ACTGACAGTTATGAGCCATCATGTGGGCTCTGGGAATCGAACCTCAGCCCTCTGGAAGA

GCAGCCAGTGCTCTTAACCACGGAACCATCTCTCCAGCCCCAGAACCAACACTTGTACAA

GACAGTCCTGGGGGAAAGATTAAAACAGAGTGTTACTACATAGCACAGGTTGGCCTCGAG

CTTGGTGCAATCCTCCTGCCTCAGCCTCTCAAATACTGGCATGACAAGGTATGTGCCTCC

ATACCCAGCTTGCTGGACAATTCTAACTGCTTTCTCTTTAGCCCTCCCTGCTGTGGAGCC

TCTGATAGAAGAATGGCCACTACAGGACACTGAGTGCCATTTCTGCAAGTCTGTGATCAA

CCAGGCCTGGAACACCAGTGAACAGGCTATGCCACAGGCAATGCACCAGGCCTGCCTTCG

CTTCTGGCTAGACAGGCAAAAGGTAGGGGCCCACGGGTTGGATGTATGTCATATGTGTG

ATGGTGCCGAGCTAGAAGAGACTTTGTAGCTAGACACACGCACGATGCTGGTTCCCAGCC

TGGTGGACAGGCATGTGGGTCAGACAATGATGGGATTGTAACAAATTTAACTGGCTAGGA

GACATCATGGACCCAAGGCTTTGGACTATGGAACATCAGCAGGCCTTCTTTATGGACTAA

GCACAAGAAAAGTCCTGTTAGTCCCAACAGGAAAGGGTCATACTGCCCTTTCTTGGTTTC

ACTCGATGGTGTGTTTGCCACACTGTTCTCCCAGTGTGCCATGTCACCCCCATGATGGGT

GGTAGCATTTGACAGTACCTAGCAGGCACCAGAAAATGAGAAAAGCCAGGGTCAGCTGGA

GCAGAAAAAGAACTTAGCCTTTTCCCAGGGTCCTGTTCTGCCCCACCCTGCTCACTCTGT

AGAAGTCCTGCAGGAGAGAGCTGGAAGCTGGTACCATAGTGCTAGCCTGTAATTCTAACA

TTTGGAAAGGCTGAAGAAGGAGAAATGGGAGTTCAAAGCCAGCCTCAGCTATATAAATAA

TGAGTTCAGGGTCAGCCTGGGCTACATGAGACCCTGTCTGGTGAAAGGAGACAGAGATAG

GAAAGAACATGAGGCTTGGGTAAGGCTCACTGGCATGGCCACAACCAAGTTTGATCCCTG

GGATCCGTATGGTAAACAAAGAGAATCAACTCCTGTAAACTTTCCTTATGAACACACACA

CACACGAAAACATAATTTTGAAGCCAGGCTGTGGTGGTGCACACCTTTAGTCCTAGCCCT
```

```
TGGGAGGCAGAAGCAGATGGATCTAAGTTTGAGCCCAGCCTGGTCTACAGTGTGAGCTCC

AGGACAGCCAGGGTTACACAGAGAAACCCTGTCTCACAAAACCAAAAAGAAATCAACAAC

CACAAAGAACTGAACAGATAGTTCCTTAAGCCTGTGATGAATCCCCTCACTACAGTGGGA

CTTTCTTTAGAGAGGGTCCTATGTAACTTAAACCGCCTCCACCTCCTTTGTACTGAGACT

ACAGGCAGGTACCACTACTGAGTTTCATGTAGTTCTGAAGTTGAAACTAAAGGTTTCATG

CATGCTAGGCAACCATGAGACGATGCTAAGCTGCAAGCCTGCTCCAGCTCCAAGGCCCTG

GCTTCCTCCAAAGCCTGGTTTCAGCCAAACTTAGATAGAGTCCCTTTTTTTAAGACTCAT

TTTATTTGTGTTTTTAGTGCATGTATGTATGGACATCATGTGTGTGGTGCCGGGGGGA

GGGGGTCAGAAGAGGCCATCAGATTCCCTGGAACTGGAGTTGAGTGGTTATAAGCCGTCC

TTCCTGTCCTCCAAAGAGCAGCAAGTGCCTAACCCCCGAGCCATCAGCCATTCAGCCCTT

CGGTTGAGTCTTTAATGGTCAGCCAGGCACTGATGGAAAAACACAAACCCACAGTCCGGA

GTGGCAGAGTGAGGTAGAACGCCAGATCTGCAGGTTAAGTTCTCTCCTAGAGGGGGGTCT

ACATATTGTGTCTTTCCTCAGTGTGAACAGTTTGTGGAACAGCACATGCCCCAGCTGCTG

GCCCTGGTGCCTAGGAGCCAGGATGCCCACATCACCTGCCAGGTATGCCCACTCTTCAGC

TGGTCCCAGGAGTCCCCTCTGCTCCCACAGTCCCACCCTCCTTGGTCTATGATCCTCAAG

AGCCCCATTTCTTGGATCCAGGAAGCCTAGGGCTCAGAAGCCCAGAACTAAGTGTACCCA

TAGAACAGGCTTTGGACTTGGAGCAGAAAAGAACACATACTGATTAGGTGGGAGGGCAA

GTTCATGATGGATGGGCAGCTGGGGGCTGGGGTATGATGCTCCTTATTGCATGTGGTGTG

TTTAGTGACCAGTTTGTTCTATGGTGGGGCTATAGTATGAGGTGGGGGTCCCACTAAGTC

CCAAGGCCATTGACTTAGGGAATGGCACAAGGGGTTCTGAAGGTGAAGGTGAAGTGAGAG

TTGTCTCCATAGCCTTGAGAATTAGACGTAGAAAGCTGAGGCCCACGTGCTGTCTCCAAC

AGGCCCTTGGCGTATGTGAGGCCCCGGCTAGCCCTCTGCAGTGCTTCCAAACCCCACACC

TCTGAGAACGCGGTCTCCAGGTGAGTCCAGCCTCCTGGGGAGAGAGAGGAATGGGTCTTT

GCTTGCTAAGGTTTGGGAACAAGATGGTCATCCTGCCCACTTCTGTGGACTGTGTCATCC

TACCTCTGCCAGGCACAGTTCCAGGCTCCTCGGGGTCTCCAGTGGTTCCATCAGGAAAAG

GCAGTCTTTTGGACCTATCGTCACTCCTTGCTCTCCCACCCCATCCAGCCCTCCACAGCT

TCTATCTAAGGCTTCATCACATCTGAGCTGCCTGACCTTAAAGATACTCCATGTTCGAGC

AATGGCCAACATTTCTTACTTCACTGTCTCGGCTGTCTCTCCCTCAGATGCCAGCAGCAC

CATGGTCACCTGACCTCACCCTGCCCAGGCTCCCTGTTTTCTAAGCCAGAAATAGCTCTG

ACACCAGAGTCAGGAAATGACATGGGAGTGTGGGGCGAGAAAGGCAACAGTCTCTCAAG

TGACCCTGACAGTAATCTGGTCCAGGTCACAATGTACTTAAAGCCAGCGCTCGCTGGGTA

GTCATTTATCCATTTGTTCCCATTTGTGAAAATCTGCTGGTGTGCACAGCTGGCCCACCA

CTTCTAATGCGAGGAAGGACCCCAGCACTGTCACAGCCACTGTGGGCAGAGGGGCACTTC

AAGTCAGTAAGTCCCTTGGGGGCCAATTTAATGTCTCCCCTCCCATCCCCCATCAAGTCC

ATCTGGGTGCGCGAAGGGAGGCAATCCAGGAGTCACCTTTTTCTAGCTCTCAGGGCTCTA

GGCCTTGCCTGCTGAAGAAGGAATTGTGAGAGACTCCCTGAGTTCTGGTCCCAACTCTGC

TATCAACAGTCAGTGGATCCCCCGGGAAAATCGCACAGCCCCCACCCTTTGCGATATCAC

TAAACTAGCTGCAAGTAGCCCAATGAAGGGAACTTCGGCACTTATGAACTGTCACCATCA

CAGTGACAGTGACCCTACTCCCACCAGTAGCTACTCTCCTTGAAAAAGACCTTACCTCCC

ACCCTAATGCTACTTCCTTTCCCACAGCAGCCTGCTCCAGAGGACAAGCCTCAGCCTGCA
```

-continued
```
CCCTCAGCCCTGTGTCAGTCTGTATGTCCCAGCTCTAACTACAGACCACCACCACCACCA

CCACCACCACCACCACCACCACCACCACCACCACCACCACCACCACCACCACCACAGTGG

TTTCTGGCTCCCCCCGGTGATGGGGGCGGCAGGCCCACGTCCTCTGGAAGCCTTCAGAA

GGGGCTTCGGGCCTTCGCCTCCACCAGAGCCAAGCCAGCTCCCATAGCTCCCACAGCCCA

CAGGGACTGAGAAGAACTGTTGTGGCTCCAAGAAGACATCGGGTAGAAGCTGGGTATAGC

CACACCAACCCCTTGCTAACATTTCTATGAAATCCAAACTTGAGAAGAATAAAGAATGGG

AACATGGAGCATTATTCTAAGGGCTGTGGGCGAGGCGCAGTGACAGGGCACTTTCCTAGC

AAGCAGGAAACCTGGGTTGGATCC
```

For somatic reprogramming, a double stranded mRNA having a sense strand that encodes Oct4, e.g., where the sense strand has nucleic acid sequences with at least 90% nucleic acid sequence identity to coding sequences in SEQ ID NO:8 or a nucleic acid sequence that encodes a protein with at least 80% amino acid sequence identity to a protein that is encoded by SEQ ID NO:8; Sox 2, e.g., where the sense strand has nucleic acid sequences with at least 90%, 92%, 95%, 97%, 98%, 99% or 100% nucleic acid sequence identity to coding sequences in SEQ ID NO:9 or a nucleic acid sequence that encodes a protein with at least 80%, 82%, 85%, 87%, 90%, 92%, 95%, 97%, 98%, 99% or 100% amino acid sequence identity to a protein that is encoded by SEQ ID NO:9; KIf4, e.g., where the sense strand has nucleic acid sequences with at least 90%, 92%, 95%, 97%, 98%, 99% or 100% nucleic acid sequence identity to coding sequences in SEQ ID NO:10 or a nucleic acid sequence that encodes a protein with at least 80%, 82%, 85%, 87%, 90%, 92%, 95%, 97%, 98%, 99% or 100% amino acid sequence identity to a protein that is encoded by SEQ ID NO:10; c-myc, e.g., where the sense strand has nucleic acid sequences with at least 90% nucleic acid sequence identity to coding sequences in SEQ ID NO:11 or a nucleic acid sequence that encodes a protein with at least 80%, 82%, 85%, 87%, 90%, 92%, 95%, 97%, 98%, 99% or 100% amino acid sequence identity to a protein that is encoded by SEQ ID NO:11, or any combination thereof, may be employed.

```
                                                           (SEQ ID NO: 8)
ATGGCGGGACACCTGGCTTCGGATTTCGCCTTCTCGCCCCCTCCAGGTGGTGGAGGTGATGGGCCA

GGGGGGCCGGAGCCGGGCTGGGTTGATCCTCGGACCTGGCTAAGCTTCCAAGGCCCTCCTGGAGG

GCCAGGAATCGGGCCGGGGGTTGGGCCAGGCTCTGAGGTGTGGGGGATTCCCCCATGCCCCCCGC

CGTATGAGTTCTGTGGGGGATGGCGTACTGTGGGCCCCAGGTTGGAGTGGGGCTAGTGCCCCAA

GGCGGCTTGGAGACCTCTCAGCCTGAGGGCGAAGCAGGAGTCGGGGTGGAGAGCAACTCCGATGG

GGCCTCCCCGGAGCCCTGCACCGTCACCCCTGGTGCCGTGAAGCTGGAGAAGGAGAAGCTGGAGC

AAAACCCGGAGGAGTCCCAGGACATCAAAGCTCTGCAGAAAGAACTCGAGCAATTTGCCAAGCTCCT

GAAGCAGAAGAGGATCACCCTGGGATATACACAGGCCGATGTGGGGCTCACCCTGGGGGTTCTATT

TGGGAAGGTATTCAGCCAAACGACCATCTGCCGCTTTGAGGCTCTGCAGCTTAGCTTCAAGAACATG

TGTAAGCTGCGGCCCTTGCTGCAGAAGTGGGTGGAGGAAGCTGACAACAATGAAAATCTTCAGGAG

ATATGCAAAGCAGAAACCCTCGTGCAGGCCCGAAAGAGAAAGCGAACCAGTATCGAGAACCGAGTG

AGAGGCAACCTGGAGAATTTGTTCCTGCAGTGCCCGAAACCCACACTGCAGCAGATCAGCCACATC

GCCCAGCAGCTTGGGCTCGAGAAGGATGTGGTCCGAGTGTGGTTCTGTAACCGGCGCCAGAAGGG

CAAGCGATCAAGCAGCGACTATGCACAACGAGAGGATTTTGAGGCTGCTGGGTCTCCTTTCTCAGG

GGGACCAGTGTCCTTTCCTCTGGCCCCAGGGCCCCATTTTGGTACCCCAGGCTATGGGAGCCCTCA

CTTCACTGCACTGTACTCCTCGGTCCCTTTCCCTGAGGGGAAGCCTTTCCCCCTGTCTCCGTCACC

ACTCTGGGCTCTCCCATGCATTCAAACTGA
                                                           (SEQ ID NO: 9)
ATGTACAACATGATGGAGACGGAGCTGAAGCCGCCGGGCCCGCAGCAAACTTCGGGGGCGGCGG

CGGCAACTCCACCGCGGCGGCGGCCGGCGGCAACCAGAAAAACAGCCCGGACCGCGTCAAGCGG

CCCATGAATGCCTTCATGGTGTGGTCCCGCGGGCAGCGGCGCAAGATGGCCCAGGAGAACCCCAA

GATGCACAACTCGGAGATCAGCAAGCGCCTGGGCGCCGAGTGGAAACTTTTGTCGGAGACGGAGAA
```

-continued

GCGGCCGTTCATCGACGAGGCTAAGCGGCTGCGAGCGCTGCACATGAAGGAGCACCCGGATTATAA

ATACCGGCCCCGGCGGAAAACCAAGACGCTCATGAAGAAGGATAAGTACACGCTGCCCGGCGGGC

TGCTGGCCCCGGCGGCAATAGCATGGCGAGCGGGGTCGGGGTGGGCGCCGGCCTGGGCGCGG

GCGTGAACCAGCGCATGGACAGTTACGCGCACATGAACGGCTGGAGCAACGGCAGCTACAGCATGA

TGCAGGACCAGCTGGGCTACCCGCAGCACCCGGGCCTCAATGCGCACGGCGCAGCGCAGATGCAG

CCCATGCACCGCTACGACGTGAGCGCCCTGCAGTACAACTCCATGACCAGCTCGCAGACCTACATG

AACGGCTCGCCCACCTACAGCATGTCCTACTCGCAGCAGGGCACCCCTGGCATGGCTCTTGGCTCC

ATGGGTTCGGTGGTCAAGTCCGAGGCCAGCTCCAGCCCCCCTGTGGTTACCTCTTCCTCCCACTCC

AGGGCGCCCTGCCAGGCCGGGGACCTCCGGGACATGATCAGCATGTATCTCCCCGGCGCCGAGGT

GCCGGAACCCGCCGCCCCCAGCAGACTTCACATGTCCCAGCACTACCAGAGCGGCCCGGTGCCCG

GCACGGCCATTAACGGCACACTGCCCCTCTCACACATGTGA (SEQ ID NO: 10)
ATGAGGCAGCCACCTGGCGAGTCTGACATGGCTGTCAGCGACGCGCTGCTCCCATCTTTCTCCACG

TTCGCGTCTGGCCCGGCGGGAAGGGAGAAGACACTGCGTCAAGCAGGTGCCCCGAATAACCGCTG

GCGGGAGGAGCTCTCCCACATGAAGCGACTTCCCCCAGTGCTTCCCGGCCGCCCCTATGACCTGGC

GGCGGCGACCGTGGCCACAGACCTGGAGAGCGGCGGAGCCGGTGCGGCTTGCGGCGGTAGCAAC

CTGGCGCCCCTACCTCGGAGAGAGACCGAGGAGTTCAACGATCTCCTGGACCTGGACTTTATTCTCT

CCAATTCGCTGACCCATCCTCCGGAGTCAGTGGCCGCCACCGTGTCCTCGTCAGCGTCAGCCTCCT

CTTCGTCGTCGCCGTCGAGCAGCGGCCCTGCCAGCGCGCCCTCCACCTGCAGCTTCACCTATCCGA

TCCGGGCCGGGAACGACCCGGGCGTGGCGCCGGGCGGCACGGGCGGAGGCCTCCTCTATGGCAG

GGAGTCCGCTCCCCCTCCGACGGCTCCCTTCAACCTGGCGGACATCAACGACGTGAGCCCCTCGG

GCGGCTTCGTGGCCGAGCTCCTGCGGCCAGAATTGGACCCGGTGTACATTCCGCCGCAGCAGCCG

CAGCCGCCAGGTGGCGGGCTGATGGGCAAGTTCGTGCTGAAGGCGTCGCTGAGCGCCCCTGGCAG

CGAGTACGGCAGCCCGTCGGTCATCAGCGTCAGCAAAGGCAGCCCTGACGGCAGCCACCCGGTGG

TGGTGGCGCCCTACAACGGCGGGCCGCCGCGCACGTGCCCCAAGATCAAGCAGGAGGCGGTCTCT

TCGTGCACCCACTTGGGCGCTGGACCCCCTCTCAGCAATGGCCACCGGCCGGCTGCACACGACTTC

CCCCTGGGGCGGCAGCTCCCCAGCAGGACTACCCCGACCCTGGGTGTTGAGGAAGTGCTGAGCAG

CAGGGACTGTCACCCTGCCCTGCCGCTTCCTCCCGGCTTCCATCCCCACCCGGGGCCCAATTACCC

ATCCTTCCTGCCCGATCAGATGCAGCCGCAAGTCCCGCCGCTCCATTACCAAGAGCTCATGCCACCC

GGTTCCTGCATGCCAGAGGAGCCCAAGCCAAAGAGGGGAAGACGATCGTGGCCCCGGAAAAGGAC

CGCCACCCACACTTGTGATTACGCGGGCTGCGGCAAAACCTACACAAAGAGTTCCCATCTCAAGGCA

CACCTGCGAACCCACACAGGTGAGAAACCTTACCACTGTGACTGGGACGGCTGTGGATGGAAATTC

GCCCGCTCAGATGAACTGACCAGGCACTACCGTAAACACACGGGGCACCGCCCGTTCCAGTGCCAA

AAATGCGACCGAGCATTTTCCAGGTCGGACCACCTCGCCTTACACATGAAGAGGCATTTTTAA (SEQ ID NO: 11)
CTGGATTTTTTTCGGGTAGTGGAAAACCAGCAGCCTCCCGCGACGATGCCCCTCAACGTTAGCTTCA

CCAACAGGAACTATGACCTCGACTACGACTCGGTGCAGCCGTATTTCTACTGCGACGAGGAGGAGA

ACTTCTACCAGCAGCAGCAGCAGAGCGAGCTGCAGCCCCGGCGCCCAGCGAGGATATCTGGAAG

AAATTCGAGCTGCTGCCCACCCCGCCCCTGTCCCCTAGCCGCCGCTCCGGGCTCTGCTCGCCCTCC

TACGTTGCGGTCACACCCTTCTCCCTTCGGGGAGACAACGACGGCGGTGGCGGGAGCTTCTCCACG

GCCGACCAGCTGGAGATGGTGACCGAGCTGCTGGGAGGAGACATGGTGAACCAGAGTTTCATCTGC

GACCCGGACGACGAGACCTTCATCAAAAACATCATCATCCAGGACTGTATGTGGAGCGGCTTCTCGG

-continued

```
CCGCCGCCAAGCTCGTCTCAGAGAAGCTGGCCTCCTACCAGGCTGCGCGCAAAGACAGCGGCAGC

CCGAACCCCGCCCGCGGCCACAGCGTCTGCTCCACCTCCAGCTTGTACCTGCAGGATCTGAGCGCC

GCCGCCTCAGAGTGCATCGACCCCTCGGTGGTCTTCCCCTACCCTCTCAACGACAGCAGCTCGCCC

AAGTCCTGCGCCTCGCAAGACTCCAGCGCCTTCTCTCCGTCCTCGGATTCTCTGCTCTCCTCGACGG

AGTCCTCCCCGCAGGGCAGCCCCGAGCCCCTGGTGCTCCATGAGGAGACACCGCCCACCACCAGC

AGCGACTCTGAGGAGGAACAAGAAGATGAGGAAGAAATCGATGTTGTTTCTGTGGAAAAGAGGCAG

GCTCCTGGCAAAAGGTCAGAGTCTGGATCACCTTCTGCTGGAGGCCACAGCAAACCTCCTCACAGC

CCACTGGTCCTCAAGAGGTGCCACGTCTCCACACATCAGCACAACTACGCAGCGCCTCCCTCCACT

CGGAAGGACTATCCTGCTGCCAAGAGGGTCAAGTTGGACAGTGTCAGAGTCCTGAGACAGATCAGC

AACAACCGAAAATGCACCAGCCCCAGGTCCTCGGACACCGAGGAGAATGTCAAGAGGCGAACACAC

AACGTCTTGGAGCGCCAGAGGAGGAACGAGCTAAAACGGAGCTTTTTTGCCCTGCGTGACCAGATC

CCGGAGTTGGAAAACAATGAAAAGGCCCCCAAGGTAGTTATCCTTAAAAAAGCCACAGCATACATCC

TGTCCGTCCAAGCAGAGGAGCAAAAGCTCATTTCTGAAGAGGACTTGTTGCGGAAACGACGAGAACA

GTTGAAACACAAACTTGAACAGCTACGGAACTCTTGTGCGTAA,
```

In one embodiment, for genome editing, a double stranded mRNA having a sense strand that encodes a nuclease such as Cas9, e.g., where the sense strand has nucleic acid sequences with at least 90%, 92%, 95%, 97%, 98%, 99% or 100% nucleic acid sequence identity to coding sequences in SEQ ID NO:12 or 13 for a nuclease, or a nucleic acid sequence that encodes a protein with at least 80%, 82%, 85%, 87%, 90%, 92%, 95%, 97%, 98%, 99% or 100% amino acid sequence identity to a nuclease that is encoded by SEQ ID NO:12 or 13, may be employed. The double stranded RNA for a nuclease such as Cas9 may be directly administered, or by administration of two plasmids, each encoding one of the strands, optionally in conjunction with positively charged polymers such as PEI, cationic polypeptides, e.g., protamine, or dendrimers, or using a delivery vehicle, e.g., a microparticle or nanoparticle, e.g., a liposome, optionally in conjunction with guide RNA.

(SEQ ID NO: 12)
```
atggataaga aatactcaat aggcttagat atcggcacaa atagcgtcgg atgggcggtg atcactgatg aatataaggt tccgtctaaa aagttcaagg ttctgggaaa tacagaccgc cacagtatca aaaaaaatct tatagggct ctttatttg acagtggaga gacagcggaa gcgactcgtc tcaaacggac agctcgtaga aggtatacac gtcggaagaa tcgtatttgt tatctacagg agatttttc aaatgagatg gcgaaagtag atgatagttt ctttcatcga cttgaagagt ctttttggt ggaagaagac aagaagcatg aacgtcatcc tattttgga aatatagtag atgaagttgc ttatcatgag aaatatccaa ctatctatca tctgcgaaaa aaattggtag attctactga taaagcggat ttgcgcttaa tctatttggc cttagcgcat atgattaagt ttcgtggtca tttttttgatt gagggagatt taaatcctga taatagtgat gtggacaaac tatttatcca gttggtacaa acctacaatc aattatttga agaaaaccct attaacgcaa gtggagtaga tgctaaagcg attctttctg cacgattgag taaatcaaga cgattagaaa atctcattgc tcagctcccc ggtgagaaga aaaatggctt atttgggaat ctcattgctt tgtcattggg tttgacccct aattttaaat caatttttga tttggcagaa gatgctaaat tacagctttc aaaagatact tacgatgatg atttagataa tttattggcg caaattggag atcaatatgc tgatttgttt ttggcagcta agaatttatc agatgctatt ttactttcag atatcctaag agtaaatact gaaataacta aggctcccct atcagcttca atgattaaac gctacgatga acatcatcaa gacttgactc ttttaaaagc tttagttcga caacaacttc cagaaaagta taaagaaatc ttttttgatc aatcaaaaaa cggatatgca ggttatattg atgggggagc tagccaagaa gaattttata aatttatcaa accaatttta
```

```
gaaaaaatgg atggtactga ggaattattg gtgaaactaa atcgtgaaga tttgctgcgc aagcaacgga cctttgacaa cggctctatt ccccatcaaa ttcacttggg tgagctgcat gctattttga agacaagaa agacttttat ccattttaa aagacaatcg tgagaagatt gaaaaaatct tgacttttcg aattccttat tatgttggtc cattggcgcg tggcaatagt cgttttgcat ggatgactcg gaagtctgaa gaaacaatta ccccatggaa ttttgaagaa gttgtcgata aggtgcttc agctcaatca tttattgaac gcatgacaaa ctttgataaa aatcttccaa atgaaaaagt actaccaaaa catagtttgc tttatgagta ttttacggtt tataacgaat tgacaaaggt caaatatgtt actgaaggaa tgcgaaaacc agcatttctt tcaggtgaac agaagaaagc cattgttgat ttactcttca aaacaaatcg aaaagtaacc gttaagcaat taaagaaga ttatttcaaa aaaatagaat gttttgatag tgttgaaatt tcaggagttg aagatagatt taatgcttca ttaggtacct accatgattt gctaaaaatt attaaagata aagatttttt ggataatgaa gaaaatgaag atatcttaga ggatattgtt ttaacattga ccttatttga agataggag atgattgagg aaagacttaa aacatatgct cacctctttg atgataaggt gatgaaacag cttaaacgtc gccgttatac tggttgggga cgtttgtctc gaaaattgat taatggtatt agggataagc aatctggcaa aacaatatta gatttttga aatcagatgg ttttgccaat cgcaatttta tgcagctgat ccatgatgat agtttgacat ttaaagaaga cattcaaaaa gcacaagtgt ctggacaagg cgatagttta catgaacata ttgcaaattt agctggtagc cctgctatta aaaaggtat tttacagact gtaaaagttg ttgatgaatt ggtcaaagta atggggcggc ataagccaga aaatatcgtt attgaaatgg cacgtgaaaa tcagacaact caaaagggcc agaaaaattc gcgagagcgt atgaaacgaa tcgaagaagg tatcaaagaa ttaggaagtc agattcttaa agagcatcct gttgaaaata ctcaattgca aaatgaaaag ctctatctct attatctcca aaatggaaga gacatgtatg tggaccaaga attagatatt aatcgtttaa gtgattatga tgtcgatcac attgttccac aaagtttcct taaagacgat tcaatagaca ataaggtctt aacgcgttct gataaaaatc gtggtaaatc ggataacgtt ccaagtgaag aagtagtcaa aaagatgaaa aactattgga gacaacttct aaacgccaag ttaatcactc aacgtaagtt tgataattta acgaaagctg aacgtggagg tttgagtgaa cttgataaag ctggttttat caaacgccaa ttggttgaaa ctcgccaaat cactaagcat gtggcacaaa ttttggatag tcgcatgaat actaaatacg atgaaaatga taaacttatt cgagaggtta aagtgattac cttaaaatct aaattagttt ctgacttccg aaaagatttc caattctata agtacgtga gattaacaat taccatcatg cccatgatgc gtatctaaat gccgtcgttg gaactgcttt gattaagaaa tatccaaaac ttgaatcgga gtttgtctat ggtgattata agtttatga tgttcgtaaa atgattgcta agtctgagca agaaataggc aaagcaaccg caaaatattt cttttactct aatatcatga acttcttcaa aacagaaatt acacttgcaa atggagagat tcgcaaacgc cctctaatcg aaactaatgg ggaaactgga gaaattgtct gggataaagg gcgagatttt gccacagtgc gcaaagtatt gtccatgccc caagtcaata ttgtcaagaa aacagaagta cagacaggcg gattctccaa ggagtcaatt ttaccaaaaa gaaattcgga caagcttatt gctcgtaaaa aagactggga tccaaaaaaa tatggtggtt ttgatagtcc aacggtagct tattcagtcc tagtggttgc taaggtggaa aaagggaaat cgaagaagtt aaaatccgtt aaagagttac tagggatcac aattatggaa agaagttcct ttgaaaaaaa tccgattgac
```

-continued ttttagaag ctaaaggata taaggaagtt aaaaaagact taatcattaa actacctaaa tatagtctttt ttgagttaga aaacggtcgt aaacggatgc tggctagtgc cggagaatta caaaaaggaa atgagctggc tctgccaagc aaatatgtga attttttata tttagctagt cattatgaaa agttgaaggg tagtccagaa gataacgaac aaaaacaatt gtttgtggag cagcataagc attatttaga tgagattatt gagcaaatca gtgaattttc taagcgtgtt attttagcag atgccaattt agataaagtt cttagtgcat ataacaaaca tagagacaaa ccaatacgtg aacaagcaga aaatattatt catttattta cgttgacgaa tcttggagct cccgctgctt ttaaatattt tgatacaaca attgatcgta aacgatatac gtctacaaaa gaagttttag atgccactct tatccatcaa tccatcactg gtctttatga aacacgcatt gatttgagtc agctaggagg tgactga (SEQ ID NO: 13)

ATGGATAAGAAATACTCAATAGGCTTAGATATCGGCACAAATAGCGTCGGATGGGCGGTGATCACTG

ATGAATATAAGGTTCCGTCTAAAAAGTTCAAGGTTCTGGGAAATACAGACCGCCACAGTATCAAAAA

AATCTTATAGGGGCTCTTTTATTTGACAGTGGAGAGACAGCGGAAGCGACTCGTCTCAAACGGACAG

CTCGTAGAAGGTATACACGTCGGAAGAATCGTATTTGTTATCTACAGGAGATTTTTTCAAATGAGATG

GCGAAAGTAGATGATAGTTTCTTTCATCGACTTGAAGAGTCTTTTTTGGTGGAAGAAGACAAGAAGCT

GAACGTCATCCTATTTTTGGAAATATAGTAGATGAAGTTGCTTATCATGAGAAATATCCAACTATCTAC

ATCTGCGAAAAAAATTGGTAGATTCTACTGATAAAGCGGATTTGCGCTTAATCTATTTGGCCTTAGCG

CATATGATTAAGTTTCGTGGTCATTTTTTGATTGAGGGAGATTTAAATCCTGATAATAGTGATGTGGAC

AAACTATTTATCCAGTTGGTACAAACCTACAATCAATTATTTGAAGAAAACCCTATTAACGCAAGTGGA

GTAGATGCTAAAGCGATTCTTTCTGCACGATTGAGTAAATCAAGACGATTAGAAAATCTCATTGCTCA

GCTCCCCGGTGAGAAGAAAAATGGCTTATTTGGGAATCTCATTGCTTTGTCATTGGGTTTGACCCCTA

ATTTTAAATCAAATTTTGATTTGGCAGAAGATGCTAAATTACAGCTTTCAAAAGATACTTACGATGATG

ATTTAGATAATTTATTGGCGCAAATTGGAGATCAATATGCTGATTTGTTTTTGGCAGCTAAGAATTTAT

CAGATGCTATTTTACTTTCAGATATCCTAAGAGTAAATACTGAAATAACTAAGGCTCCCCTATCAGCTT

CAATGATTAAACGCTACGATGAACATCATCAAGACTTGACTCTTTTAAAAGCTTTAGTTCGACAACAAC

TTCCAGAAAAGTATAAAGAAATCTTTTTTGATCAATCAAAAAACGGATATGCAGGTTATATTGATGGGG

GAGCTAGCCAAGAAGAATTTTATAAATTTATCAAACCAATTTTAGAAAAAATGGATGGTACTGAGGAAT

TATTGGTGAAACTAAATCGTGAAGATTTGCTGCGCAAGCAACGGACCTTTGACAACGGCTCTATTCCC

CATCAAATTCACTTGGGTGAGCTGCATGCTATTTTGAGAAGACAAGAAGACTTTTATCCATTTTTAAAA

GACAATCGTGAGAAGATTGAAAAAATCTTGACTTTTCGAATTCCTTATTATGTTGGTCCATTGGCGCGT

GGCAATAGTCGTTTTGCATGGATGACTCGGAAGTCTGAAGAAACAATTACCCCATGGAATTTTGAAGA

AGTTGTCGATAAAGGTGCTTCAGCTCAATCATTTATTGAACGCATGACAAACTTTGATAAAAATCTTCC

AAATGAAAAGTACTACCAAAACATAGTTTGCTTTATGAGTATTTTACGGTTTATAACGAATTGACAAA

GGTCAAATATGTTACTGAAGGAATGCGAAAACCAGCATTTCTTTCAGGTGAACAGAAGAAAGCCATTG

TTGATTTACTCTTCAAAACAAATCGAAAAGTAACCGTTAAGCAATTAAAAGAAGATTATTTCAAAAAAAT

AGAATGTTTTGATAGTGTTGAAATTTCAGGAGTTGAAGATAGATTTAATGCTTCATTAGGTACCTACCA

TGATTTGCTAAATTATTAAAGATAAAGATTTTTTGGATAATGAAGAAATGAAGATATCTTAGAGGAT

ATTGTTTTAACATTGACCTTATTTGAAGATAGGGAGATGATTGAGGAAAGACTTAAAACATATGCTCAC

CTCTTTGATGATAAGGTGATGAAACAGCTTAAACGTCGCCGTTATACTGGTTGGGGACGTTTGTCTCG

AAAATTGATTAATGGTATTAGGGATAAGCAATCTGGCAAAACAATATTAGATTTTTTGAAATCAGATGG

-continued

```
TTTTGCCAATCGCAATTTTATGCAGCTGATCCATGATGATAGTTTGACATTTAAAGAAGACATTCAAAA
AGCACAAGTGTCTGGACAAGGCGATAGTTTACATGAACATATTGCAAATTTAGCTGGTAGCCCTGCTA
TTAAAAAAGGTATTTTACAGACTGTAAAAGTTGTTGATGAATTGGTCAAAGTAATGGGGCGGCATAAG
CCAGAAAATATCGTTATTGAAATGGCACGTGAAAATCAGACAACTCAAAAGGGCCAGAAAAATTCGC
GAGAGCGTATGAAACGAATCGAAGAAGGTATCAAAGAATTAGGAAGTCAGATTCTTAAAGAGCATCC
TGTTGAAAATACTCAATTGCAAATGAAAAGCTCTATCTCTATTATCTCCAAAATGGAAGAGACATGTA
TGTGGACCAAGAATTAGATATTAATCGTTTAAGTGATTATGATGTCGATCACATTGTTCCACAAAGTTT
CCTTAAAGACGATTCAATAGACAATAAGGTCTTAACGCGTTCTGATAAAAATCGTGGTAAATCGGATA
ACGTTCCAAGTGAAGAAGTAGTCAAAAAGATGAAAAACTATTGGAGACAACTTCTAAACGCCAAGTTA
ATCACTCAACGTAAGTTTGATAATTTAACGAAAGCTGAACGTGGAGGTTTGAGTGAACTTGATAAAGC
TGGTTTTATCAAACGCCAATTGGTTGAAACTCGCCAAATCACTAAGCATGTGGCACAAATTTTGGATA
GTCGCATGAATACTAAATACGATGAAAATGATAAACTTATTCGAGAGGTTAAAGTGATTACCTTAAAAT
CTAAATTAGTTTCTGACTTCCGAAAAGATTTCCAATTCTATAAAGTACGTGAGATTAACAATTACCATC
ATGCCCATGATGCGTATCTAAATGCCGTCGTTGGAACTGCTTTGATTAAGAAATATCCAAAACTTGAA
TCGGAGTTTGTCTATGGTGATTATAAAGTTTATGATGTTCGTAAAATGATTGCTAAGTCTGAGCAAGAA
ATAGGCAAAGCAACCGCAAAATATTTCTTTTACTCTAATATCATGAACTTCTTCAAAACAGAAATTACA
CTTGCAAATGGAGAGATTCGCAAACGCCCTCTAATCGAAACTAATGGGGAAACTGGAGAAATTGTCT
GGGATAAAGGGCGAGATTTTGCCACAGTGCGCAAAGTATTGTCCATGCCCCAAGTCAATATTGTCAA
GAAAACAGAAGTACAGACAGGCGGATTCTCCAAGGAGTCAATTTTACCAAAAGAAATTCGGACAAG
CTTATTGCTCGTAAAAAAGACTGGGATCCAAAAAAATATGGTGGTTTTGATAGTCCAACGGTAGCTTA
TTCAGTCCTAGTGGTTGCTAAGGTGGAAAAAGGGAAATCGAAGAAGTTAAAATCCGTTAAAGAGTTAC
TAGGGATCACAATTATGGAAAGAAGTTCCTTTGAAAAAAATCCGATTGACTTTTTAGAAGCTAAAGGAT
ATAAGGAAGTTAAAAAAGACTTAATCATTAAACTACCTAAATATAGTCTTTTTGAGTTAGAAAACGGTC
GTAAACGGATGCTGGCTAGTGCCGGAGAATTACAAAAAGGAAATGAGCTGGCTCTGCCAAGCAAATA
TGTGAATTTTTTATATTTAGCTAGTCATTATGAAAAGTTGAAGGGTAGTCCAGAAGATAACGAACAAAA
ACAATTGTTTGTGGAGCAGCATAAGCATTATTTAGATGAGATTATTGAGCAAATCAGTGAATTTTCTAA
GCGTGTTATTTTAGCAGATGCCAATTTAGATAAAGTTCTTAGTGCATATAACAAACATAGAGACAAACC
AATACGTGAACAAGCAGAAAATATTATTCATTTATTTACGTTGACGAATCTTGGAGCTCCCGCTGCTTT
TAAATATTTTGATACAACAATTGATCGTAAACGATATACGTCTACAAAAGAAGTTTTAGATGCCACTCT
ATCCATCAATCCATCACTGGTCTTTATGAAACACGCATTGATTTGAGTCAGCTAGGAGGTGACTGA.
```

Exemplary nucleases include but are not limited to those having SEQ ID NO:14 or 15, or a protein with at least 80%, 82%, 85%, 87%, 90%, 92%, 95%, 97%, 98%, 99% or 100% amino acid sequence identity to a nuclease that is encoded by SEQ ID NO:14 or 15:

```
                                         (SEQ ID NO: 14)
mkekyilgld lgitsvgygi infetkkiid agvrlfpean vdnnegrrsk rgsrrlkrrr ihrlervkll lteydlinke qiptsnnpyq irvkglseil skdelaiall hlakrrgihn invssededa snelstkeqi nrnnkllkdk yvcevqlqrt kegqirgekn rfkttdilke idqlikvqkd yhnldidfin qykeivetrr eyfegpgqgs pfgwngdlkk wyemimghct ylpqelrsvk yaysadlfna lndlnnliiq rdnsekleyh ekyhiienvf kqkkkptlkq iakeigvnpe dikgyritks gtpqftefkl yhdlksivfd ksileneail dqiaeiltiy qdeqsikeel nklpeilneq dkaeiaklig yngthrlslk cihlineelw qtsrnqmeif nylnikpnkv dlseqnkipk dmvndfilsp vvkrtfiqsi nvinkvieky gipediiiel arennsddrk kfinnlqkkn eatrkrinei igqtgnqnak rivekirlhd qqegkclysl esialmdlln npqnyevdhi
```

```
iprsvafdns ihnkvlvkqi enskkgnrtp yqylnssdak lsynqfkqhi lnlskskdri skkkkdylle erdinkfevq kefinrnlvd tryatrelts ylkayfsann mdvkvkting sftnhlrkvw rfdkyrnhgy khhaedalii anadflfken kklqnankil ekptienntk kvtvekeedy nnvfetpklv edikqyrdyk fshrvdkkpn rqlindtlys trmkdehdyi vqtitdiygk drtnlkkqfn knpekflmyq ndpktfekls iimkqysdek kplakyyeet geyltkyskk nngpivkkik llgnkvgnhl dvtnkyenst kklvklsikn yrfdvyltek gykfvtiayl nvfkkdnyyy ipkdkyqelk ekkkikdtdq fiasfykndl iklngdlyki igvnsddrni ieldyydiky kdyceinnik geprikktig kktesiekft tdvlgnlylh stekapqlif krgl (SEQ ID NO: 15)
mnkpysigld igtnsvgwsi itddykvpak kmrvlgntdk eyikknliga llfdggntas drrlkrtarr rytrrrnril ylqeifaeem skvddsffhr ledsflvedd krgskypifa tmqeekdyhe kfptiyhlrk eladkkekad lrlfylalah iikfrghfli eddsfdvrnt diqrqyqafl eifdttfenn hllsqnidve giltdkisks akkdrilaqy pnqkstgifa eflklivgnq adfkkhfnle dktplqfakd sydedlenll gqigdefadl fsvakklyds vllsgiltvt distkaplsa smiqrydehr edlkqlkqfv kaslpekyqe iftdsskdgy agyiegktnq gafykylskl ltkqegseyf lekiknedfl rkqrtfdngs iphqvhltel kaiirrqsey ypflkenldr iekiltfrip yyvgplarek sdfawmtrkt ddsirpwnfe elvdkeasae afihrmtnnd lylpeekvlp khsliyekft vyneltkvry kneqgetyff dsnikqeifd gvfkehrkvs kkklldflak eyeefrivdv igldkenkaf naslgtyhdl kkildkdfld npdnesiled ivqtltlfed remikkrlen ykdlftesql kklyrrhytg wgrlsaklin girdkesqkt ildyliddgk snrnfmqlih ddglsfksii skaqagshsd nlkevvgela gspaikkgil qslkivdelv kvmgyepeqi vvemarenqt tnqgrrnsrq rykliddgvk nlasdlngni lkeyptdnqa lqnerlflyy lqngrdmytg kaldidnlsq ydidhiipqa fikddsidnr vlvssaknrg ksddvpslei vkdckvfwkk lldaklmsqr kydnltkaer ggltsddkar fiqrqlvetr qitkhvaril derfnnelds kgrrirkvki vtlksnlvsn frkefgfyki revnnyhhah daylnavvak ailtkypqle pefvygdypk ynsyktrksa teklffysni mnffktkvtl adgtvvvkdd ievnndtgei vwdkkkhfat
```

```
vrkvisypqv nivkkteiqt ggfskesila hgnsdklipr ktkdiyldpk kyggfdspiv aysvlvvadi kkgkaqklkt vtellgitim ersrfeknps afleskgyln irddklmilp kyslfeleng rrrllasage lqkgnelalp tqfmkflyla srynelkgkp eeieqkqefv vqhvsyfddi lqiindfsnr viladanlek inklyqdnke nisvdelann iinlftftsl gapaafkffd kivdrkryts tkevlnstli hqsitglyet ridlgklged.
```

Thus, in one embodiment, the ds mRNA encodes a nuclease such as a Cas9 protein e.g., one having SEQ ID NO:14 or 15, or a protein with at least 80%, 82%, 85%, 87%, 90%, 92%, 95%, 97%, 98%, 99% or 100% amino acid sequence identity to a nuclease that is encoded by SEQ ID NO:14 or 15.

Example 3

Influence of Reverse mRNA Length on Gene Expression

Figure 6:
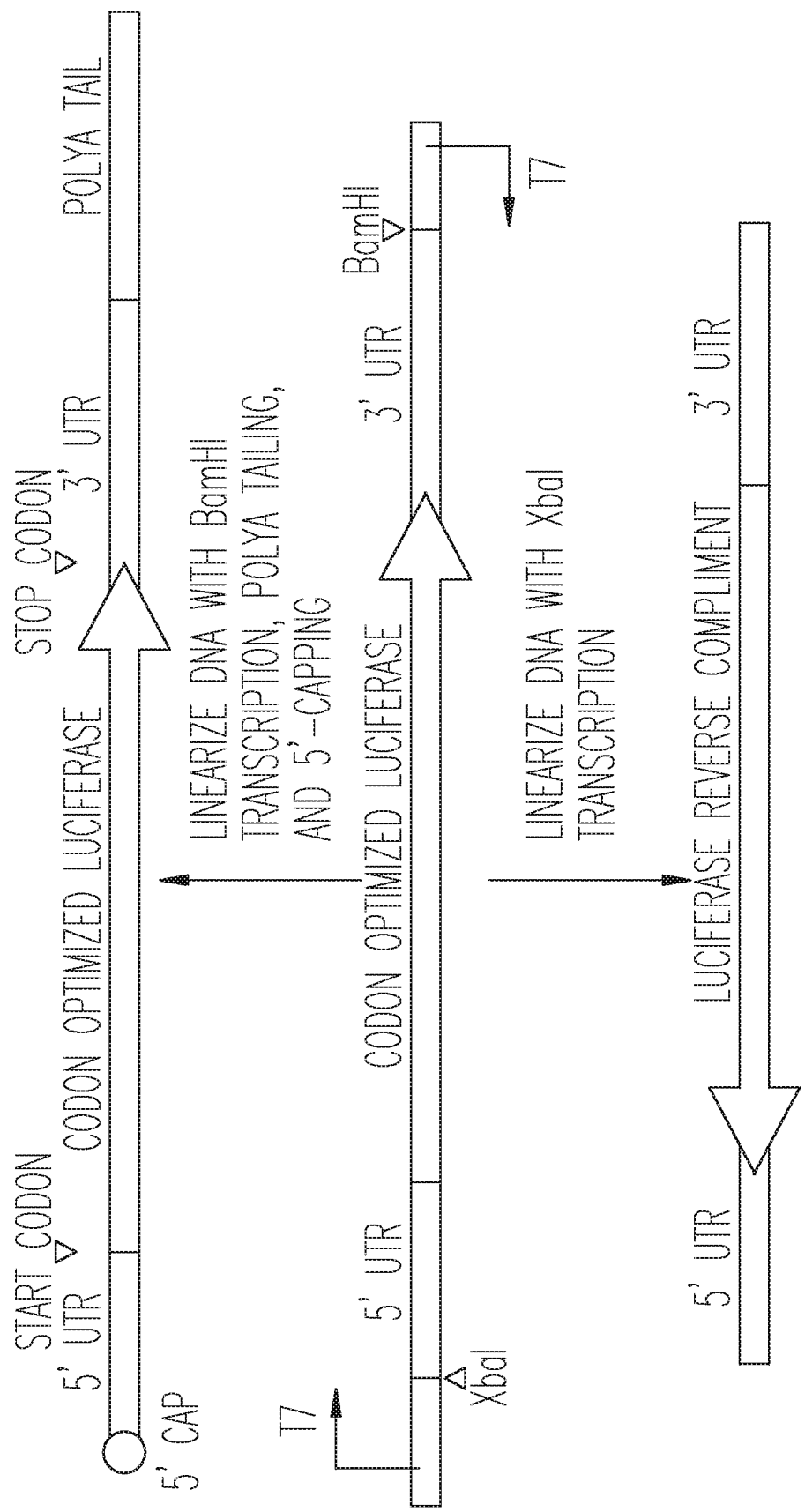
FIG. 6. Biosynthesis of ds mRNA. The preparation of forward and reverse strand mRNA is illustrated. The length or reverse mRNA controlled by the T7 transcriptional start site to the 5' transcription enzyme stop site. Xba1 was used as the full length reverse mRNA.
Figure 7:
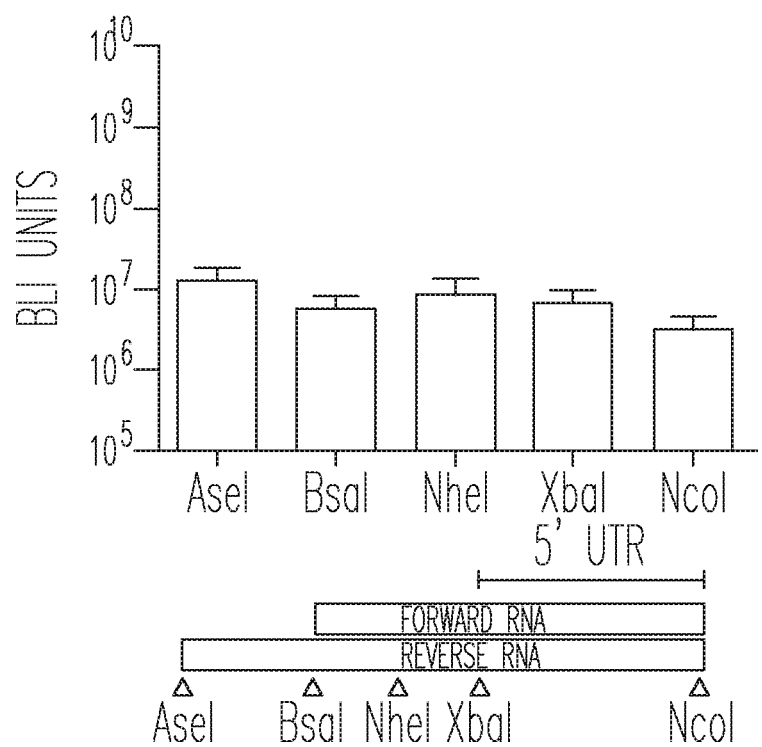
FIG. 7. Gene Expression of ds mRNA. The influence of reverse mRNA length on gene expression of ds mRNA in mice is illustrated.

The influence of the reverse strand length was analyzed by preparing reverse strand mRNA using plasmid DNA linearized with different restriction enzymes to increase or decrease the length of mRNA. XbaI was used to form the full length reverse mRNA that hybridizes with 3'UTR, coding region, and 5' UTR in forward mRNA (FIG. 6). NheI, BsaI and AseI were used to produce progressively longer reverse mRNA that extended beyond the 5' UTR on forward mRNA (FIG. 7). NcoI was used to prepare a shorter reverse mRNA that hybridized with forward mRNA to expose the 5' UTR (FIG. 7). RNA transcripts (sense strand) may be "tailed" with polyA sequences after being transcribed from the vector or the vector can include sequences that result in polyA tails on transcripts obtained from the vector. Each reverse mRNA was hybridized with forward mRNA to form ds mRNA. The resulting ds mRNAs were then combined with PEG-peptide and a 1 μg dose was administered via the tail vein of triplicate mice. At five minutes post administration, mice were administered a hydrodynamic dose of 1.9 mL of saline in 5 seconds via the tail vein. After 24 hours the mice were dosed i.p. with luciferin and the level of luciferase in liver was determined by quantitative bioluminescence imaging on an IVIS image (FIG. 7). The results established that extending the length of the reverse mRNA relative to XbaI had a negligible result on the level of gene expression (FIG. 7). Similar, decreasing the length to fully expose the 5' UTR did not significantly influence the level of gene expression (FIG. 7).

Figure 8:
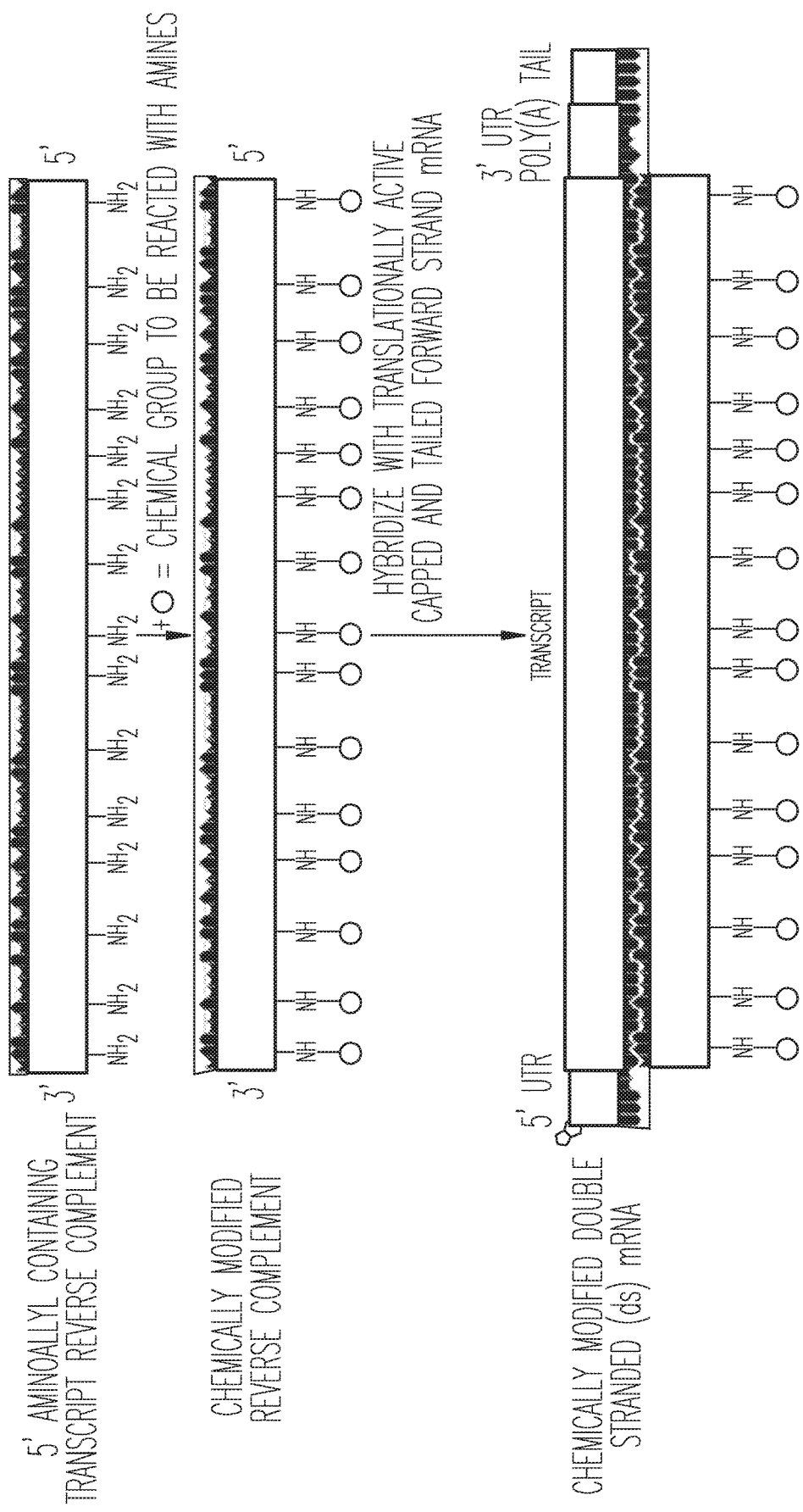
FIG. 8. Generation of Chemically modified ds mRNA.
Figure 9:
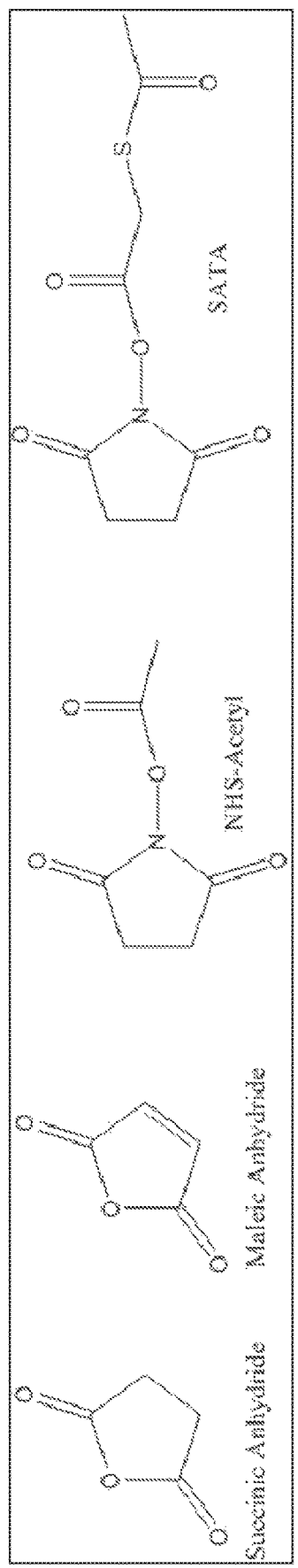
FIG. 9. Reagents Used to Chemically Modify 5' amino allyl Reverse mRNA.

Chemically modified reverse mRNA was biosynthesized using 5' amino allyl modified uridine or cytidine to replace each U or C, and both U and C, to incorporate multiple primary amines in the reverse mRNA strand (FIG. 8). Incorporation of 5'aminoallyl uridine and/or cytidine during in vitro transcription is well/tolerated, resulting in full-length (aa-U Rev-, aa-C Rev- or aa-U/C Rev-) RNA with approximately 450 or 900 amines. Reverse strand primary amines May be used as a chemical handle for functionalization with acetyl, maleic acid, succinic acid, thiol-acetate, and PEG. Primary amines were then fully functionalized using anhydrides and N-hydroxysuccinamide esters to generate chemically functionalized reverse mRNA (FIG. 9).

Hybridization of chemically functionalized reverse mRNA with forward mRNA resulted in chemically modified ds mRNA. Biological testing of chemically modified ds mRNA included testing for increased metabolic stability and functional translation to express luciferase in vivo.

5' amino allyl uridine and cytidine modified ds mRNA demonstrated increased RNAse resistance relative to unmodified ds mRNA. However, 5' amino allyl modified ds mRNA was inactive when tested for translation into luciferase. Alternatively, chemical modification of reverse mRNA with the amino reactive agents in FIG. 9 resulted in ds mRNAs that were partially translationally active in expressing luciferase. The greatest translational activity resulted from modification of 5-aminoallyl uridine with acetyl.

Figure 10:
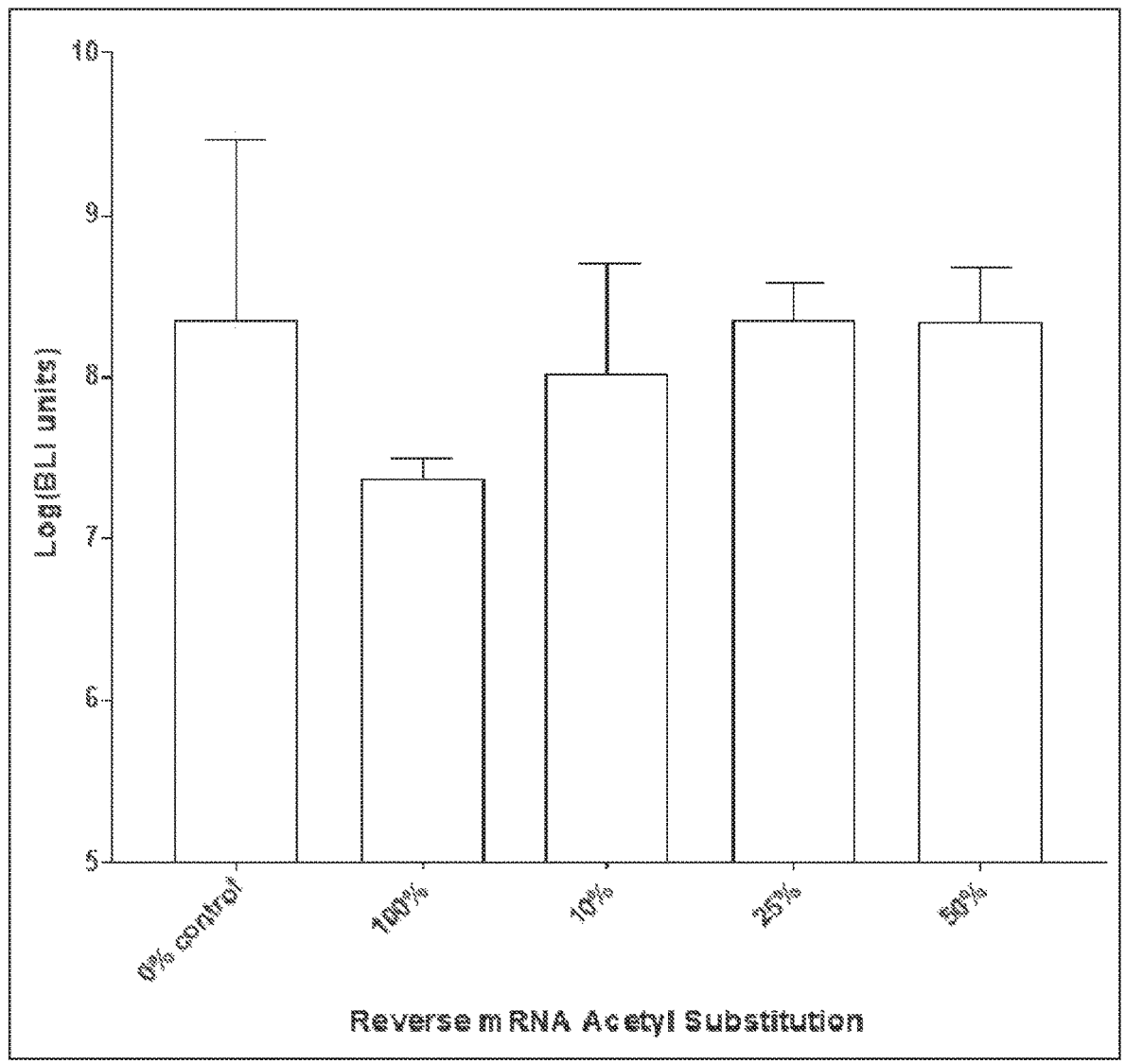
FIG. 10. In Vivo Expression of Luciferase from Chemically Modified ds mRNA. The level of luciferase expression for fully acetylated reverse mRNA with varying 5' amino allyl uridine modification is illustrated.

The magnitude of luciferase expression in liver was compared following hydrodynamic dosing of 1 µg of chemically modified ds mRNA (FIG. 10) into the tail vein of mice. Fully acetylated 100% 5' amino allyl modified reverse mRNA resulted in a 10-fold decrease of expression relative to control. Substitution of 10-50% of reverse mRNA uridine with 5' amino allyl uridine followed by acetylation resulted in gene expression that was indistinguishable from control.

The results establish that chemical functionalization of ds mRNA can produce translationally active ds mRNA. These or further modifications may produce translationally active ds mRNA with increased metabolic stability.

REFERENCES

Al Dosari et al., Hydrodynamic Delivery, in Advances in Genetics. Academic Press. p. 65 (2005).
Andrianaivo et al., J. Gene Med., 6:877 (2004).
Avci-Adali et al., J. Biol. Eng., 8:8 (2014).
Cheng et al., Biomaterials, 33:6868 (2012).
Chuah et al., J. Thromb. Haemost., 11:99 (2013).
Debus et al., J. Control Release. 148:334 (2010).
Deering et al., Expert Opin. Drug Deliv., 11:885 (2014).
Hodges et al., Expert Opin. Biol. Ther., 2:911 (2003).
Hu et al., ACS Nano, 7:5376 (2013).
Kariko et al., Mol. Ther., 29:948 (2012).
Kormann et al., Nat. Biotechnol., 22:154 (2011).
Lenter et al., Pharmaceutical Research, 21:683 (2004).
Liu et al., Gene Ther., 6:1258 (1999).
Malone et al., Proc. Natl. Acad. Sci. USA, 86:6077 (1989).
McCaffrey et al., Mol. Ther., 5:676 (2002).
Perche et al., Nanomedicine, 7:445 (2011).
Phua et al., J. Control Release, 166:227 (2013).
Phua et al., Sci. Rep., 4:5128 (2014).
Pun et al., Bioconjugate Chemistry, 13:630 (2002).
Read et al., in Advances in Genetics, J. C. Hall, J. C. Dunlap, T. Friedmann, and V. van Heyningen, Editors. Academic Press. p. 19-46 (2005).
Richard et al., Gene Ther., 0.1:746 (2009).
Sahin et al., Nat. Rev. Drug Discov., 13:759 (2014).
Schlake et al., RNA Biol., 9:1319 (2012).
Uchida et al., PLoS One, 8:e56220 (2013).
Wang et al., Mol. Ther., 21:358 (2013).
Wilber at al., Mol. Ther., 13:625 (2006).
Wolff et al., Science, 247:1465 (1990).
Wooddell et al., Mol. Ther., 21:973 (2013).
Wu et al., J. Bio. Chem., 263:14621 (1988).
Zangi et al., Nat. Biotechnol., 3:898 (2013).
Zhang et al., Gene Ther., 11:675 (2004).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

SEQUENCE LISTING

```
<160> NUMBER OF SEQ ID NOS: 15

<210> SEQ ID NO 1
<211> LENGTH: 1524
<212> TYPE: DNA
<213> ORGANISM: Artificial Sequence
<220> FEATURE:
<223> OTHER INFORMATION: A synthetic nucleic acid sequence

<400> SEQUENCE: 1
agcagacaga ggactctcat taaggaaggt gtcctgtgcc ctgaccctac aagatgccaa      60
gagaagatgc tcacttcatc tatggttacc ccaagaaggg gcacggccac tcttacacca     120
cggctgaaga ggccgctggg atcggcatcc tgacagtgat cctgggagtc ttactgctca     180
tcggctgttg gtattgtaga agacgaaatg gatacagagc cttgatggat aaaagtcttc     240
atgttggcac tcaatgtgcc ttaacaagaa gatgcccaca agaagggttt gatcatcggg     300
acagcaaagt gtctcttcaa gagaaaaact gtgaacctgt ggttcccaat gctccacctg     360
cttatgagaa actctctgca gaacagtcac caccaccttta ttcaccttaa gagccagcga     420
gacacctgag acatgctgaa attatttctc tcacactttt gcttgaattt aatacagaca     480
tctaatgttc tcctttggaa tggtgtagga aaaatgcaag ccatctctaa taataagtca     540
gtgttaaaat tttagtaggt ccgctagcag tactaatcat gtgaggaaat gatgagaaat     600
attaaattgg gaaaactcca tcaataaatg ttgcaatgca tgatactatc tgtgccagag     660
```

| | |
|---|---|
| gtaatgttag taaatccatg gtgttatttt ctgagagaca gaattcaagt gggtattctg | 720 |
| gggccatcca atttctcttt acttgaaatt tggctaataa caaactagtc aggttttcga | 780 |
| accttgaccg acatgaactg tacacagaat tgttccagta ctatggagtg ctcacaaagg | 840 |
| atacttttac aggttaagac aaagggttga ctggcctatt tatctgatca agaacatgtc | 900 |
| agcaatgtct ctttgtgctc taaaattcta ttatactaca ataatatatt gtaaagatcc | 960 |
| tatagctctt ttttttttgag atggagtttc gcttttgttg cccaggctgg agtgcaatgg | 1020 |
| cgcgatcttg gctcaccata acctccgcct cccaggttca agcaattctc ctgccttagc | 1080 |
| ctcctgagta gctgggatta caggcgtgcg ccactatgcc tgactaattt tgtagttta | 1140 |
| gtagagacgg ggtttctcca tgttggtcag gctggtctca aactcctgac ctcaggtgat | 1200 |
| ctgcccgcct cagcctccca aagtgctgga attacaggcg tgagccacca cgcctggctg | 1260 |
| gatcctatat cttaggtaag acatataacg cagtctaatt acatttcact tcaaggctca | 1320 |
| atgctattct aactaatgac aagtattttc tactaaacca gaaattggta gaaggattta | 1380 |
| aataagtaaa agctactatg tactgcctta gtgctgatgc ctgtgtactg ccttaaatgt | 1440 |
| acctatggca atttagctct cttgggttcc caaatccctc tcacaagaat gtgcagaaga | 1500 |
| aatcataaag gatcagagat tctg | 1524 |

<210> SEQ ID NO 2
<211> LENGTH: 2384
<212> TYPE: DNA
<213> ORGANISM: Artificial Sequence
<220> FEATURE:
<223> OTHER INFORMATION: A synthetic nucleic acid sequence

<400> SEQUENCE: 2

| | |
|---|---|
| tattgagttc ttcaaacatt gtagcctctt tatggtctct gagaaataac taccttaaac | 60 |
| ccataatctt taatacttcc taaactttct taataagaga agctctattc ctgacactac | 120 |
| ctctcatttg caaggtcaaa tcatcattag ttttgtagtc tattaactgg gtttgcttag | 180 |
| gtcaggcatt attattacta accttattgt taatattcta accataagaa ttaaactatt | 240 |
| aatggtgaat agagtttttc actttaacat aggcctatcc cactggtggg atacgagcca | 300 |
| attcgaaaga aaagtcagtc atgtgctttt cagaggatga agcttaaga taaagactaa | 360 |
| aagtgtttga tgctggaggt gggagtggta ttatataggt ctcagccaag acatgtgata | 420 |
| atcactgtag tagtagctgg aaagagaaat ctgtgactcc aattagccag ttcctgcaga | 480 |
| ccttgtgagg actagaggaa gaatgctcct ggctgttttg tactgcctgc tgtggagttt | 540 |
| ccagacctcc gctggccatt tccctagagc ctgtgtctcc tctaagaacc tgatggagaa | 600 |
| ggaatgctgt ccaccgtgga gcggggacag gagtccctgt ggccagcttt caggcagagg | 660 |
| ttcctgtcag aatatccttc tgtccaatgc accacttggg cctcaatttc ccttcacagg | 720 |
| ggtggatgac cggagtcgt ggccttccgt cttttataat aggacctgcc agtgctctgg | 780 |
| caacttcatg ggattcaact gtggaaactg caagtttggc ttttggggac caaactgcac | 840 |
| agagagacga ctcttggtga aagaaacat cttcgatttg agtgccccag agaaggacaa | 900 |
| attttttgcc tacctcactt tagcaaagca taccatcagc tcagactatg tcatccccat | 960 |
| agggacctat ggccaaatga aaatggatc aacacccatg tttaacgaca tcaatattta | 1020 |
| tgacctcttt gtctggatgc attattatgt gtcaatggat gcactgcttg ggggatctga | 1080 |
| aatctggaga gacattgatt ttgcccatga agcaccagct tttctgcctt ggcatagact | 1140 |
| cttcttgttg cggtgggaac aagaaatcca gaagctgaca ggagatgaaa acttcactat | 1200 |

```
tccatattgg gactggcggg atgcagaaaa gtgtgacatt tgcacagatg agtacatggg    1260
aggtcagcac cccacaaatc ctaacttact cagcccagca tcattcttct cctcttggca    1320
gattgtctgt agccgattgg aggagtacaa cagccatcag tctttatgca atggaacgcc    1380
cgagggacct ttacggcgta atcctggaaa ccatgacaaa tccagaaccc caaggctccc    1440
ctcttcagct gatgtagaat tttgcctgag tttgacccaa tatgaatctg gttccatgga    1500
taaagctgcc aatttcagct ttagaaatac actggaagga tttgctagtc cacttactgg    1560
gatagcggat gcctctcaaa gcagcatgca caatgccttg cacatctata tgaatggaac    1620
aatgtcccag gtacagggat ctgccaacga tcctatcttc cttcttcacc atgcatttgt    1680
tgacagtatt tttgagcagt ggctccgaag gcaccgtcct cttcaagaag tttatccaga    1740
agccaatgca cccattggac ataaccggga atcctacatg gttccttta taccactgta    1800 cagaaatggt gatttctta tttcatccaa agatctgggc tatgactata gctatctaca    1860
agattcagac ccagactctt ttcaagacta cattaagtcc tatttggaac aagcgagtcg    1920
gatctggtca tggctccttg gggcggcgat ggtaggggcc gtcctcactg ccctgctggc    1980
agggcttgtg agcttgctgt gtcgtcacaa gagaaagcag cttcctgaag aaaagcagcc    2040
actcctcatg gagaaagagg attaccacag cttgtatcag agccatttat aaaaggctta    2100
ggcaatagag tagggccaaa aagcctgacc tcactctaac tcaaagtaat gtccaggttc    2160
ccagagaata tctgctggta ttttctgta aagaccattt gcaaaattgt aacctaatac    2220
aaagtgtagc cttcttccaa ctcaggtaga acacacctgt ctttgtcttg ctgttttcac    2280
tcagcccttt taacattttc ccctaagccc atatgtctaa ggaaaggatg ctatttggta    2340
atgaggaact gttatttgta tgtgaattaa agtgctctta tttt                    2384
```

<210> SEQ ID NO 3
<211> LENGTH: 1580
<212> TYPE: DNA
<213> ORGANISM: Artificial Sequence
<220> FEATURE:
<223> OTHER INFORMATION: A synthetic nucleic acid sequence

<400> SEQUENCE: 3

```
cccacactcc cgcctgttgc cctgaccaga gtcatcatgc ctcttgagca gaggagtcag     60
cactgcaagc ctgaagaagg ccttgaggcc cgaggagagg ccctgggcct ggtgggtgcg    120
caggctcctg ctactgagga gcaggaggct gcctcctcct cttctactct agttgaagtc    180
accctggggg aggtgcctgc tgccgagtca ccagatcctc cccagagtcc tcagggagcc    240
tccagcctcc ccactaccat gaactaccct ctctggagcc aatcctatga ggactccagc    300
aaccaagaag aggaggggcc aagcaccttc cctgacctgg agtccgagtt ccaagcagca    360
ctcagtagga aggtggccga gttggttcat tttctgctcc tcaagtatcg agccagggag    420
ccggtcacaa aggcagaaat gctggggagt gtcgtcggaa attggcagta tttctttcct    480
gtgatcttca gcaaagcttt cagttccttg cagctggtct ttggcatcga gctgatggaa    540
gtggacccca tcggccactt gtacatcttt gccacctgcc tgggcctctc ctacgatggc    600
ctgctgggtg acaatcagat catgcccaag gcaggcctcc tgataatcgt cctggccata    660
atcgcaagag agggcgactg tgcccctgag gagaaatct ggaggagct gagtgtgtta    720 gaggtgtttg aggggaggga agacagtatc ttggggatc caagaagct gctcacccaa    780 catttcgtgc aggaaaacta cctggagtac cggcaggtcc ccggcagtga tcctgcatgt    840
```

```
tatgaattcc tgtggggtcc aagggccctc gttgaaacca gctatgtgaa agtcctgcac    900
catatggtaa agatcagtgg aggacctcac atttcctacc caccccctgca tgagtgggtt    960
ttgagagagg gggaagagtg agtctgagca cgagttgcag ccagggccag tgggagggg    1020
tctgggccag tgcaccttcc ggggccgcat cccttagttt ccactgcctc ctgtgacgtg   1080
aggcccattc ttcactcttt gaagcgagca gtcagcattc ttagtagtgg gtttctgttc   1140
tgttggatga ctttgagatt attctttgtt tcctgttgga gttgttcaaa tgttcctttt   1200
aacggatggt tgaatgagcg tcagcatcca ggtttatgaa tgacagtagt cacacatagt   1260
gctgtttata tagtttagga gtaagggtct tgttttttac tcaaattggg aaatccattc   1320
cattttgtga attgtgacat aataatagca gtggtaaaag tatttgctta aaattgtgag   1380
cgaattagca ataacataca tgagataact caagaaatca aaagatagtt gattcttgcc   1440
ttgtacctca atctattctg taaaattaaa caaatatgca aaccaggatt tccttgactt   1500
ctttgagaat gcaagcgaaa ttaaatctga ataaataatt cttcctcttc aaaaaaaaaa   1560
aaaaaaaaaa aaaggccaca                                               1580

<210> SEQ ID NO 4
<211> LENGTH: 1629
<212> TYPE: DNA
<213> ORGANISM: Artificial Sequence
<220> FEATURE:
<223> OTHER INFORMATION: A synthetic nucleic acid sequence

<400> SEQUENCE: 4
gttggcagag gtggcggcgg cggcatgggt gccccgacgt tgccccctgc ctggcagccc     60
tttctcaagg accaccgcat ctctacattc aagaactggc ccttcttgga gggctgcgcc    120
tgcaccccgg agcggatggc cgaggctggc ttcatccact gccccactga gaacgagcca    180
gacttggccc agtgtttctt ctgcttcaag gagctggaag gctgggagcc agatgacgac    240
cccatagagg aacataaaaa gcattcgtcc ggttgcgctt tcctttctgt caagaagcag    300
tttgaagaat taaccctttgg tgaatttttg aaactggaca gagaaagagc caagaacaaa    360
attgcaaagg aaaccaacaa taagaagaaa gaatttgagg aaactgcgaa gaaagtgcgc    420
cgtgccatcg agcagctggc tgccatggat tgaggcctct ggccggagct gcctggtccc    480
agagtggctg caccacttcc agggtttatt ccctggtgcc accagccttc ctgtgggccc    540
cttagcaatg tcttaggaaa ggagatcaac attttcaaat tagatgtttc aactgtgctc    600
ttgttttgtc ttgaaagtgg caccagaggt gcttctgcct gtgcagcggg tgctgctggt    660
aacagtggct gcttctctct ctctctctct tttttggggg ctcattttttg ctgttttgat    720
tcccgggctt accaggtgag aagtgaggga ggaagaaggc agtgtccctt ttgctagagc    780
tgacagcttt gttcgcgtgg gcagagcctt ccacagtgaa tgtgtctgga cctcatgttg    840
ttgaggctgt cacagtcctg agtgtggact tggcaggtgc ctgttgaatc tgagctgcag    900
gttccttatc tgtcacacct gtgcctcctc agaggacagt ttttttgttg ttgtgttttt    960
ttgttttttt tttttggta gatgcatgac ttgtgtgtga tgagagaatg gagacagagt   1020
ccctggctcc tctactgttt aacaacatgg ctttcttatt ttgttgaat tgttaattca   1080
cagaatagca caaactacaa ttaaaactaa gcacaaagcc attctaagtc attggggaaa   1140
cggggtgaac ttcaggtgga tgaggagaca gaatagagtg ataggaagcg tctggcagat   1200
actccttttg ccactgctgt gtgattagac aggcccagtg agccgcgggg cacatgctgg   1260
ccgctcctcc ctcagaaaaa ggcagtggcc taaatccttt ttaaatgact tggctcgatg   1320
```

| | |
|---|---|
| ctgtggggga ctggctgggc tgctgcaggc cgtgtgtctg tcagcccaac cttcacatct | 1380 |
| gtcacgttct ccacacgggg gagagacgca gtccgcccag gtccccgctt tctttggagg | 1440 |
| cagcagctcc cgcagggctg aagtctggcg taagatgatg gatttgattc gccctcctcc | 1500 |
| ctgtcataga gctgcagggt ggattgttac agcttcgctg gaaacctctg gaggtcatct | 1560 |
| cggctgttcc tgagaaataa aaagcctgtc atttcaaaca caaaaaaaaa aaaaaaaaa | 1620 |
| aaaaaaaaa | 1629 |

<210> SEQ ID NO 5
<211> LENGTH: 1725
<212> TYPE: DNA
<213> ORGANISM: Artificial Sequence
<220> FEATURE:
<223> OTHER INFORMATION: A synthetic nucleic acid sequence

<400> SEQUENCE: 5

| | |
|---|---|
| atggagctgc tgatccacag gttaagtgca atcttcctaa ctcttgctat taatgcattg | 60 |
| tacctcacct caagtcagaa cataactgag gagttttacc aatcgacatg tagtgcagtt | 120 |
| agcagaggtt attttagtgc tttaagaaca ggttggtata ccagtgtcat aacaatagaa | 180 |
| ttaagtaata taaagaaac caaatgcaat ggaactgaca ctaaagtaaa acttataaaa | 240 |
| caagaattag ataagtataa gaatgcagtg acagaattac agctactat gcaaaacaca | 300 |
| ccagctgcca acaaccgggc cagaagagaa gcaccacagt atatgaacta caatcaat | 360 |
| accactaaaa acctaaatgt atcaataagc aagaagagga aacgaagatt tctgggcttc | 420 |
| ttgttaggtg taggatctgc aatagcaagt ggtatagctg tatccaaagt tctacacctt | 480 |
| gaaggagaag tgaacaagat caaaaatgct ttgttatcta caaacaaagc tgtagtcagt | 540 |
| ctatcaaatg gggtcagtgt tttaaccagc aaagtgttag atctcaagaa ttacataaat | 600 |
| aaccaattat tacccatagt aaatcaacag agctgtcgca tctccaacat tgaaacagtt | 660 |
| atagaattcc agcagaagaa cagcagattg ttggaaatca acagagaatt cagtgtcaat | 720 |
| gcaggtgtaa caacaccttt aagcacttac atgttaacaa acagtgagtt actatcattg | 780 |
| atcaatgata tgcctataac aaatgatcag aaaaaattaa tgtcaagcaa tgttcagata | 840 |
| gtaaggcaac aaagttattc tatcatgtct ataataaagg aagaagtcct tgcatatgtt | 900 |
| gtacagctac ctatctatgg tgtaatagat acaccttgct ggaaattaca cacatcacct | 960 |
| ctatgcacca ccaacatcaa agaaggatca aatatttgtt taacaaggac tgatagagga | 1020 |
| tggtattgtg ataatgcagg atcagtatcc ttctttccac aggctgacac ttgtaaagta | 1080 |
| cagtccaatc gagtattttg tgacactatg aacagtttga cattaccaag tgaagtcagc | 1140 |
| ctttgtaaca ctgacatatt caattccaag tatgactgca aaattatgac atcaaaaaca | 1200 |
| gacataagca gctcagtaat tacttctctt ggagctatag tgtcatgcta tggtaaaact | 1260 |
| aaatgcactg catccaacaa aaatcgtggg attataaaga cattttctaa tggttgtgac | 1320 |
| tatgtgtcaa acaaggagt agatactgtg tcagtgggca cactttata ctatgtaaac | 1380 |
| aagctggaag gcaagaacct ttatgtaaaa ggggaaccta ataaaatta ctatgacccct | 1440 |
| ctagtgtttc cttctgatga gtttgatgca tcaatatctc aagtcaatga aaaaatcaat | 1500 |
| caaagtttag cttttattcg tagatctgat gaattactac ataatgtaaa tactggcaaa | 1560 |
| tctactacaa atattatgat aactacaatt attatagtaa tcattgtagt attgttatca | 1620 |
| ttaatagcta ttggtttgct gttgtattgc aaagccaaaa acacaccagt tacactaagc | 1680 | aaagaccaac taagtggaat caataatatt gcattcagca aatag         1725

<210> SEQ ID NO 6
<211> LENGTH: 3681
<212> TYPE: DNA
<213> ORGANISM: Artificial Sequence
<220> FEATURE:
<223> OTHER INFORMATION: A synthetic nucleic acid sequence

<400> SEQUENCE: 6
gtgagcagaa tccatgtgca aggagagcag gcagttcagg acgagggtga gctggtctct    60
gcaggtttag tgctgtggca ctgtgcctgg tatatgctcc cggcaacttc tcctgactct   120
gccttcagac gagacttgga agacagtcac atctcagcag ctcctctgcc gttatccagc   180
ctgcctctga caagaaccca atgcccaacc ctaggccagc caagcctatg gctccttcct   240
tggcccttgg cccatcccca ggagtcttgc caagctggaa gactgcaccc aagggctcag   300
aacttctagg gaccaggggc tctggggac ccttccaagg tcgggacctg cgaagtgggg     360
cccacacctc ttcttccttg aaccccctgc caccatccca gctgcagctg cctacagtgc   420
ccctagtcat ggtggcaccg tctggggccc gactaggtcc ctcacccac ctacaggccc     480
ttctccagga cagaccacac ttcatgcatc agctctccac tgtggatgcc catgcccaga   540
cccctgtgct ccaagtgcgt ccactggaca acccagccat gatcagcctc ccaccaccttt   600
ctgctgccac tggggtcttc tccctcaagg cccggcctgg cctgccacct gggatcaatg   660
tggccagtct ggaatgggtg tccagggagc cagctctact ctgcaccttc ccacgctcgg   720
gtacacccag aaaagacagc aaccttttgg ctgcacccca aggatcctac ccactgctgg   780
caaatggagt ctgcaagtgg cctggttgtg agaaggtctt cgaggagcca aagagtttc     840
tcaagcactg ccaagcagat catctcctgg atgagaaagg caaggcccag tgcctcctcc   900
agagagaagt ggtgcagtct ctggagcagc agctggagct ggaaaaggag aagctgggag   960
ctatgcaggc ccacctggct gggaagatgg cgctggccaa ggctccatct gtggcctcaa  1020
tggacaagag ctcttgctgc atcgtagcca ccagtactca gggcagtgtg ctcccggcct  1080
ggtctgctcc tcgggaggct ccagacggcg gcctgtttgc agtgcggagg cacctctggg  1140
gaagccatgg caatagttcc ttcccagagt tcttccacaa catggactac ttcaagtacc  1200
acaatatgcg acccccttttc acctatgcca cccttatccg atgggccatc ctggaagccc  1260
cggagaggca gaggacactc aatgaaatct accattggtt tactcgcatg ttcgcctact  1320
tcagaaacca ccccgccacc tggaagaatg ccatccgcca caacctgagc ctgcacaagt  1380
gctttgtgcg agtggagagc gagaagggag cagtgtggac cgtagatgaa tttgagtttc  1440
gcaagaagag gagccaacgc cccaacaagt gctccaatcc ctgcccttga cctcaaaaacc  1500
aagaaaaggt gggcggggga gggggccaaa accatgagac tgaggctgtg ggggcaagga   1560
ggcaagtcct acgtgtacct atggaaaccg ggcgatgatg tgcctgctat cagggcctct   1620
gctccctatc tagctgccct cctagatcat atcatctgcc ttacagctga gaggggtgcc   1680
aatcccagcc tagccctag ttccaaccta gccccaagat gaactttcca gtcaaagagc   1740
cctcacaacc agctatacat atctgccttg gccactgcca agcagaaaga tgacagacac  1800
catcctaata tttactcaac ccaaacccta aaacatgaag agcctgcctt ggtacattcg   1860
tgaactttca agttagtca tgcagtcaca catgactgca gtcctactga ctcacacccc   1920
aaagcactca cccacaacat ctggaaccac gggcactatc acacataggt gtatatacag   1980
accccttacac agcaacagca ctggaaccctt cacaattaca tcccccccaaa ccacacaggc  2040

```
ataactgatc atacgcagcc tcaagcaatg cccaaaatac aagtcagaca cagcttgtca    2100
gaacacgctc gtgtgcacgt acacacatgc agcccctcca ctctatctcc tgagttccat    2160
gaatacacac cgactctcca agatgtaccc cacgtctcac ttgccactga ccccagttcc    2220
ctacccacaa gccccaatcc atgcctaagc gtggcccaca gaagaacttc tcttttattt    2280
gggatccaag gccctggcc cccagtgccc atccaataaa ctgtggtcag ctggacaatc    2340
accctgatca gatatgggaa catataagca gacagctggg tttaagatcc cagcaggaga    2400
aagcggatac caaatgaaag agagtgctag aacaggtgcc tcagcactgt ctccagcacc    2460
ccaaattcct gcctgtggtt aggagacatc catcagggct ctaggcctct cggacccggc    2520
ccaagaggcc agcattctcc tggcgaaggg ctcggtagtc ctcacagatc ttctccaggt    2580
tgctcaaagt cttcttgccc atctctgtct caatctaaga aaacaggatg cacacttctt    2640
cagcccctgc aggctgcccc tctactgaac tcctccctgc tcctcctatt cccgtaacag    2700
cagcctgttc cttcccatca ctgggcttct gggtatgtcc ttccctccac tccacctaaa    2760
gcagcaactt ctgccatggg ctctgggagg cattaggagc cgcaagctaa aagccagggc    2820
tcagagtagg ctactggcta gcttcaggtc ccaggcacag tgggcacgaa ggcaaagcct    2880
ctagctgtta gttgtctggt ttcaaagact ctcagcgcaa acaaggaac tatcccctgg    2940 cctgtctcca ttcccttac cagtcccagg tctcacctgc tcctcaagat ctcgaacttc    3000
cctcatgata gtgcctgtgt cctcaatggt ctggatgagc tgactgcaat tctggagaca    3060
gcaagaatac aaggcttgca cctatgctgg ccctctccag ccaacccacc aggcacatgg    3120
ctcccctcac ctcatgcagg gcagctaggt acttgtaggc tttccgaaca gcatcatcct    3180
tcttagcatc ctgataagac aaaggggatc tccgagatat cagcaagcca ttccccctt    3240 tccactactc tatgccccta aagaccacc ctttactagt actttgcctt catcctccac    3300
agagcaaagc taggcccaa gcaacagtgc acctaaagga ctcacagagg ggcaggcaac    3360
aactcagtcc cgcctccacc ctcccggagg ccagcctgct ccataccttg aacacaagct    3420
catcagtcac tgcaaatgtc cggtcgagct tcccagagag agagttgatt tccttctgca    3480
gttcctttgt gtccgacaag atctggtaga aaccagggta actatcagtg cacatcttgg    3540
gcaaggtagc tgatcagtga taacactcac gtgcctatac ttacatccag tcagggccca    3600
tgtcgctgtg ttggggtgac tattatgtgt tggagtgtgc ctgaacagct ctgcctagta    3660
gtgagcataa agtccctgtg t                                              3681
```

<210> SEQ ID NO 7
<211> LENGTH: 11664
<212> TYPE: DNA
<213> ORGANISM: Artificial Sequence
<220> FEATURE:
<223> OTHER INFORMATION: A synthetic nucleic acid sequence

<400> SEQUENCE: 7

```
ggtaccatgt ctatcctgac cctaagatta gttcctcggg tttgaggatt gcagcaacac     60
tgaccgttca ggccctggtc aaggtggggc tgctgcttct tccttggctt ctttccaagg    120
agccaccaag aggcagaaag aaatgaagag acacaaagca aggcagaata gcacttcgga    180
tgacactgtc cgcattgccc gacagatatg gcactagact gcagccaaag gactctctga    240
aactattaac aaggttgtga gaacttgtga ccagtctgtg aggtgctgtg tctgggtgtc    300
atgtcactgg ggacatcatc agtgtcacca gtggcacagt ggaatgcctg gtgagctgag    360
```

```
acacacaaat gaggcaggcg tggtgggcac acacctgtaa tcccaacgga acgtaaacct    420
ggtatggcag tgctcacctg tatgtggtgg cactcaggaa gtggaggcag gagcattagg    480
agtctaaggt catcctcagc tacattgaca aatctgagac cagcctgggc gacatgagtc    540
cttgtgttaa aaaaaaaaaa aaaaaaaaaa aaaaaaaaag agagagagag agagagagag    600
agaatcagac agtggtggtg catgctttta atccagcact gggaggcag aggcaaacag     660 attactgtga gatcaaggcc agcctggtct tcagagcaag ttccaggaca agcagggcta    720
catagaaaaa acccgtctct ataaacaaac aaaacaaaac aaaacaaaaa aaagcagatc    780
tcgtgactct ctgaagaagg ccatttcccg ccagtccttg gggttagccg taagtagcag    840
gctgtagtgt ctcgaggcca caaaaactag agaaccctg ggaccacttc cagggtgtcg      900
ttttacatca catgtccaac tatttacctt catcttgggg ctagctccca ccccatacag    960
cctgtgagtg ctggaggact ttctagggag cctccgtagg aaaggcactg gcaggtctca   1020
gaaaaggatc ggggtcctga tgggggggcg ggggtcagta gtgcctaatg cactcagaca   1080
agcaccggcg ctgcagccag ccctgaactg cttttctct aagcccagcc aggtgtggac     1140
atagcctcag aggaccacgt gtcagctgaa tcccatctca tgcccaggag gggtgactgg   1200
gagagatggg catctgcttc tgggtaaagc tacctaagag ccacagggga cacagaaatc   1260
tcagcctcac agggcacttt cctgtttgtc taatgctcct ctccctagca ccagccagga   1320
gtctatagaa tcagaggatt ttaaagtaag gggggagtgg gaggtcggtt ggccccagga   1380
gcaccctaag tgtgcccttc cggcacttac cctgcgtcaa gagccaggaa ggaagctctc   1440
aagggcgttg cataagagta gaggattgag aagcctgggg tggggctaga gaggctcatt   1500
ctgaccccac tcagcatccc ttgcacagtc cagagcgtgg ggatcaaacg agacccctt     1560 gtttgacggt gaacaaagtc aggctgaggg ggttcgggaa gggggtaaag gactaggaac   1620
cgacatcggc cagcacacgg gaggtggaca ggggtgtccc tgctgagaag acctggaggg   1680
ctctcaagac acaggcaaac actgaggtca gcctgttccc atggagtcca gcccccaggt   1740
cctctcccct actataagag cccatgactc aagtagggta ctaagcagta ggcagccatg   1800
gccaagtcgc acctactgca gtggctactg ctgcttccta ccctctgctg cccaggtgca   1860
ggtgagtccc cggcctccct cacagaggcc tctccagcac ttactgagtc agctccgtgc   1920
ccagaaagac cccagtctgc acataatcca gaatttaaac gccagttagc tgaggcacag   1980
agaagtccta gggcctcatc caaggtcaca gttagtggat ggatgttgaa gcaggaggac   2040
tcagagctgc ctggcagaag caatggccac tcctttgcaa tgaaactggg ttggaggtgg   2100
ggtggaggca gggtgccgag tgtatgctgg atcctgatga gagttgctct gaccccaact   2160
ccagctatca cgtcggcctc atccctggag tgtgcacaag gccctcaatt ctggtgccaa   2220
agcctggagc atgcagtgca gtgcagagcc ctggggcact gcctgcagga agtctggggg   2280
catgcaggag ctgtgagtag caccaagcgg gcactgaaaa tccagggagg aggaactggg   2340
gtggattctg agcggacctt aggaaattgg agttcccaca aggctgggt ggcagggaat     2400 gatggaatgg tatagtgtga caggaaatgg tgggcagagt acaatagaag gaaacatggt   2460
ggaatgagat gaatggggtg ggcatggtgg gtaagacagg gtggatgtgt gggtaagaca   2520
gggtggatgt ggtgggtaag acagggtaga tgtggtgggt aagaggggt gagcatgtgg      2580 gtaagatggg gtggctgggg tgagatggac aagatggaat agaacagggt ggatcaagtg   2640
ggtggcacag aatgggatgg aatttgcaca atgggatgag atgggatgat gggtgggtag   2700
ccttaaggta cctgtcagcc tgtgtctgag aaagcctcaa tccctggagt taggagcatg   2760
```

```
cccccaactc attagcctca cttgagaccc tttcttccag aatgacctgt gccaagagtg     2820
tgaggatatt gtccacctcc tcacaaagat gaccaaggaa gatgctttcc aggtaatggg     2880
aaacggtaca gtgtgatctg gtagaggcct ggcgtcaggg gactctggtg ggggcagacc     2940
tcagaaagac caggctaatc ctcccttctc tgctctccca ggaagcaatc cggaagttcc     3000
tggaacaaga atgtgatatc cttcccttga agctgcttgt gccccggtgt cgccaagtgc     3060
ttgatgtcta cctgcccctg gttattgact acttccagag ccagattgtg aggaccctga     3120
cctacctgcc gcacagtgca tgtgcctaag tggccactta cctatataag tggcacccca     3180
acacatgcac acacacacat acacacccac agacgcaata agacacacac acacacacgt     3240
acacacacac acacacacac acacacacac acacttcc cactacagcc acaggaagct     3300
cagtctcttc atccagatac ccaaatcaga gcctgcctgc tcagcatact acagacattg     3360
agacccgccc tccatcccct cacccacaca tgcccacatt cttattgtca cacaatatgc     3420
tcacacacac tcactctttc cagacacatg ctcccaggcc ctacacagcc catctctct     3480 gtctttgtcc ctttcatagt gtcctaagat gcagtacttc acccagcctg ctccccataa     3540
ccccaggctc aaagactgtg gcccttgtcc ctgaatatga acctgggcag agagggttc     3600 cctccttacc ctaaaacccc tcacctgttc catgccctag aaccccaaag ccatctgcaa     3660
tcatgtaggc ctgtgcccac gtgggcaggc taagccagaa cagaatccag ggatgccgga     3720
tgccgttcca aaccctctgc tggacaagct ggtcctccct gtgctgccag gagccctctt     3780
ggcaaggcct gggcctcaca ctcaggtaag ccagtccatt cccagcagct gctgggaatc     3840
cagaaggcta gcatggccgc tgagacgcgt gggcacccag agaggctgag ctcaaactag     3900
gaggcagaga tggcaaggtc aggcaaggtc acacaaccga ggtagctccc agcctaacca     3960
cacttcaccg cttccttcct caggacttct ctgagcaaca gctccccatt ccctgccct     4020 tctgctggct ttgcagaact ctgatcaagc gggttcaagc cgtgatcccc aaggtaagga     4080
ccacacagag ctcagagggg cccccaatag ctggcaccct cctccacctc aacactccaa     4140
gaaggctgtg aggagttaga tgaggagaca cccacacatt gctcctaccc aaggaacctt     4200
gaggctcagg tatgggaggt taggtcagag ccaccttctc ttccaacaga tcaccatcgg     4260
aaggctgaga agcactggtt gtcactgtag gaaaaaagta cattaatttc tcaaaaaaaa     4320
aaaaaaacag ttcatcaata gtaagcatct cttctgtcct ccaaatccat ggtagcctct     4380
gccagtgcct tgtcagatga ggattgttct ccccacaaat ggtcatggcc tatcaacact     4440
aacactaagc ccacatcagt cataaagaca acagggcaca cagtcaagcc tttctgaagc     4500
ctgtgtgatg gaaggaacgt gcagactata gagcaggatg agctgagggg tcgcacagat     4560
aaaaatggta acagacaggt cagccaggga gaggctctga agagggtaac aactaagcca     4620
agatctagga gaaacaagg tccccagggg ccaaggacat ccatccatca ataaaaaatg     4680
agctcaatca gatgttggag ggagggactc tgtaaggagg gaccaggagc aggggcagc     4740 gtttggggtg taaatgatag ataaatgcct ttaaaatgag ctcagagggc taggaagatg     4800
gctcggtgag tacagtcctt gctgaacctg agttcagata cttgcaccct cataaaagtt     4860
ggggggtggg ctggagacat ggctcagtag ttaagagcac tgactgctct tctagaggtc     4920
ctgagttcaa ttcccagcaa ccacttggtg gctcacaacc acctataatg ggatctgatg     4980
ccctcttctg gtgtgtctga acttacatac ataaataaa aataaagtt gggggttgct     5040 cacagtcagc taatggatgg atcataggc tcccaatgga ggagctagag aaagtagcca     5100
```

```
aggagctaaa gggatctgca accctatagg tggaacaaca ttatgagcta accagtaccc    5160
cggagctctt gactctagct gcatatatat caaaagatgg cctagtcggc catcactgga    5220
aagagaggcc cattggactt gcaaacttta tatgccccag tacagggaa taccagggcc    5280 aaaaagggg agtgggtggg caggggagtg ggggtgggtg gatatggggg acttttggta    5340
tagcattgga aatgtaaatg agttaaatac ctaataaaaa atggaaaaaa aaaagttgg    5400 gggttagcaa tgaacatttg taaccctaca cactaggtag tcagaaatag gcagatccct    5460
agagcatgct ggccagccag tctagccaaa tggatgagct tcagggttag tgtgagacct    5520
tgtctcaaaa aaaaaaaaaa aaaaaaaaaa aatggacggc ctgaagattc ggatcgacag    5580
ttaggaacat ttgctgcttt tcagaagagt gagttgggta cccagcacca ctgtcaggca    5640
gctcacaacc ccctgtaact gctgctctag ggaatccaat gccctcttct ggcagccaag    5700
ggcaccagca catatgtggc attcatatac tcagatacac agacatatgt aaaaataaaa    5760
ataaatcttt agaaaataat taggtaggga gtgaagtgac taaggaagac actcaatctt    5820
ggctctggcc tccacacaca tgtgcacatg tacttaaaca tctacgtgca aaacaaacaa    5880
acaaacaccc agccgtatca atgtgaacat cactgaggac cgaaggcatg agcaagactg    5940
ttaagagaca atgtatagac agatggagat ggcatcagaa ttgctgagag gggacaggca    6000
gccaacgggg gaccgtgctg cattgccagg gaagccaaga gagaagggtg tttgactgat    6060
tgaaaggcag ctgaaccatc aggcagggtg agagttaggc aggggatgtg gaagtgttcc    6120 aaaaaggga gcaggcatgg tgaggcttcc taaggtcaga agccattcta gcgtgttctc    6180
caggcagcag ggaccagaga gaggataagg ccagggaaag aggcatgggt ggaggtaatc    6240
caggagtgaa gaccatttca ccaatgagca gcttggtcat tgactacagt gactattgat    6300
ttacatcacc atgacaggag agccatgtgt gggtcaatga taacaggtgg gtctcttaag    6360
tgaagtgccc catttgggag ccatcacact ccaggggtgt ccatattctg agtcctcccc    6420
ctgcctcaac ctcctggcac tggggctagc tggtcacatg ggctgaataa ggagtaaagg    6480
aaaaagccac accctggtga cctctgtcac ccttcagcta gagcctgctt ggaattggag    6540
ttgaggtagg agatgtgctg gctttcccag ggggttccaaa agccaaagac atgtcagctc    6600
tgggggccag cagaaggaac tgcctgtctt cctgatgcat aagcatggga aggtaggtgg    6660
ccctcggtca gggaatgggt ttgaattggg tcaggctgtt agatgccatg gccttgcagc    6720
cccctttcaa atgactcaag cctttagagc tagatctata tttggtgtca actgcagatt    6780
ctctcagtga ctccgggtgc acctgagacc cctgctgtct tggatgctca gtgacctgtg    6840
gacagaactg ctctttccta gaaggggagaa aggggatgca tctgggtgc ccactcagtt    6900 gggcacagtg acatcgtgcc agaagaaggt tctatggttg tcctttctcc accttcaccc    6960
cagggtgtgc tggctgtggc tgtgtcccag gtgtgccacg tggtaccct ggtggtgggt    7020 ggcatctgcc agtgcctggc tgagcgctac acagttctcc tgctagacgc actgctgggc    7080
cgtgtggtgc cccagctagt ctgtggcctt gtcctccgat gttccactga ggatgccatg    7140
ggccctggta agacttgccc gtcccctccc cctccccaac tcacatccct ccagtgcaca    7200
tgggagggaa catggacaag gtggggttca ggaaccaaca cttttttttaa actatttatt    7260 tctatggata tggctgcttt tatttatata gctgaggctg gctttgaact cctaatttcc    7320
cttcctcagc cattcaaatg ttaggaaagg ctagcaatga ctgtactcag cttctagctc    7380
tctccaagtg gacttctccc agttgagtta aagagtgatg ggggagggggt ggggaacagg    7440 gcaggaccct gggagaaggc taagttcttt ttttgctcca gcttggacat ctatataccc    7500
```

```
catgtatgcc tggctcccac agaggccata aaggatgtca aatccctag aattggaata    7560 actgacagtt atgagccatc atgtggggct ctgggaatcg aacctcagcc ctctggaaga    7620
gcagccagtg ctcttaacca cggaaccatc tctccagccc cagaaccaac acttgtacaa    7680
gacagtcctg ggggaaagat taaaacagag tcttactaca tagcacaggt tggcctcgag    7740
cttggtgcaa tcctcctgcc tcagcctctc aaatactggc atgacaaggt atgtgcctcc    7800
atacccagct tgctggacaa ttctaactgc tttctcttta gccctccctg ctgtggagcc    7860
tctgatagaa gaatggccac tacaggacac tgagtgccat ttctgcaagt ctgtgatcaa    7920
ccaggcctgg aacaccagtg aacaggctat gccacaggca atgcaccagg cctgccttcg    7980
cttctggcta gacaggcaaa aggtagggggg cccacgggtt ggatgtatgt catatgtgtg    8040
atggtgccga gctagaagag actttgtagc tagacacacg cacgatgctg gttcccagcc    8100
tggtggacag gcatgtgggt cagacaatga tgggattgta acaaatttaa ctggctagga    8160
gacatcatgg acccaaggct ttggactatg gaacatcagc aggccttctt tatggactaa    8220
gcacaagaaa agtcctgtta gtcccaacag gaaagggtca tactgcccctt tcttggtttc    8280 actcgatggt gtgtttgcca cactgttctc ccagtgtgcc atgtcacccc catgatgggt    8340
ggtagcattt gacagtacct agcaggcacc agaaaatgag aaaagccagg gtcagctgga    8400
gcagaaaaag aacttagcct tttcccaggg tcctgttctg ccccacccctg ctcactctgt    8460 agaagtcctg caggagagag ctggaagctg gtaccatagt gctagcctgt aattctaaca    8520
tttggaaagg ctgaagaagg agaaatggga gttcaaagcc agcctcagct atataaataa    8580
tgagttcagg gtcagcctgg gctacatgag accctgtctg gtgaaaggag acagagatag    8640
gaaagaacat gaggcttggg taaggctcac tggcatggcc acaaccaagt ttgatccctg    8700
ggatccgtat ggtaaacaaa gagaatcaac tcctgtaaac tttccttatg aacacacaca    8760
cacacgaaaa cataattttg aagccaggct gtggtggtgc acacctttag tcctagccct    8820
tgggaggcag aagcagatgg atctaagttt gagcccagcc tggtctacag tgtgagctcc    8880
aggacagcca gggttacaca gagaaaccct gtctcacaaa accaaaaaga aatcaacaac    8940
cacaaagaac tgaacagata gttccttaag cctgtgatga atccctcac tacagtggga    9000 ctttctttag agagggtcct atgtaactta aaccgcctcc acctcctttg tactgagact    9060
acaggcaggt accactactg agtttcatgt agttctgaag ttgaaactaa aggttttcatg    9120 catgctaggc aaccatgaga cgatgctaag ctgcaagcct gctccagctc caaggccctg    9180
gcttcctcca aagcctggtt tcagccaaac ttagatagag tcccttttttt taagactcat    9240 tttatttgtg tttttagtgc atgtatgtat ggacatcatg tgtgtgtggt gccggggggga    9300 gggggtcaga gaggccatc agattccctg gaactggagt tgagtggtta taagccgtcc    9360
ttcctgtcct ccaaagagca gcaagtgcct aaccccgag ccatcagcca ttcagcccctt    9420 cggttgagtc tttaatggtc agccaggcac tgatggaaaa acacaaaccc acagtccgga    9480
gtggcagagt gaggtagaac gccagatctg caggttaagt tctctcctag aggggggtct    9540
acatattgtg tctttcctca gtgtgaacag tttgtggaac agcacatgcc ccagctgctg    9600
gccctggtgc ctaggagcca ggatgccccac atcacctgcc aggtatgccc actcttcagc    9660
tggtcccagg agtcccctct gctcccacag tcccacccctc cttggtctat gatcctcaag    9720
agccccattt cttggatcca ggaagcctag ggctcagaag cccagaacta agtgtaccca    9780
tagaacaggc tttggacttg gagcagaaaa gaacacatac tgattaggtg ggaggggcaa    9840
```

```
gttcatgatg  atgggcagc  tgggggctgg  ggtatgatgc  tccttattgc  atgtggtgtg    9900
tttagtgacc  agtttgttct  atggtggggc  tatagtatga  ggtgggggtc  ccactaagtc    9960
ccaaggccat  tgacttaggg  aatggcacaa  ggggttctga  aggtgaaggt  gaagtgagag   10020
ttgtctccat  agccttgaga  attagacgta  gaaagctgag  gcccacgtgc  tgtctccaac   10080
aggcccttgg  cgtatgtgag  gccccggcta  gccctctgca  gtgcttccaa  accccacacc   10140
tctgagaacg  cggtctccag  gtgagtccag  cctcctgggg  agagaggg    atgggtcttt   10200
gcttgctaag  gtttgggaac  aagatggtca  tcctgcccac  ttctgtggac  tgtgtcatcc   10260
tacctctgcc  aggcacagtt  ccaggctcct  cggggtctcc  agtggttcca  tcaggaaaag   10320
gcagtctttt  ggacctatcg  tcactccttg  ctctcccacc  ccatccagcc  ctccacagct   10380
tctatctaag  gcttcatcac  atctgagctg  cctgacctta  aagatactcc  atgttcgagc   10440
aatggccaac  atttcttact  tcactgtctc  ggctgtctct  ccctcagatg  ccagcagcac   10500
catggtcacc  tgacctcacc  ctgcccaggc  tccctgtttt  ctaagccaga  aatagctctg   10560
acaccagagt  caggaaatga  catggggagt  gtggggcgag  aaaggcaaca  gtctctcaag   10620
tgaccctgac  agtaatctgg  tccaggtcac  aatgtactta  aagccagcgc  tcgctgggta   10680
gtcatttatc  catttgttcc  catttgtgaa  aatctgctgg  tgtgcacagc  tggcccacca   10740
cttctaatgc  gaggaaggac  cccagcactg  tcacagccac  tgtgggcaga  ggggcacttc   10800
aagtcagtaa  gtcccttggg  ggccaattta  atgtctcccc  tcccatcccc  catcaagtcc   10860
atctgggtgc  gcgaagggag  gcaatccagg  agtcaccttt  ttctagctct  cagggctcta   10920
ggccttgcct  gctgaagaag  gaattgtgag  agactccctg  agttctggtc  ccaactctgc   10980
tatcaacagt  cagtggatcc  cccgggaaaa  tcgcacagcc  cccacccttt  gcgatatcac   11040
taaactagct  gcaagtagcc  caatgaaggg  aacttcggca  cttatgaact  gtcaccatca   11100
cagtgacagt  gaccctactc  ccaccagtag  ctactctcct  tgaaaaagac  cttacctccc   11160
accctaatgc  tacttccttt  cccacagcag  cctgctccag  aggacaagcc  tcagcctgca   11220
ccctcagccc  tgtgtcagtc  tgtatgtccc  agctctaact  acagaccacc  accaccacca   11280
ccaccaccac  caccaccacc  accaccacca  ccaccaccac  caccaccacc  accacagtgg   11340
tttctggctc  ccccggtga   tgggggcgg   caggcccacg  tcctctggaa  gccttcagaa   11400
ggggcttcgg  gccttcgcct  ccaccagagc  caagccagct  cccatagctc  ccacagccca   11460
cagggactga  gaagaactgt  tgtggctcca  agaagacatc  gggtagaagc  tgggtatagc   11520
cacaccaacc  ccttgctaac  atttctatga  aatccaaact  tgagaagaat  aaagaatggg   11580
aacatggagc  attattctaa  gggctgtggg  cgaggcgcag  tgacagggca  ctttcctagc   11640
aagcaggaaa  cctgggttgg  atcc                                             11664
```

<210> SEQ ID NO 8
<211> LENGTH: 1083
<212> TYPE: DNA
<213> ORGANISM: Artificial Sequence
<220> FEATURE:
<223> OTHER INFORMATION: A synthetic nucleic acid sequence

<400> SEQUENCE: 8

```
atggcgggac  acctggcttc  ggatttcgcc  ttctcgcccc  ctccaggtgg  tggaggtgat     60
gggccagggg  ggccggagcc  gggctgggtt  gatcctcgga  cctggctaag  cttccaaggc    120
cctcctggag  ggcagggaat  cgggccgggg  gttgggccag  gctctgaggt  gtggggatt    180
ccccccatgcc  cccgccgta   tgagttctgt  ggggggatgg  cgtactgtgg  gccccaggtt   240
```

-continued

```
ggagtggggc tagtgcccca aggcggcttg gagacctctc agcctgaggg cgaagcagga    300 gtcgggtgg agagcaactc cgatggggcc tccccggagc cctgcaccgt caccctggt    360 gccgtgaagc tggagaagga gaagctggag caaaacccgg aggagtccca ggacatcaaa   420
gctctgcaga aagaactcga gcaatttgcc aagctcctga agcagaagag gatcaccctg   480
ggatatacac aggccgatgt ggggctcacc ctggggttc tatttgggaa ggtattcagc    540
caaacgacca tctgccgctt tgaggctctg cagcttagct tcaagaacat gtgtaagctg   600
cggcccttgc tgcagaagtg ggtggaggaa gctgacaaca atgaaaatct tcaggagata   660
tgcaaagcag aaaccctcgt gcaggcccga aagagaaagc gaaccagtat cgagaaccga   720
gtgagaggca acctggagaa tttgttcctg cagtgcccga aacccacact gcagcagatc   780
agccacatcg cccagcagct tgggctcgag aaggatgtgg tccgagtgtg gttctgtaac   840
cggcgccaga agggcaagcg atcaagcagc gactatgcac aacgagagga ttttgaggct   900
gctgggtctc ctttctcagg gggaccagtg tcctttcctc tggccccagg ccccattt    960 ggtaccccag gctatgggag ccctcacttc actgcactgt actcctcggt cccttttccct  1020 gaggggaag cctttccccc tgtctccgtc accactctgg gctctcccat gcattcaaac   1080
tga                                                                1083
```

<210> SEQ ID NO 9
<211> LENGTH: 954
<212> TYPE: DNA
<213> ORGANISM: Artificial Sequence
<220> FEATURE:
<223> OTHER INFORMATION: A synthetic nucleic acid sequence

<400> SEQUENCE: 9

```
atgtacaaca tgatggagac ggagctgaag ccgccgggcc cgcagcaaac ttcggggggc     60
ggcggcggca actccaccgc ggcggcggcc ggcggcaacc agaaaaacag cccgaccgc    120 gtcaagcggc ccatgaatgc cttcatggtg tggtcccgcg ggcagcggcg caagatggcc   180
caggagaacc ccaagatgca caactcggag atcagcaagc gcctgggcgc cgagtggaaa   240
cttttgtcgg agacggagaa gcggccgttc atcgacgagc taagcggct gcgagcgctg   300 cacatgaagg agcacccgga ttataaatac cggccccggc ggaaaaccaa gacgctcatg   360
aagaaggata agtacacgct gcccggcggg ctgctggccc ccgcggcaa tagcatggcg   420 agcgggtcg ggtgggcgc cggcctgggc gcgggcgtga accagcgcat ggacagttac   480
gcgcacatga acggctggag caacggcagc tacagcatga tgcaggacca gctgggctac   540
ccgcagcacc cgggcctcaa tgcgcacggc gcagcgcaga tgcagcccat gcaccgctac   600
gacgtgagcg ccctgcagta caactccatg accagctcgc agacctacat gaacggctcg   660
cccacctaca gcatgtccta ctcgcagcag ggcaccccctg gcatggctct ggctccatg   720 ggttcggtgg tcaagtccga ggccagctcc agcccccctg tggttacctc ttcctcccac   780
tccagggcgc cctgccaggc cggggacctc cgggacatga tcagcatgta tctccccggc   840
gccgaggtgc cggaacccgc cgccccccagc agacttcaca tgtcccagca ctaccagagc   900
ggcccggtgc ccggcacggc cattaacggc acactgcccc tctcacacat gtga          954
```

<210> SEQ ID NO 10
<211> LENGTH: 1440
<212> TYPE: DNA
<213> ORGANISM: Artificial Sequence
<220> FEATURE:

<223> OTHER INFORMATION: A synthetic nucleic acid sequence

<400> SEQUENCE: 10

```
atgaggcagc cacctggcga gtctgacatg gctgtcagcg acgcgctgct cccatctttc    60
tccacgttcg cgtctggccc ggcgggaagg gagaagacac tgcgtcaagc aggtgccccg   120
aataaccgct ggcgggagga gctctcccac atgaagcgac ttcccccagt gcttcccggc   180
cgccctatg acctggcggc ggcgaccgtg ccacagacc tggagagcgg cggagccggt    240
gcggcttgcg gcggtagcaa cctggcgccc ctacctcgga gagagaccga ggagttcaac   300
gatctcctgg acctggactt tattctctcc aattcgctga cccatcctcc ggagtcagtg   360
gccgccaccg tgtcctcgtc agcgtcagcc tcctcttcgt cgtcgccgtc gagcagcggc   420
cctgccagcg cgccctccac ctgcagcttc acctatccga tccgggccgg gaacgacccg   480
ggcgtggcgc cgggcggcac gggcggaggc ctcctctatg cagggagtc cgctccccct    540
ccgacggctc ccttcaacct ggcggacatc aacgacgtga gccctcgggc ggcttcgtg    600
gccgagctcc tgcggccaga attggacccg gtgtacattc cgccgcagca gccgcagccg   660
ccaggtggcg ggctgatggg caagttcgtg ctgaaggcgt cgctgagcgc ccctggcagc   720
gagtacggca cccgtcggt catcagcgtc agcaaaggca gccctgacgg cagccacccg    780
gtggtggtgg cgccctacaa cggcgggccg ccgcgcacgt gccccaagat caagcaggag   840
gcggtctctt cgtgcaccca cttgggcgct ggaccccctc tcagcaatgg ccaccggccg   900
gctgcacacg acttcccct ggggcggcag ctccccagca ggactacccc gaccctgggt     960
cttgaggaag tgctgagcag cagggactgt caccctgccc tgccgcttcc tcccggcttc   1020
catccccacc cggggcccaa ttacccatcc ttcctgcccg atcagatgca gccgcaagtc   1080
ccgccgctcc attaccaaga gctcatgcca cccggttcct gcatgccaga ggagcccaag   1140
ccaaagaggg gaagacgatc gtggccccgg aaaaggaccg ccacccacac ttgtgattac   1200
gcgggctgcg gcaaaaccta cacaaagagt tccatctca aggcacacct gcgaacccac   1260
acaggtgaga aaccttacca ctgtgactgg gacggctgtg gatggaaatt cgcccgctca   1320
gatgaactga ccaggcacta ccgtaaacac acggggcacc gcccgttcca gtgccaaaaa   1380
tgcgaccgag cattttccag gtcggaccac ctcgccttac acatgaagag gcattttaa   1440
```

<210> SEQ ID NO 11
<211> LENGTH: 1365
<212> TYPE: DNA
<213> ORGANISM: Artificial Sequence
<220> FEATURE:
<223> OTHER INFORMATION: A synthetic nucleic acid sequence

<400> SEQUENCE: 11

```
ctggattttt ttcgggtagt ggaaaaccag cagcctcccg cgacgatgcc cctcaacgtt    60
agcttcacca acaggaacta tgacctcgac tacgactcgg tgcagccgta tttctactgc   120
gacgaggagg agaacttcta ccagcagcag cagcagagcg agctgcagcc ccggcgcgcc   180
agcgaggata tctggaagaa attcgagctg ctgcccaccc cgcccctgtc cctagccgc    240
cgctccgggc tctgctcgcc ctcctacgtt gcggtcacac ccttctcct tcggggagac   300
aacgacggcg gtggcgggag cttctccacg gccgaccagc tggagatggt gaccgagctg   360
ctgggaggag acatggtgaa ccagagtttc atctgcgacc cggacgacga gaccttcatc   420
aaaaacatca tcatccagga ctgtatgtgg agcggcttct cggccgccgc caagctcgtc   480
tcagagaagc tggcctccta ccaggctgcg cgcaaagaca gcggcagccc gaaccccgcc   540
```

```
cgcggccaca gcgtctgctc cacctccagc ttgtacctgc aggatctgag cgccgccgcc      600
tcagagtgca tcgacccctc ggtggtcttc ccctaccctc tcaacgacag cagctcgccc      660
aagtcctgcg cctcgcaaga ctccagcgcc ttctctccgt cctcggattc tctgctctcc      720
tcgacggagt cctccccgca gggcagcccc gagcccctgg tgctccatga ggagacaccg      780
cccaccacca gcagcgactc tgaggaggaa caagaagatg aggaagaaat cgatgttgtt      840
tctgtggaaa agaggcaggc tcctggcaaa aggtcagagt ctggatcacc ttctgctgga      900
ggccacagca aacctcctca gcccactg gtcctcaaga ggtgccacgt ctccacacat      960
cagcacaact acgcagcgcc tccctccact cggaaggact atcctgctgc aagagggtc      1020 aagttggaca gtgtcagagt cctgagacag atcagcaaca accgaaaatg caccagcccc      1080
aggtcctcgg acaccgagga gaatgtcaag aggcgaacac acaacgtctt ggagcgccag      1140
aggaggaacg agctaaaacg gagctttttt gccctgcgtg accagatccc ggagttggaa      1200
aacaatgaaa aggcccccaa ggtagttatc cttaaaaaag ccacagcata catcctgtcc      1260
gtccaagcag aggagcaaaa gctcatttct gaagaggact tgttgcggaa acgacgagaa      1320
cagttgaaac acaaacttga acagctacgg aactcttgtg cgtaa                      1365
```

<210> SEQ ID NO 12
<211> LENGTH: 4107
<212> TYPE: DNA
<213> ORGANISM: Artificial Sequence
<220> FEATURE:
<223> OTHER INFORMATION: A synthetic nucleic acid sequence

<400> SEQUENCE: 12

```
atggataaga atactcaat aggcttagat atcggcacaa atagcgtcgg atgggcggtg      60
atcactgatg aatataaggt tccgtctaaa aagttcaagg ttctgggaaa tacagaccgc     120
cacagtatca aaaaaaatct tatagggggct cttttatttg acagtggaga gacagcggaa     180
gcgactcgtc tcaaacggac agctcgtaga aggtatacac gtcggaagaa tcgtatttgt     240
tatctacagg agatttttc aaatgagatg gcgaaagtag atgatagttt ctttcatcga     300
cttgaagagt cttttttggt ggaagaagac aagaagcatg aacgtcatcc tatttttgga     360
aatatagtag atgaagttgc ttatcatgag aaatatccaa ctatctatca tctgcgaaaa     420
aaattggtag attctactga taaagcggat ttgcgcttaa tctatttggc cttagcgcat     480
atgattaagt tcgtggtca ttttttgatt gagggagatt taaatcctga taatagtgat     540
gtggacaaac tatttatcca gttggtacaa acctacaatc aattatttga agaaaaccct     600
attaacgcaa gtggagtaga tgctaaagcg attctttctg cacgattgag taaatcaaga     660
cgattagaaa atctcattgc tcagctcccc ggtgagaaga aaatggctt atttgggaat     720 ctcattgctt tgtcattggg tttgaccct aattttaaat caatttttga tttggcagaa     780
gatgctaaat tacagctttc aaaagatact acgatgatg atttagataa tttattggcg     840
caaattggag atcaatatgc tgatttgttt ttggcagcta agaatttatc agatgctatt     900
ttactttcag atatcctaag agtaaatact gaaataacta aggctcccct atcagcttca     960
atgattaaac gctacgatga acatcatcaa gacttgactc ttttaaaagc tttagttcga     1020
caacaacttc cagaaagta taagaaatc ttttttgatc aatcaaaaaa cggatatgca     1080
ggttatattg atgggggagc tagccaagaa gaatttatat aatttatcaa accaatttta     1140
gaaaaaatgg atggtactga ggaattattg gtgaaactaa atcgtgaaga tttgctgcgc     1200
```

```
aagcaacgga cctttgacaa cggctctatt ccccatcaaa ttcacttggg tgagctgcat    1260
gctattttga gaagcaagaa agacttttat ccattttaaa aagacaatcg tgagaagatt    1320
gaaaaaatct tgacttttcg aattccttat tatgttggtc cattggcgcg tggcaatagt    1380
cgttttgcat ggatgactcg gaagtctgaa gaaacaatta ccccatggaa ttttgaagaa    1440
gttgtcgata aggtgcttc agctcaatca tttattgaac gcatgacaaa ctttgataaa    1500
aatcttccaa atgaaaaagt actaccaaaa catagtttgc tttatgagta ttttacggtt    1560
tataacgaat tgacaaaggt caaatatgtt actgaaggaa tgcgaaaacc agcatttctt    1620
tcaggtgaac agaagaaagc cattgttgat ttactcttca aaacaaatcg aaaagtaacc    1680
gttaagcaat taaaagaaga ttatttcaaa aaaatagaat gttttgatag tgttgaaatt    1740
tcaggagttg aagatagatt taatgcttca ttaggtacct accatgattt gctaaaaatt    1800
attaaagata aagatttttt ggataatgaa gaaatgaag atatcttaga ggatattgtt    1860
ttaacattga ccttatttga agatagggag atgattgagg aaagacttaa acatatgct    1920 caccctcttg atgataaggt gatgaaacag cttaaacgtc gccgttatac tggttgggga    1980
cgtttgtctc gaaaattgat taatggtatt agggataagc aatctggcaa acaatatta    2040 gatttttga atcagatgg ttttgccaat cgcaatttta tgcagctgat ccatgatgat    2100
agtttgacat ttaagaaga cattcaaaaa gcacaagtgt ctggacaagg cgatagttta    2160
catgaacata ttgcaaattt agctggtagc cctgctatta aaaaaggtat tttacagact    2220 gtaaagttg ttgatgaatt ggtcaaagta atggggcggc ataagccaga aaatatcgtt    2280
attgaaatgg cacgtgaaaa tcagacaact caaaagggcc agaaaaattc gcgagagcgt    2340
atgaaacgaa tcgaagaagg tatcaaagaa ttaggaagtc agattcttaa agagcatcct    2400
gttgaaaata ctcaattgca aaatgaaaag ctctatctct attatctcca aaatggaaga    2460
gacatgtatg tggaccaaga attagatatt aatcgtttaa gtgattatga tgtcgatcac    2520
attgttccac aaagtttcct taagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taaacttatt cgagaggtta aagtgattac cttaaaatct    2880
aaattagttt ctgacttccg aaaagatttc caattctata agtacgtga gattaacaat    2940 taccatcatg cccatgatgc gtatctaaat gccgtcgttg gaactgcttt gattaagaaa    3000
tatccaaaac ttgaatcgga gtttgtctat ggtgattata agtttatga tgttcgtaaa    3060 atgattgcta agtctgagca agaaatagg caaagcaaccg caaatatttt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aaagggaaat cgaagaagtt aaaatccgtt    3480
aaagagttac tagggatcac aattatgaa agaagttcct ttgaaaaaaa tccgattgac    3540
tttttagaag ctaaaggata taaggaagtt aaaaaagact taatcattaa actacctaaa    3600
```

```
tatagtcttt ttgagttaga aaacggtcgt aaacggatgc tggctagtgc cggagaatta    3660
caaaaaggaa atgagctggc tctgccaagc aaatatgtga atttttttata tttagctagt    3720 cattatgaaa agttgaaggg tagtccagaa gataacgaac aaaaacaatt gtttgtggag    3780
cagcataagc attatttaga tgagattatt gagcaaatca gtgaattttc taagcgtgtt    3840
attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta aacgatatac gtctacaaaa    4020
gaagttttag atgccactct tatccatcaa tccatcactg gtctttatga aacacgcatt    4080
gatttgagtc agctaggagg tgactga                                         4107
```

<210> SEQ ID NO 13
<211> LENGTH: 4104
<212> TYPE: DNA
<213> ORGANISM: Artificial Sequence
<220> FEATURE:
<223> OTHER INFORMATION: A synthetic nucleic acid sequence

<400> SEQUENCE: 13

```
atggataaga aatactcaat aggcttagat atcggcacaa atagcgtcgg atgggcggtg      60
atcactgatg aatataaggt tccgtctaaa aagttcaagg ttctgggaaa tacagaccgc     120
cacagtatca aaaaaaatct tatagggct cttttatttg acagtggaga gacagcggaa     180
gcgactcgtc tcaaacggac agctcgtaga aggtatacac gtcggaagaa tcgtatttgt     240
tatctacagg agattttttc aaatgagatg gcgaaagtag atgatagttt ctttcatcga     300
cttgaagagt ctttttttggt ggaagaagac aagaagctga acgtcatcct atttttggaa     360
atatagtaga tgaagttgct tatcatgaga atatccaac tatctacatc tgcgaaaaaa      420
attggtagat tctactgata aagcggattt gcgcttaatc tatttggcct tagcgcatat     480
gattaagttt cgtggtcatt ttttgattga gggagattta atcctgata atagtgatgt     540 ggacaaacta tttatccagt tggtacaaac ctacaatcaa ttatttgaag aaaaccctat     600
taacgcaagt ggagtagatg ctaaagcgat tctttctgca cgattgagta aatcaagacg     660
attagaaaat ctcattgctc agctccccgg tgagaagaaa aatggcttat tgggaatct     720 cattgctttg tcattgggtt tgacccctaa ttttaaatca aattttgatt ggcagaaga     780 tgctaaatta cagctttcaa aagatactta cgatgatgat ttagataatt tattggcgca     840
aattggagat caatatgctg atttgttttt ggcagctaag aatttatcag atgctatttt     900
actttcagat atcctaagag taaatactga ataactaag gctcccctat cagcttcaat     960
gattaaacgc tacgatgaac atcatcaaga cttgactctt ttaaaagctt tagttcgaca    1020
acaacttcca gaaaagtata agaaatcttt ttttgatcaa tcaaaaaacg gatatgcagg    1080
ttatattgat gggggagcta gccaagaaga atttataaa tttatcaaac caattttaga    1140
aaaaatggat ggtactgagg aattattggt gaaactaaat cgtgaagatt gctgcgcaa    1200 gcaacggacc tttgacaacg gctctattcc ccatcaaatt cacttgggtg agctgcatgc    1260
tattttgaga agacaagaag acttttatcc attttttaaa gacaatcgtg agaagattga    1320
aaaaatcttg acttttcgaa ttccttatta tgttggtcca ttggcgcgtg caatagtcg    1380 ttttgcatgg atgactcgga agtctgaaga aacaattacc ccatggaatt ttgaagaagt    1440
tgtcgataaa ggtgcttcag ctcaatcatt tattgaacgc atgacaaact tgataaaaa    1500
```

```
tcttccaaat gaaaaagtac taccaaaaca tagtttgctt tatgagtatt ttacggttta    1560
taacgaattg acaaaggtca aatatgttac tgaaggaatg cgaaaaccag catttctttc    1620
aggtgaacag aagaaagcca ttgttgattt actcttcaaa acaaatcgaa aagtaaccgt    1680
taagcaatta aaagaagatt atttcaaaaa aatagaatgt tttgatagtg ttgaaatttc    1740
aggagttgaa gatagattta atgcttcatt aggtacctac catgatttgc taaaaattat    1800
taaagataaa gattttttgg ataatgaaga aaatgaagat atcttagagg atattgtttt    1860
aacattgacc ttatttgaag ataggagat gattgaggaa agacttaaaa catatgctca    1920
cctctttgat gataaggtga tgaaacagct taaacgtcgc cgttatactg gttggggacg    1980
tttgtctcga aaattgatta atggtattag ggataagcaa tctggcaaaa caatattaga    2040
ttttttgaaa tcagatggtt ttgccaatcg caattttatg cagctgatcc atgatgatag    2100
tttgacattt aaagaagaca ttcaaaaagc acaagtgtct ggacaaggcg atagtttaca    2160
tgaacatatt gcaaatttag ctggtagccc tgctattaaa aaaggtattt tacagactgt    2220
aaaagttgtt gatgaattgg tcaaagtaat ggggcggcat aagccagaaa atatcgttat    2280
tgaaatggca cgtgaaaatc agacaactca aagggccag aaaaattcgc gagagcgtat    2340
gaaacgaatc gaagaaggta tcaaagaatt aggaagtcag attcttaaag agcatcctgt    2400
tgaaaatact caattgcaaa atgaaaagct ctatctctat tatctccaaa atggaagaga    2460
catgtatgtg gaccaagaat tagatattaa tcgtttaagt gattatgatg tcgatcacat    2520
tgttccacaa agtttcctta agacgattc aatagacaat aaggtcttaa cgcgttctga    2580
taaaaatcgt ggtaaatcgg ataacgttcc aagtgaagaa gtagtcaaaa agatgaaaaa    2640
ctattggaga caacttctaa acgccaagtt aatcactcaa cgtaagtttg ataatttaac    2700
gaaagctgaa cgtggaggtt tgagtgaact tgataaagct ggtttatca aacgccaatt    2760 ggttgaaact cgccaaatca ctaagcatgt ggcacaaatt ttggatagtc gcatgaatac    2820
taaatacgat gaaaatgata aacttattcg agaggttaaa gtgattaccct aaaatctaa    2880 attagtttct gacttccgaa aagatttcca attctataaa gtacgtgaga ttaacaatta    2940
ccatcatgcc catgatgcgt atctaaatgc cgtcgttgga actgctttga ttaagaaata    3000
tccaaaactt gaatcggagt ttgtctatgg tgattataaa gtttatgatg ttcgtaaaat    3060
gattgctaag tctgagcaag aaataggcaa agcaaccgca aaatatttct tttactctaa    3120
tatcatgaac ttcttcaaaa cagaaattac acttgcaaat ggagagattc gcaaacgccc    3180
tctaatcgaa actaatgggg aaactggaga aattgtctgg gataaagggc gagattttgc    3240
cacagtgcgc aaagtattgt ccatgcccca agtcaatatt gtcaagaaaa cagaagtaca    3300
gacaggcgga ttctccaagg agtcaatttt accaaaaaga aattcggaca agcttattgc    3360
tcgtaaaaaa gactgggatc aaaaaaaata tggtggtttt gatagtccaa cggtagctta    3420
ttcagtccta gtggttgcta aggtggaaaa agggaaatcg aagaagttaa aatccgttaa    3480
agagttacta gggatcacaa ttatggaaag aagttccttt gaaaaaaatc cgattgactt    3540
tttagaagct aaaggatata aggaagttaa aaaagactta atcattaaac tacctaaata    3600 tagtctttt gagttagaaa acggtcgtaa acggatgctg gctagtgccg gagaattaca    3660
aaaaggaaat gagctggctc tgccaagcaa atatgtgaat ttttatatt tagctagtca    3720 ttatgaaaag ttgaagggta gtccagaaga taacgaacaa aaacaattgt tgtggagca    3780 gcataagcat tatttagatg agattattga gcaaatcagt gaattttcta agcgtgttat    3840
tttagcagat gccaattag ataaagttct tagtgcatat aacaaacata gagacaaacc    3900
```

```
aatacgtgaa caagcagaaa atattattca tttatttacg ttgacgaatc ttggagctcc    3960
cgctgctttt aaatattttg atacaacaat tgatcgtaaa cgatatacgt ctacaaaaga    4020
agttttagat gccactctat ccatcaatcc atcactggtc tttatgaaac acgcattgat    4080
ttgagtcagc taggaggtga ctga                                           4104
```

<210> SEQ ID NO 14
<211> LENGTH: 1054
<212> TYPE: PRT
<213> ORGANISM: Artificial Sequence
<220> FEATURE:
<223> OTHER INFORMATION: A synthetic amino acid sequence

<400> SEQUENCE: 14

```
Met Lys Glu Lys Tyr Ile Leu Gly Leu Asp Leu Gly Ile Thr Ser Val
1               5                   10                  15

Gly Tyr Gly Ile Ile Asn Phe Glu Thr Lys Lys Ile Ile Asp Ala Gly
            20                  25                  30

Val Arg Leu Phe Pro Glu Ala Asn Val Asp Asn Asn Glu Gly Arg Arg
        35                  40                  45

Ser Lys Arg Gly Ser Arg Arg Leu Lys Arg Arg Ile His Arg Leu
    50                  55                  60

Glu Arg Val Lys Leu Leu Leu Thr Glu Tyr Asp Leu Ile Asn Lys Glu
65                  70                  75                  80

Gln Ile Pro Thr Ser Asn Asn Pro Tyr Gln Ile Arg Val Lys Gly Leu
                85                  90                  95

Ser Glu Ile Leu Ser Lys Asp Glu Leu Ala Ile Ala Leu Leu His Leu
            100                 105                 110

Ala Lys Arg Arg Gly Ile His Asn Ile Asn Val Ser Ser Glu Asp Glu
        115                 120                 125

Asp Ala Ser Asn Glu Leu Ser Thr Lys Glu Gln Ile Asn Arg Asn Asn
    130                 135                 140

Lys Leu Leu Lys Asp Lys Tyr Val Cys Glu Val Gln Leu Gln Arg Leu
145                 150                 155                 160

Lys Glu Gly Gln Ile Arg Gly Glu Lys Asn Arg Phe Lys Thr Thr Asp
                165                 170                 175

Ile Leu Lys Glu Ile Asp Gln Leu Leu Lys Val Gln Lys Asp Tyr His
            180                 185                 190

Asn Leu Asp Ile Asp Phe Ile Asn Gln Tyr Lys Glu Ile Val Glu Thr
        195                 200                 205

Arg Arg Glu Tyr Phe Glu Gly Pro Gly Gln Gly Ser Pro Phe Gly Trp
    210                 215                 220

Asn Gly Asp Leu Lys Lys Trp Tyr Glu Met Leu Met Gly His Cys Thr
225                 230                 235                 240

Tyr Phe Pro Gln Glu Leu Arg Ser Val Lys Tyr Ala Tyr Ser Ala Asp
                245                 250                 255

Leu Phe Asn Ala Leu Asn Asp Leu Asn Asn Leu Ile Ile Gln Arg Asp
            260                 265                 270

Asn Ser Glu Lys Leu Glu Tyr His Glu Lys Tyr His Ile Ile Glu Asn
        275                 280                 285

Val Phe Lys Gln Lys Lys Lys Pro Thr Leu Lys Gln Ile Ala Lys Glu
    290                 295                 300

Ile Gly Val Asn Pro Glu Asp Ile Lys Gly Tyr Arg Ile Thr Lys Ser
305                 310                 315                 320
```

```
Gly Thr Pro Gln Phe Thr Glu Phe Lys Leu Tyr His Asp Leu Lys Ser
                325                 330                 335

Ile Val Phe Asp Lys Ser Ile Leu Glu Asn Glu Ala Ile Leu Asp Gln
            340                 345                 350

Ile Ala Glu Ile Leu Thr Ile Tyr Gln Asp Glu Gln Ser Ile Lys Glu
            355                 360                 365

Glu Leu Asn Lys Leu Pro Glu Ile Leu Asn Glu Gln Asp Lys Ala Glu
        370                 375                 380

Ile Ala Lys Leu Ile Gly Tyr Asn Gly Thr His Arg Leu Ser Leu Lys
385                 390                 395                 400

Cys Ile His Leu Ile Asn Glu Glu Leu Trp Gln Thr Ser Arg Asn Gln
                405                 410                 415

Met Glu Ile Phe Asn Tyr Leu Asn Ile Lys Pro Asn Lys Val Asp Leu
            420                 425                 430

Ser Glu Gln Asn Lys Ile Pro Lys Asp Met Val Asn Asp Phe Ile Leu
            435                 440                 445

Ser Pro Val Val Lys Arg Thr Phe Ile Gln Ser Ile Asn Val Ile Asn
        450                 455                 460

Lys Val Ile Glu Lys Tyr Gly Ile Pro Glu Asp Ile Ile Glu Leu
465                 470                 475                 480

Ala Arg Glu Asn Asn Ser Asp Asp Arg Lys Lys Phe Ile Asn Asn Leu
                485                 490                 495

Gln Lys Lys Asn Glu Ala Thr Arg Lys Arg Ile Asn Glu Ile Ile Gly
            500                 505                 510

Gln Thr Gly Asn Gln Asn Ala Lys Arg Ile Val Glu Lys Ile Arg Leu
            515                 520                 525

His Asp Gln Gln Glu Gly Lys Cys Leu Tyr Ser Leu Glu Ser Ile Ala
        530                 535                 540

Leu Met Asp Leu Leu Asn Asn Pro Gln Asn Tyr Glu Val Asp His Ile
545                 550                 555                 560

Ile Pro Arg Ser Val Ala Phe Asp Asn Ser Ile His Asn Lys Val Leu
                565                 570                 575

Val Lys Gln Ile Glu Asn Ser Lys Lys Gly Asn Arg Thr Pro Tyr Gln
            580                 585                 590

Tyr Leu Asn Ser Ser Asp Ala Lys Leu Ser Tyr Asn Gln Phe Lys Gln
            595                 600                 605

His Ile Leu Asn Leu Ser Lys Ser Lys Asp Arg Ile Ser Lys Lys Lys
        610                 615                 620

Lys Asp Tyr Leu Leu Glu Glu Arg Asp Ile Asn Lys Phe Glu Val Gln
625                 630                 635                 640

Lys Glu Phe Ile Asn Arg Asn Leu Val Asp Thr Arg Tyr Ala Thr Arg
                645                 650                 655

Glu Leu Thr Ser Tyr Leu Lys Ala Tyr Phe Ser Ala Asn Asn Met Asp
            660                 665                 670

Val Lys Val Lys Thr Ile Asn Gly Ser Phe Thr Asn His Leu Arg Lys
            675                 680                 685

Val Trp Arg Phe Asp Lys Tyr Arg Asn His Gly Tyr Lys His His Ala
        690                 695                 700

Glu Asp Ala Leu Ile Ile Ala Asn Ala Asp Phe Leu Phe Lys Glu Asn
705                 710                 715                 720

Lys Lys Leu Gln Asn Ala Asn Lys Ile Leu Glu Lys Pro Thr Ile Glu
                725                 730                 735

Asn Asn Thr Lys Lys Val Thr Val Glu Lys Glu Glu Asp Tyr Asn Asn
```

```
                740                 745                 750
Val Phe Glu Thr Pro Lys Leu Val Glu Asp Ile Lys Gln Tyr Arg Asp
            755                 760                 765

Tyr Lys Phe Ser His Arg Val Asp Lys Lys Pro Asn Arg Gln Leu Ile
        770                 775                 780

Asn Asp Thr Leu Tyr Ser Thr Arg Met Lys Asp Glu His Asp Tyr Ile
785                 790                 795                 800

Val Gln Thr Ile Thr Asp Ile Tyr Gly Lys Asp Asn Thr Asn Leu Lys
                805                 810                 815

Lys Gln Phe Asn Lys Asn Pro Glu Lys Phe Leu Met Tyr Gln Asn Asp
            820                 825                 830

Pro Lys Thr Phe Glu Lys Leu Ser Ile Ile Met Lys Gln Tyr Ser Asp
        835                 840                 845

Glu Lys Lys Pro Leu Ala Lys Tyr Tyr Glu Thr Gly Glu Tyr Leu
    850                 855                 860

Thr Lys Tyr Ser Lys Lys Asn Asn Gly Pro Ile Val Lys Lys Ile Lys
865                 870                 875                 880

Leu Leu Gly Asn Lys Val Gly Asn His Leu Asp Val Thr Asn Lys Tyr
                885                 890                 895

Glu Asn Ser Thr Lys Lys Leu Val Lys Leu Ser Ile Lys Asn Tyr Arg
            900                 905                 910

Phe Asp Val Tyr Leu Thr Glu Lys Gly Tyr Lys Phe Val Thr Ile Ala
        915                 920                 925

Tyr Leu Asn Val Phe Lys Lys Asp Asn Tyr Tyr Tyr Ile Pro Lys Asp
    930                 935                 940

Lys Tyr Gln Glu Leu Lys Glu Lys Lys Ile Lys Asp Thr Asp Gln
945                 950                 955                 960

Phe Ile Ala Ser Phe Tyr Lys Asn Asp Leu Ile Lys Leu Asn Gly Asp
                965                 970                 975

Leu Tyr Lys Ile Ile Gly Val Asn Ser Asp Asp Arg Asn Ile Ile Glu
            980                 985                 990

Leu Asp Tyr Tyr Asp Ile Lys Tyr Lys Asp Tyr Cys Glu Ile Asn Asn
        995                 1000                1005

Ile Lys Gly Glu Pro Arg Ile Lys Lys Thr Ile Gly Lys Lys Thr Glu
    1010                1015                1020

Ser Ile Glu Lys Phe Thr Thr Asp Val Leu Gly Asn Leu Tyr Leu His
1025                1030                1035                1040

Ser Thr Glu Lys Ala Pro Gln Leu Ile Phe Lys Arg Gly Leu
                1045                1050
```

<210> SEQ ID NO 15
<211> LENGTH: 1370
<212> TYPE: PRT
<213> ORGANISM: Artificial Sequence
<220> FEATURE:
<223> OTHER INFORMATION: A synthetic amino acid sequence

<400> SEQUENCE: 15

```
Met Asn Lys Pro Tyr Ser Ile Gly Leu Asp Ile Gly Thr Asn Ser Val
1               5                   10                  15

Gly Trp Ser Ile Ile Thr Asp Asp Tyr Lys Val Pro Ala Lys Lys Met
            20                  25                  30

Arg Val Leu Gly Asn Thr Asp Lys Glu Tyr Ile Lys Lys Asn Leu Ile
        35                  40                  45

Gly Ala Leu Leu Phe Asp Gly Gly Asn Thr Ala Ser Asp Arg Arg Leu
```

```
            50                  55                  60
Lys Arg Thr Ala Arg Arg Tyr Thr Arg Arg Asn Arg Ile Leu
 65                  70                  75                  80

Tyr Leu Gln Glu Ile Phe Ala Glu Met Ser Lys Val Asp Asp Ser
                     85                  90                  95

Phe Phe His Arg Leu Glu Asp Ser Phe Leu Val Glu Asp Lys Arg
                100                 105                 110

Gly Ser Lys Tyr Pro Ile Phe Ala Thr Met Gln Glu Glu Lys Asp Tyr
            115                 120                 125

His Glu Lys Phe Pro Thr Ile Tyr His Leu Arg Lys Glu Leu Ala Asp
    130                 135                 140

Lys Lys Glu Lys Ala Asp Leu Arg Leu Phe Tyr Leu Ala Leu Ala His
145                 150                 155                 160

Ile Ile Lys Phe Arg Gly His Phe Leu Ile Glu Asp Asp Ser Phe Asp
                165                 170                 175

Val Arg Asn Thr Asp Ile Gln Arg Gln Tyr Gln Ala Phe Leu Glu Ile
                180                 185                 190

Phe Asp Thr Thr Phe Glu Asn Asn His Leu Leu Ser Gln Asn Ile Asp
                195                 200                 205

Val Glu Gly Ile Leu Thr Asp Lys Ile Ser Lys Ser Ala Lys Lys Asp
    210                 215                 220

Arg Ile Leu Ala Gln Tyr Pro Asn Gln Lys Ser Thr Gly Ile Phe Ala
225                 230                 235                 240

Glu Phe Leu Lys Leu Ile Val Gly Asn Gln Ala Asp Phe Lys Lys His
                245                 250                 255

Phe Asn Leu Glu Asp Lys Thr Pro Leu Gln Phe Ala Lys Asp Ser Tyr
                260                 265                 270

Asp Glu Asp Leu Glu Asn Leu Leu Gly Gln Ile Gly Asp Glu Phe Ala
                275                 280                 285

Asp Leu Phe Ser Val Ala Lys Lys Leu Tyr Asp Ser Val Leu Leu Ser
                290                 295                 300

Gly Ile Leu Thr Val Thr Asp Leu Ser Thr Lys Ala Pro Leu Ser Ala
305                 310                 315                 320

Ser Met Ile Gln Arg Tyr Asp Glu His Arg Glu Asp Leu Lys Gln Leu
                325                 330                 335

Lys Gln Phe Val Lys Ala Ser Leu Pro Glu Lys Tyr Gln Glu Ile Phe
                340                 345                 350

Thr Asp Ser Ser Lys Asp Gly Tyr Ala Gly Tyr Ile Glu Gly Lys Thr
                355                 360                 365

Asn Gln Gly Ala Phe Tyr Lys Tyr Leu Ser Lys Leu Leu Thr Lys Gln
                370                 375                 380

Glu Gly Ser Glu Tyr Phe Leu Glu Lys Ile Lys Asn Glu Asp Phe Leu
385                 390                 395                 400

Arg Lys Gln Arg Thr Phe Asp Asn Gly Ser Ile Pro His Gln Val His
                405                 410                 415

Leu Thr Glu Leu Lys Ala Ile Ile Arg Arg Gln Ser Glu Tyr Tyr Pro
                420                 425                 430

Phe Leu Lys Glu Asn Leu Asp Arg Ile Glu Lys Ile Leu Thr Phe Arg
                435                 440                 445

Ile Pro Tyr Tyr Val Gly Pro Leu Ala Arg Glu Lys Ser Asp Phe Ala
                450                 455                 460

Trp Met Thr Arg Lys Thr Asp Asp Ser Ile Arg Pro Trp Asn Phe Glu
465                 470                 475                 480
```

```
Glu Leu Val Asp Lys Glu Ala Ser Ala Glu Ala Phe Ile His Arg Met
            485                 490                 495

Thr Asn Asn Asp Leu Tyr Leu Pro Glu Lys Val Leu Pro Lys His
                500                 505                 510

Ser Leu Ile Tyr Glu Lys Phe Thr Val Tyr Asn Glu Leu Thr Lys Val
            515                 520                 525

Arg Tyr Lys Asn Glu Gln Gly Glu Thr Tyr Phe Phe Asp Ser Asn Ile
            530                 535                 540

Lys Gln Glu Ile Phe Asp Gly Val Phe Lys Glu His Arg Lys Val Ser
545                 550                 555                 560

Lys Lys Lys Leu Leu Asp Phe Leu Ala Lys Glu Tyr Glu Glu Phe Arg
                565                 570                 575

Ile Val Asp Val Ile Gly Leu Asp Lys Glu Asn Lys Ala Phe Asn Ala
                580                 585                 590

Ser Leu Gly Thr Tyr His Asp Leu Lys Lys Ile Leu Asp Lys Asp Phe
            595                 600                 605

Leu Asp Asn Pro Asp Asn Glu Ser Ile Leu Glu Asp Ile Val Gln Thr
610                 615                 620

Leu Thr Leu Phe Glu Asp Arg Glu Met Ile Lys Lys Arg Leu Glu Asn
625                 630                 635                 640

Tyr Lys Asp Leu Phe Thr Glu Ser Gln Leu Lys Lys Leu Tyr Arg Arg
                645                 650                 655

His Tyr Thr Gly Trp Gly Arg Leu Ser Ala Lys Leu Ile Asn Gly Ile
            660                 665                 670

Arg Asp Lys Glu Ser Gln Lys Thr Ile Leu Asp Tyr Leu Ile Asp Asp
            675                 680                 685

Gly Lys Ser Asn Arg Asn Phe Met Gln Leu Ile His Asp Asp Gly Leu
690                 695                 700

Ser Phe Lys Ser Ile Ile Ser Lys Ala Gln Ala Gly Ser His Ser Asp
705                 710                 715                 720

Asn Leu Lys Glu Val Val Gly Glu Leu Ala Gly Ser Pro Ala Ile Lys
                725                 730                 735

Lys Gly Ile Leu Gln Ser Leu Lys Ile Val Asp Glu Leu Val Lys Val
                740                 745                 750

Met Gly Tyr Glu Pro Glu Gln Ile Val Val Glu Met Ala Arg Glu Asn
                755                 760                 765

Gln Thr Thr Asn Gln Gly Arg Arg Asn Ser Arg Gln Arg Tyr Lys Leu
            770                 775                 780

Leu Asp Asp Gly Val Lys Asn Leu Ala Ser Asp Leu Asn Gly Asn Ile
785                 790                 795                 800

Leu Lys Glu Tyr Pro Thr Asp Asn Gln Ala Leu Gln Asn Glu Arg Leu
                805                 810                 815

Phe Leu Tyr Tyr Leu Gln Asn Gly Arg Asp Met Tyr Thr Gly Lys Ala
                820                 825                 830

Leu Asp Ile Asp Asn Leu Ser Gln Tyr Asp Ile Asp His Ile Ile Pro
            835                 840                 845

Gln Ala Phe Ile Lys Asp Asp Ser Ile Asp Asn Arg Val Leu Val Ser
850                 855                 860

Ser Ala Lys Asn Arg Gly Lys Ser Asp Asp Val Pro Ser Leu Glu Ile
865                 870                 875                 880

Val Lys Asp Cys Lys Val Phe Trp Lys Lys Leu Leu Asp Ala Lys Leu
                885                 890                 895
```

```
Met Ser Gln Arg Lys Tyr Asp Asn Leu Thr Lys Ala Glu Arg Gly Gly
                900                 905                 910
Leu Thr Ser Asp Asp Lys Ala Arg Phe Ile Gln Arg Gln Leu Val Glu
            915                 920                 925
Thr Arg Gln Ile Thr Lys His Val Ala Arg Ile Leu Asp Glu Arg Phe
        930                 935                 940
Asn Asn Glu Leu Asp Ser Lys Gly Arg Arg Ile Arg Lys Val Lys Ile
945                 950                 955                 960
Val Thr Leu Lys Ser Asn Leu Val Ser Asn Phe Arg Lys Glu Phe Gly
                965                 970                 975
Phe Tyr Lys Ile Arg Glu Val Asn Asn Tyr His His Ala His Asp Ala
            980                 985                 990
Tyr Leu Asn Ala Val Val Ala Lys Ala Ile Leu Thr Lys Tyr Pro Gln
        995                 1000                1005
Leu Glu Pro Glu Phe Val Tyr Gly Asp Tyr Pro Lys Tyr Asn Ser Tyr
        1010                1015                1020
Lys Thr Arg Lys Ser Ala Thr Glu Lys Leu Phe Phe Tyr Ser Asn Ile
1025                1030                1035                1040
Met Asn Phe Phe Lys Thr Lys Val Thr Leu Ala Asp Gly Thr Val Val
                1045                1050                1055
Val Lys Asp Asp Ile Glu Val Asn Asn Asp Thr Gly Glu Ile Val Trp
            1060                1065                1070
Asp Lys Lys Lys His Phe Ala Thr Val Arg Lys Val Leu Ser Tyr Pro
        1075                1080                1085
Gln Val Asn Ile Val Lys Lys Thr Glu Ile Gln Thr Gly Gly Phe Ser
        1090                1095                1100
Lys Glu Ser Ile Leu Ala His Gly Asn Ser Asp Lys Leu Ile Pro Arg
1105                1110                1115                1120
Lys Thr Lys Asp Ile Tyr Leu Asp Pro Lys Lys Tyr Gly Gly Phe Asp
                1125                1130                1135
Ser Pro Ile Val Ala Tyr Ser Val Leu Val Val Ala Asp Ile Lys Lys
            1140                1145                1150
Gly Lys Ala Gln Lys Leu Lys Thr Val Thr Glu Leu Leu Gly Ile Thr
        1155                1160                1165
Ile Met Glu Arg Ser Arg Phe Glu Lys Asn Pro Ser Ala Phe Leu Glu
        1170                1175                1180
Ser Lys Gly Tyr Leu Asn Ile Arg Asp Asp Lys Leu Met Ile Leu Pro
1185                1190                1195                1200
Lys Tyr Ser Leu Phe Glu Leu Glu Asn Gly Arg Arg Arg Leu Leu Ala
                1205                1210                1215
Ser Ala Gly Glu Leu Gln Lys Gly Asn Glu Leu Ala Leu Pro Thr Gln
            1220                1225                1230
Phe Met Lys Phe Leu Tyr Leu Ala Ser Arg Tyr Asn Glu Leu Lys Gly
        1235                1240                1245
Lys Pro Glu Glu Ile Glu Gln Lys Gln Glu Phe Val Val Gln His Val
        1250                1255                1260
Ser Tyr Phe Asp Asp Ile Leu Gln Ile Ile Asn Asp Phe Ser Asn Arg
1265                1270                1275                1280
Val Ile Leu Ala Asp Ala Asn Leu Glu Lys Ile Asn Lys Leu Tyr Gln
                1285                1290                1295
Asp Asn Lys Glu Asn Ile Ser Val Asp Glu Leu Ala Asn Asn Ile Ile
            1300                1305                1310
Asn Leu Phe Thr Phe Thr Ser Leu Gly Ala Pro Ala Ala Phe Lys Phe
```

-continued

```
            1315                1320                1325
Phe Asp Lys Ile Val Asp Arg Lys Arg Tyr Thr Ser Thr Lys Glu Val
    1330                1335                1340

Leu Asn Ser Thr Leu Ile His Gln Ser Ile Thr Gly Leu Tyr Glu Thr
1345                1350                1355                1360

Arg Ile Asp Leu Gly Lys Leu Gly Glu Asp
                1365                1370
```

What is claimed is:

1. Synthetic double stranded (ds) mRNA comprising one strand of RNA encoding a therapeutic or prophylactic protein, wherein at least one strand of the ds mRNA has a 5' cap, a start codon, a polyA sequence and encodes the protein, wherein the two strands of the ds mRNA are hydrogen bonded over at least 50% of the length of the strands, wherein the hydrogen bonded region includes at least a portion of the coding region for the protein.

2. The synthetic ds mRNA of claim 1 wherein at least one strand includes one or more non-natural nucleotides and wherein the two strands of the ds mRNA are hydrogen bonded over at least 80% of the length of the strands.

3. The synthetic ds mRNA of claim 2 wherein at least one of the non-natural nucleotides has a non-natural sugar, at least one of the non-natural nucleotides has a non-natural nucleobase, or a combination thereof.

4. The synthetic ds mRNA of claim 2 which includes 5-formyl cytidine or pseudouridine.

5. The synthetic ds mRNA of claim 2 wherein at least 5% of the nucleotides are non-natural nucleotides.

6. The synthetic ds mRNA of claim 2 wherein the non-natural nucleotide analog is a purine analog.

7. The synthetic ds mRNA of claim 1 wherein at least one strand includes at least one non-phosphodiester bond.

8. The synthetic ds mRNA of claim 1 wherein one of the strands is no more than 5 kb in length.

9. The synthetic ds mRNA of claim 1 wherein at least one strand has two or more different non-natural nucleotides.

10. A method of making a double stranded (ds) mRNA encoding a prophylactic or therapeutic protein, comprising:

providing a strand of mRNA having a 5' cap, a start codon, a polyA sequence and an open reading frame for the protein; providing a strand of RNA that has sequence complementarity with the mRNA over at least 50% of the length of the strands, wherein the hydrogen bonded region includes at least a portion of the coding region for the protein; and allowing the snRNA and the RNA with sequence complementarity to form hydrogen bond, thereby providing the ds mRNA.

11. The method of claim 10 wherein one or more nucleotide modifications are introduced post-synthesis to at least one of the strands.

12. The method of claim 10 wherein one or more non-natural nucleotides are incorporated during synthesis to at least one of the strands.

13. The method of claim 10 wherein the strands are hydrogen bonded over at least 90% of the length of the strands.

14. The method of claim 10 wherein the strands are not the same length.

* * * * *

UNITED STATES PATENT AND TRADEMARK OFFICE
CERTIFICATE OF CORRECTION

PATENT NO. : 11,007,213 B2
APPLICATION NO. : 16/090468
DATED : May 18, 2021
INVENTOR(S) : Rice et al.

Page 1 of 2

It is certified that error appears in the above-identified patent and that said Letters Patent is hereby corrected as shown below:

On the Title Page

Item [54], delete "MRNA" and insert --mRNA-- therefor

Column 2, Line 21, delete ""Imune" and insert --"Immune-- therefor

Column 2, Line 33, delete "stern" and insert --stem-- therefor

Column 2, Line 36, delete ""Imunotherapy" and insert --"Immunotherapy-- therefor In the Specification Column 1, Line 2, delete "MRNA" and insert --mRNA-- therefor Column 1, Line 45, delete "at" and insert --et-- therefor Column 3, Lines 26-27, delete "5-formylcytidine-5-triphosphate," and insert --5-formylcytidine-5'-triphosphate.-- therefor Column 3, Line 54, delete "3'-deoxyundine-5'-triphosphate," and insert --3'-deoxyuridine-5'-triphosphate,-- therefor Column 4, Line 45, delete "the the" and insert --the-- therefor Column 10, Line 32, delete "dotting" and insert --clotting-- therefor Column 11, Line 27, delete "Deoxynbonuclease" and insert --Deoxyribonuclease-- therefor Column 11, Line 28, delete "disorder," and insert --disorder;-- therefor Signed and Sealed this
Eleventh Day of October, 2022

Katherine Kelly Vidal
*Director of the United States Patent and Trademark Office*

CERTIFICATE OF CORRECTION (continued)
U.S. Pat. No. 11,007,213 B2

Column 11, Lines 57-58, delete "SERPINF1." and Insert ---SERPINF1,-- therefor

Column 12, Line 21, delete "adenomas." and insert --adenomas,-- therefor

Column 20, Line 21, delete "Growth-GF-1" and insert --Growth-IGF-1-- therefor

Column 20, Line 33, delete "Dyslioidemias" and insert --Dyslipidemias-- therefor Column 22, Line 32, delete "Cardiomyopathy." and insert --Cardiomyopathy,-- therefor Column 22, Line 32, delete "disease." and insert --disease,-- therefor Column 22, Line 33, delete "Corpulmonale." and insert --Corpulmonale,-- therefor Column 25, Lines 44-45, delete "4-amino-1-(2-deoxy-2,2-difluoro-A-D-erythro-pentofuranosyl)pyrimidin-1-2(1H)-one;" and insert --4-amino-1-(2-deoxy-2,2-difluoro-β-D-erythro-pentofuranosyl)pyrimidin--2(1H)-one;-- therefor Column 25, Line 60, delete "acydonucleotide," and insert --acyclonucleotide,-- therefor Column 26, Line 22, delete "(a vs. 3)." and insert --(α vs. β).-- therefor Column 33, Line 46, delete "dendnimers," and insert --dendrimers,-- therefor Column 63, Line 33, delete "Release." and insert --Release,-- therefor Column 63, Line 35, delete "2:911" and insert --3:911-- therefor Column 64, Line 2, delete "29:948" and insert --20:948-- therefor Column 64, Line 3, delete "22:154" and insert --29:154-- therefor Column 64, Line 15, delete "0.1:746" and insert --16:746-- therefor Column 64, Line 21, delete "at" and insert --et-- therefor Column 64, Line 25, delete "3:898" and insert --31:898-- therefor In the Claims Column 112, Line 25, Claim 10, delete "snRNA" and insert --mRNA-- therefor